(12) United States Patent
Clark

(10) Patent No.: US 8,759,300 B2
(45) Date of Patent: Jun. 24, 2014

(54) POLYPEPTIDES AND METHODS OF USE

(75) Inventor: Richard A. Clark, Poquott, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 1137 days.

(21) Appl. No.: 12/663,993

(22) PCT Filed: Jun. 16, 2008

(86) PCT No.: PCT/US2008/067105
§ 371 (c)(1),
(2), (4) Date: Jul. 7, 2010

(87) PCT Pub. No.: WO2008/157483
PCT Pub. Date: Dec. 24, 2008

(65) Prior Publication Data
US 2010/0292161 A1   Nov. 18, 2010

Related U.S. Application Data

(60) Provisional application No. 60/944,068, filed on Jun. 14, 2007, provisional application No. 60/986,976, filed on Nov. 9, 2007.

(51) Int. Cl.
| | | |
|---|---|---|
| *C07K 7/08* | (2006.01) | |
| *A61K 38/10* | (2006.01) | |
| *A61P 17/02* | (2006.01) | |
| *A61K 9/00* | (2006.01) | |
| *A61F 13/00* | (2006.01) | |
| *G01N 33/50* | (2006.01) | |
| *A61L 27/22* | (2006.01) | |
| *C07K 14/78* | (2006.01) | |
| *A61K 38/00* | (2006.01) | |

(52) U.S. Cl.
CPC ............ *C07K 14/78* (2013.01); *G01N 2500/02* (2013.01); *G01N 33/5032* (2013.01); *A61L 27/227* (2013.01); *A61K 38/00* (2013.01); *G01N 2333/71* (2013.01)
USPC ....... 514/21.5; 514/21.4; 514/9.4; 424/78.06; 602/42

(58) Field of Classification Search
None
See application file for complete search history.

(56) References Cited

U.S. PATENT DOCUMENTS

| | | | |
|---|---|---|---|
| 4,179,337 A | 12/1979 | Davis et al. | |
| 4,301,144 A | 11/1981 | Iwashita et al. | |
| 4,496,689 A | 1/1985 | Mitra | |
| 4,522,811 A | 6/1985 | Eppstein et al. | |
| 4,640,835 A | 2/1987 | Shimizu et al. | |
| 4,670,417 A | 6/1987 | Iwasaki et al. | |
| 4,791,192 A | 12/1988 | Nakagawa et al. | |
| 4,939,239 A | 7/1990 | Matsuhashi et al. | |
| 5,051,448 A | 9/1991 | Shashoua | |
| 5,166,320 A | 11/1992 | Wu et al. | |
| 5,169,862 A | 12/1992 | Burke, Jr. et al. | |
| 5,192,746 A | 3/1993 | Lobl et al. | |
| 5,270,168 A | 12/1993 | Grinnell | |
| 5,283,173 A | 2/1994 | Fields et al. | |
| 5,288,514 A | 2/1994 | Ellman | |
| 5,359,115 A | 10/1994 | Campbell et al. | |
| 5,362,899 A | 11/1994 | Campbell | |
| 5,453,489 A * | 9/1995 | Ruoslahti et al. ............. 530/350 |
| 5,539,085 A | 7/1996 | Bischoff et al. | |
| 5,559,103 A | 9/1996 | Gaeta et al. | |
| 5,576,423 A | 11/1996 | Aversa et al. | |
| 6,799,657 B2 | 10/2004 | Daniels | |
| 6,808,923 B2 | 10/2004 | Engelman et al. | |
| 6,818,209 B1 | 11/2004 | Mitrophanous et al. | |
| 6,830,892 B2 | 12/2004 | Marasco et al. | |
| 6,863,884 B2 | 3/2005 | Schauber et al. | |
| 6,924,123 B2 | 8/2005 | Kingsman et al. | |
| 7,105,341 B2 | 9/2006 | Kinsella | |
| 2004/0120918 A1 | 6/2004 | Lintner et al. | |
| 2005/0008604 A1 | 1/2005 | Schultz et al. | |
| 2005/0025725 A1 | 2/2005 | Schultz et al. | |
| 2005/0282747 A1 | 12/2005 | Clark et al. | |
| 2006/0038778 A1 | 2/2006 | Boon et al. | |

FOREIGN PATENT DOCUMENTS

| | | | |
|---|---|---|---|
| JP | 07-113623 | | 5/1995 |
| SE | WO-2005/061535 | * | 7/2005 |
| WO | WO91/07087 | | 5/1991 |
| WO | WO92/10092 | | 6/1992 |
| WO | WO93/09668 | | 5/1993 |
| WO | WO93/20242 | | 10/1993 |
| WO | WO94/08051 | | 4/1994 |
| WO | WO 02/090377 | | 11/2002 |
| WO | WO 03/016337 | | 2/2003 |
| WO | WO2005009510 | | 3/2005 |
| WO | WO2005117936 | | 12/2005 |
| WO | WO2007044396 | | 4/2007 |

OTHER PUBLICATIONS

Jezek, 1999, Journal of Peptide Science, 5, 46-55.*
Gairin, 1986, J. Med. Chem., 29, 1913-1917.*
Shirakova, 1977, Zhurnal Obshchei Khimi, 47, 932-935, 6 pages. (STN search notes).*
Goldstein, 1979, PNAS, 76, 6666-6670.*
Ambesi et al., "Ansatellin, a fragment of the first type III repeat of fribronectin, inhibits extracellular signal-regulated kinase and causes G(I) arrest in human microvessel endothelial cells", Cancer Res. 65:148-156, 2005.
Clark et al., "Fibronectin and fibrin provide a provisional matrix for epidermal cell migration during wound reepithelialization", J. Invest. Dermatol., 79:264-269, 1982.
Clark et al., "Blood vessel fribronectin increases in conjuction with endothelial cell proliferation and capillary ingrowth during would healing", J. Invest. Dermatol. 79:269-276, 1982.
Clark et al., "Fibronectin is produced by blood vessels in response to injury", J. Exp. Med. 156:646-651, 1982.
Clark et al., "Fibropectin beneath reepithelializing epidermis in vivo: Sources and significance", J. Invest. Dermatol. 80 (suppl.):26S-30S, 1983.

(Continued)

*Primary Examiner* — Satyanarayana R Gudibande
(74) *Attorney, Agent, or Firm* — Occhiuti & Rohlicek LLP

(57) ABSTRACT

Described herein are fragments of fibronectin and vitronectin and variants thereof that have certain activities, including growth factor-binding activity. Also described are fragments of growth factors that bind to fibronectin and inhibit binding of full-length growth factors to fibronectin. Compositions containing such fragments are useful in cosmetic treatments (e.g., the treatment of wrinkles or UV photodamage of skin), and the treatment of wounds and cancer.

18 Claims, 13 Drawing Sheets

(56) References Cited

OTHER PUBLICATIONS

Clark et al., "Either exogenous or endogenous fibronectin can promote adherence of human endothelial cells", J. Cell Sci. 82:263-280, 1986.
Clark et al., "Collagen matrices attenuate the collagen synthetic response of cultured fibroblasts to TGF-β", J. Cell Sci. 108:1251-1261, 1995.
Clark et al., "Fibroblast migration on fibronectin requires 3 distinct functional domains", J. Invest. Dermatol. 12:695-705, 2003.
Clark et al., "Tissue engineering for cutaneous wounds", J. Invest. Dermatol. 127:1018-1029, 2007.
Danilenko et al., "Growth factors in porcine full and partial thickness burn repair", Am. J. Pathol., 147:1261-1277, 1995.
Gialit and Clark, "Studies in vitro on the role of αv and β1 integrins in the adhesion of human dermal fibroblasts to provisional matrix proteins fribronectin, vitronectin, and fribrnogen", J. Invest. Dermatol. 106:102-108, 1996.
Garcia et al., "Modulation of cell proliferation and differentiation through substrate-dependent changes in fibronectin conformation", Mol. Biol. Cell 10:785-798, 1999.
Greenhalgh et al., "PDGF and FGF stimulate wound healing in the gentically diabetic mouse", Am. J. Path. 136:1235-1246, 1990.
Greiling and Clark, "Fibronectin provides a conduit for fibroblast transmigration from a collagen gel into a fibrin gel", J. Cell Sci. 110(Pt. 7):861-870, 1997.
Grinnell et al., "Degradation of fibronectin and vitronectin in chronic wound fluid: analysis by cell blotting, immunoblotting, and cell adhesion assays", J. Invest. Dermatol. 98:410-416, 1992.
Gui et al., "Identification of the heparin-binding determinants within fibronectin repeart III", J. Biol. Chem. 281:34816-34825, 2006.
Maile et al., "The heparin binding domain of vitronectin is the region that is required to enhance Insulin-like Growth Factor-I signaling", Mol. Endocrinol. 20:881-892, 2006.
Miyamoto et al., "Integrins can collaborate with growth factors for phosphorylation of receptor tyrosine kinases and MAP kinase activation: roles of integrin aggregation and occupancy of receptors", J. Cell. Biol. 135:1633-1642, 1996.
Wijelath et al., "Novel vascular endothelial growth factor binding domains of fibronectin enhance vascular endothelial growth factor biological activity", Circ. Res. 91:25-31, 2002.
Wijelath et al., Heparin-II domain of fibronectin is a vascular endothelial growth factor-binding domain, Cir. Res. 99:853-860, 2006.
Xu and Clark, "Extracellular matrix alters PDGF regulation of fibroblast integrins", J. Cell Biol. 132:239-249, 1996.
Kouki, A., et al. "Highly constrained cyclic (S,S)-CXaaC-peptides as inhibitors of fibrinogen binding to platelets," Journal of Thrombosis and Haemostasis, 3(10):2324-2330, 2005.
US 5,053,368, 10/1991, Gibson et al. (withdrawn)

\* cited by examiner

FIGURE 1: Human Plasma Fibronectin (FN)

The sequence of P02751 (FINC_HUMAN)(Cold-insoluble globulin)
In one-letter code:

```
        1          11         21         31         41         51
        MLRGPGPGLL LLAVQCLGTA VPSTGASKSK RQAQQMVQPQ SPVAVSQSKP GCYDNGKHYQ
   61   INQQWERTYL GNALVCTCYG GSRGFNCESK PEAEETCFDK YTGNTYRVGD TYERPKDSMI
  121   WDCTCIGAGR GRISCTIANR CHEGGQSYKI GDTWRRPHET GGYMLECVCL GNGKGEWTCK
  181   PIAEKCFDHA AGTSYVVGET WEKPYQGWMM VDCTCLGEGS GRITCTSRNR CNDQDTRTSY
  241   RIGDTWSKKD NRGNLLQCIC TGNGRGEWKC ERHTSVQTTS SGSGPFTDVR AAVYQPQPHP
  301   QPPPYGHCVT DSGVVYSVGM QWLKTQGNKQ MLCTCLGNGV SCQETAVTQT YGGNSNGEPC
  361   VLPFTYNGRT FYSCTTEGRQ DGHLWCSTTS NYEQDQKYSF CTDHTVLVQT QGGNSNGALC
  421   HFPFLYNNHN YTDCTSEGRR DNMKWCGTTQ NYDADQKFGF CPMAAHEEIC TTNEGVMYRI
  481   GDQWDKQHDM GHMMRCTCVG NGRGEWTCIA YSQLRDQCIV DDITYNVNDT FHKRHEEGHM
  541   LNCTCFGQGR GRWKCDPVDQ CQDSETGTFY QIGDSWEKYV HGVRYQCYCY GRGIGEWHCQ
  601   PLQTYPSSSG PVEVFITETP SQPNSHPIQW NAPQPSHISK YILRWRPKNS VGRWKEATIP
  661   GHLNSYTIKG LKPGVVYEGQ LISIQQYGHQ EVTRFDFTTT STSTPVTSNT VTGETTPFSP
  721   LVATSESVTE ITASSFVVSW VSASDTVSGF RVEYELSEEG DEPQYLDLPS TATSVNIPDL
  781   LPGRKYIVNV YQISEDGEQS LILSTSQTTA PDAPPDPTVD QVDDTSIVVR WSRPQAPITG
  841   YRIVYSPSVE GSSTELNLPE TANSVTLSDL QPGVQYNITI YAVEENQEST PVVIQQETTG
  901   TPRSDTVPSP RDLQFVEVTD VKVTIMWTPP ESAVTGYRVD VIPVNLPGEH GQRLPISRNT
  961   FAEVTGLSPG VTYYFKVFAV SHGRESKPLT AQQTTKLDAP TNLQFVNETD STVLVRWTPP
 1021   RAQITGYRLT VGLTRRGQPR QYNVGPSVSK YPLRNLQPAS EYTVSLVAIK GNQESPKATG
 1081   VFTTLQPGSS IPPYNTEVTE TTIVITWTPA PRIGFKLGVR PSQGGEAPRE VTSDSGSIVV
 1141   SGLTPGVEYV YTIQVLRDGQ ERDAPIVNKV VTPLSPPTNL HLEANPDTGV LTVSWERSTT
 1201   PDITGYRITT TPTNGQQGNS LEEVVHADQS SCTFDNLSPG LEYNVSVYTV KDDKESVPIS
 1261   DTIIPAVPPP TDLRFTNIGP DTMRVTWAPP PSIDLTNFLV RYSPVKNEED VAELSISPSD
 1321   NAVVLTNLLP GTEYVVSVSS VYEQHESTPL RGRQKTGLDS PTGIDFSDIT ANSFTVHWIA
 1381   PRATITGYRI RHHPEHFSGR PREDRVPHSR NSITLTNLTP GTEYVVSIVA LNGREESPLL
 1441   IGQQSTVSDV PRDLEVVAAT PTSLLISWDA PAVTVRYYRI TYGETGGNSP VQEFTVPGSK
 1501   STATISGLKP GVDYTITVYA VTGRGDSPAS SKPISINYRT EIDKPSQMQV TDVQDNSISV
 1561   KWLPSSSPVT GYRVTTTPKN GPGPTKTKTA GPDQTEMTIE GLQPTVEYVV SVYAQNPSGE
 1621   SQPLVQTAVT NIDRPKGLAF TDVDVDSIKI AWESPQGQVS RYRVTYSSPE DGIHELFPAP
 1681   DGEEDTAELQ GLRPGSEYTV SVVALHDDME SQPLIGTQST AIPAPTDLKF TQVTPTSLSA
 1741   QWTPPNVQLT GYRVRVTPKE KTGPMKEINL APDSSSVVVS GLMVATKYEV SVYALKDTLT
 1801   SRPAQGVVTT LENVSPPRRA RVTDATETTI TISWRTKTET ITGFQVDAVP ANGQTPIQRT
 1861   IKPDVRSYTI TGLQPGTDYK IYLYTLNDNA RSSPVVIDAS TAIDAPSNLR FLATTPNSLL
 1921   VSWQPPRARI TGYIIKYEKP GSPPREVVPR PRPGVTEATI TGLEPGTEYT IYVIALKNNQ
 1981   KSEPLIGRKK TDELPQLVTL PHPNLHGPEI LDVPSTVQKT PFVTHPGYDT GNGIQLPGTS
 2041   GQQPSVGQQM IFEEHGFRRT TPPTTATPIR HRPRPYPPNV GEEIQIGHIP REDVDYHLYP
 2101   HGPGLNPNAS TGQEALSQTT ISWAPFQDTS EYIISCHPVG TDEEPLQFRV PGTSTSATLT
 2161   GLTRGATYNI IVEALKDQQR HKVREEVVTV GNSVNEGLNQ PTDDSCFDPY TVSHYAVGDE
 2221   WERMSESGFK LLCQCLGFGS GHFRCDSSRW CHDNGVNYKI GEKWDRQGEN GQMMSCTCLG
 2281   NGKGEFKCDP HEATCYDDGK TYHVGEQWQK EYLGAICSCT CFGGQRGWRC DNCRRPGGEP
 2341   SPEGTTGQSY NQYSQRYHQR TNTNVNCPIE CFMPLDVQAD REDSRE
```

FIG. 4 ref|NP_000651.3| transforming growth factor, beta 1 [Homo sapiens]

MPPSGLRLLPLLLPLLWLLVLTPGRPAAGLSTCKTIDMELVKRKRIEAIRGQILSKLRLA
PPSQGEVPPGPLPEAVLALYNSTRDRVAGESAEPEPEPEADYYAKEVTRVLMVETHNE
IYDKFKQSTHSIYMFFNTSELREAVPEPVLLSRAELRLLRLKLKVEQHVELYQKYSNNS
WRYLSNRLLAPSDSPEWLSFDVTGVVRQWLSRGGEIEGFRLSAHCSCDSRDNTLQVDI
NGFTTGRRGDLATIHGMNRPFLLLMATPLERAQHLQSSRHRRALDTNYCFSSTEKNCC
VRQLYIDFRKDLGWKWIHEPKGYHANFCLGPCPYIWSLDTQYSKVLALYNQHNPGAS
AAPCCVPQALEPLPIVYYVGRKPKVEQLSNMIVRSCKCS

FIG. 10A ref|NP_002599.1| platelet-derived growth factor beta isoform 1, preproprotein [Homo sapiens]

MNRCWALFLSLCCYLRLVSAEGDPIPEELYEMLSDHSIRSFDDLQRLLHGDPGEEDGA
LDLNMTRSHSGGELESLARGRRSLGSLTIAEPAMIAECKTRTEVFEISRRLIDRTNANFL
VWPPCVEVQRCSGCCNNRNVQCRPTQVQLRPVQVRKIEIVRKKPIFKKATVTLEDHLA
CKCETVAAARPVTRSPGGSQEQRAKTPQTRVTIRTVRVRRPPKGKHRKFKHTHDKTA
LKETLGA

FIG. 10B ref|NP_001997.5| fibroblast growth factor 2 [Homo sapiens]
MVGVGGGDVEDVTPRPGGCQISGRGARGCNGIPGAAAWEAALPRRRPRRHPSVNPRS
RAAGSPRTRGRRTEERPSGSRLGDRGRGRALPGGRLGGRGRGRAPERVGGRGRGRGT
AAPRAAPAARGSRPGPAGTMAAGSITTLPALPEDGGSGAFPPGHFKDPKRLYCKNGGF
FLRIHPDGRVDGVREKSDPHIKLQLQAEERGVVSIKGVCANRYLAMKEDGRLLASKC
VTDECFFFERLESNNYNTYRSRKYTSWYVALKRTGQYKLGSKTGPGQKAILFLPMSA
KS

FIG. 10C ref|NP_001020539.2| vascular endothelial growth factor A isoform d precursor [Homo sapiens]
MTDRQTDTAPSPSYHLLPGRRRTVDAAASRGQGPEPAPGGGVEGVGARGVALKLFV
QLGCSRFGGAVVRAGEAEPSGAARSASSGREEPQPEEGEEEEKEEERGPQWRLGAR
KPGSWTGEAAVCADSAPAARAPQALARASGRGGRVARRGAEESGPPHSPSRRGSASR
AGPGRASETMNFLLSWVHWSLALLLYLHHAKWSQAAPMAEGGGQNHHEVVKFMD
VYQRSYCHPIETLVDIFQEYPDEIEYIFKPSCVPLMRCGGCCNDEGLECVPTEESNITMQ
IMRIKPHQGQHIGEMSFLQHNKCECRPKKDRARQENPCGPCSERRKHLFVQDPQTCKC
SCKNTDSRCKARQLELNERTCRCDKPRR

FIG. 10D

SEQUENCE LISTING

<160> NUMBER OF SEQ ID NOS: 84

<210> SEQ ID NO 1
<211> LENGTH: 2386
<212> TYPE: PRT
<213> ORGANISM: Homo sapiens

<400> SEQUENCE: 1

```
Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
    290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
```

```
              355                 360                 365
Arg Thr Phe Tyr Ser Cys Thr Thr Glu Gly Arg Gln Asp Gly His Leu
370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Gln Gly Gly Asn Ser Asn
                405                 410                 415

Gly Ala Leu Cys His Phe Pro Phe Leu Tyr Asn Asn His Asn Tyr Thr
                420                 425                 430

Asp Cys Thr Ser Glu Gly Arg Arg Asp Asn Met Lys Trp Cys Gly Thr
            435                 440                 445

Thr Gln Asn Tyr Asp Ala Asp Gln Lys Phe Gly Phe Cys Pro Met Ala
450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
            515                 520                 525

Asp Thr Phe His Lys Arg His Glu Glu Gly His Met Leu Asn Cys Thr
530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
            595                 600                 605

Ser Gly Pro Val Glu Val Phe Ile Thr Glu Thr Pro Ser Gln Pro Asn
610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
            660                 665                 670

Pro Gly Val Val Tyr Glu Gly Gln Leu Ile Ser Ile Gln Gln Tyr Gly
            675                 680                 685

His Gln Glu Val Thr Arg Phe Asp Phe Thr Thr Ser Thr Ser Thr
690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
            740                 745                 750

Glu Tyr Glu Leu Ser Glu Glu Gly Asp Glu Pro Gln Tyr Leu Asp Leu
            755                 760                 765

Pro Ser Thr Ala Thr Ser Val Asn Ile Pro Asp Leu Leu Pro Gly Arg
770                 775                 780
```

```
Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Pro Thr Val Asp Gln Val Asp Asp Thr Ser Ile Val Val Arg Trp Ser
                820                 825                 830

Arg Pro Gln Ala Pro Ile Thr Gly Tyr Arg Ile Val Tyr Ser Pro Ser
                835                 840                 845

Val Glu Gly Ser Ser Thr Glu Leu Asn Leu Pro Glu Thr Ala Asn Ser
850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
                900                 905                 910

Leu Gln Phe Val Glu Val Thr Asp Val Lys Val Thr Ile Met Trp Thr
                915                 920                 925

Pro Pro Glu Ser Ala Val Thr Gly Tyr Arg Val Asp Val Ile Pro Val
930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
                980                 985                 990

Gln Thr Thr Lys Leu Asp Ala Pro Thr Asn Leu Gln Phe Val Asn Glu
                995                 1000                1005

Thr Asp Ser Thr Val Leu Val Arg Trp Thr Pro Pro Arg Ala Gln
    1010                1015                1020

Ile Thr Gly Tyr Arg Leu Thr Val Gly Leu Thr Arg Arg Gly Gln
    1025                1030                1035

Pro Arg Gln Tyr Asn Val Gly Pro Ser Val Ser Lys Tyr Pro Leu
    1040                1045                1050

Arg Asn Leu Gln Pro Ala Ser Glu Tyr Thr Val Ser Leu Val Ala
    1055                1060                1065

Ile Lys Gly Asn Gln Glu Ser Pro Lys Ala Thr Gly Val Phe Thr
    1070                1075                1080

Thr Leu Gln Pro Gly Ser Ser Ile Pro Pro Tyr Asn Thr Glu Val
    1085                1090                1095

Thr Glu Thr Thr Ile Val Ile Thr Trp Thr Pro Ala Pro Arg Ile
    1100                1105                1110

Gly Phe Lys Leu Gly Val Arg Pro Ser Gln Gly Gly Glu Ala Pro
    1115                1120                1125

Arg Glu Val Thr Ser Asp Ser Gly Ser Ile Val Val Ser Gly Leu
    1130                1135                1140

Thr Pro Gly Val Glu Tyr Val Tyr Thr Ile Gln Val Leu Arg Asp
    1145                1150                1155

Gly Gln Glu Arg Asp Ala Pro Ile Val Asn Lys Val Val Thr Pro
    1160                1165                1170

Leu Ser Pro Pro Thr Asn Leu His Leu Glu Ala Asn Pro Asp Thr
    1175                1180                1185
```

```
Gly Val Leu Thr Val Ser Trp Glu Arg Ser Thr Thr Pro Asp Ile
    1190            1195                1200

Thr Gly Tyr Arg Ile Thr Thr Pro Thr Asn Gly Gln Gln Gly
1205            1210                1215

Asn Ser Leu Glu Glu Val Val His Ala Asp Gln Ser Ser Cys Thr
    1220            1225                1230

Phe Asp Asn Leu Ser Pro Gly Leu Glu Tyr Asn Val Ser Val Tyr
    1235            1240                1245

Thr Val Lys Asp Asp Lys Glu Ser Val Pro Ile Ser Asp Thr Ile
    1250            1255                1260

Ile Pro Ala Val Pro Pro Thr Asp Leu Arg Phe Thr Asn Ile
    1265            1270                1275

Gly Pro Asp Thr Met Arg Val Thr Trp Ala Pro Pro Ser Ile
    1280            1285                1290

Asp Leu Thr Asn Phe Leu Val Arg Tyr Ser Pro Val Lys Asn Glu
    1295            1300                1305

Glu Asp Val Ala Glu Leu Ser Ile Ser Pro Ser Asp Asn Ala Val
    1310            1315                1320

Val Leu Thr Asn Leu Leu Pro Gly Thr Glu Tyr Val Val Ser Val
    1325            1330                1335

Ser Ser Val Tyr Glu Gln His Glu Ser Thr Pro Leu Arg Gly Arg
    1340            1345                1350

Gln Lys Thr Gly Leu Asp Ser Pro Thr Gly Ile Asp Phe Ser Asp
    1355            1360                1365

Ile Thr Ala Asn Ser Phe Thr Val His Trp Ile Ala Pro Arg Ala
    1370            1375                1380

Thr Ile Thr Gly Tyr Arg Ile Arg His His Pro Glu His Phe Ser
    1385            1390                1395

Gly Arg Pro Arg Glu Asp Arg Val Pro His Ser Arg Asn Ser Ile
    1400            1405                1410

Thr Leu Thr Asn Leu Thr Pro Gly Thr Glu Tyr Val Val Ser Ile
    1415            1420                1425

Val Ala Leu Asn Gly Arg Glu Glu Ser Pro Leu Leu Ile Gly Gln
    1430            1435                1440

Gln Ser Thr Val Ser Asp Val Pro Arg Asp Leu Glu Val Val Ala
    1445            1450                1455

Ala Thr Pro Thr Ser Leu Leu Ile Ser Trp Asp Ala Pro Ala Val
    1460            1465                1470

Thr Val Arg Tyr Tyr Arg Ile Thr Tyr Gly Glu Thr Gly Gly Asn
    1475            1480                1485

Ser Pro Val Gln Glu Phe Thr Val Pro Gly Ser Lys Ser Thr Ala
    1490            1495                1500

Thr Ile Ser Gly Leu Lys Pro Gly Val Asp Tyr Thr Ile Thr Val
    1505            1510                1515

Tyr Ala Val Thr Gly Arg Gly Asp Ser Pro Ala Ser Ser Lys Pro
    1520            1525                1530

Ile Ser Ile Asn Tyr Arg Thr Glu Ile Asp Lys Pro Ser Gln Met
    1535            1540                1545

Gln Val Thr Asp Val Gln Asp Asn Ser Ile Ser Val Lys Trp Leu
    1550            1555                1560

Pro Ser Ser Ser Pro Val Thr Gly Tyr Arg Val Thr Thr Thr Pro
    1565            1570                1575

Lys Asn Gly Pro Gly Pro Thr Lys Thr Lys Thr Ala Gly Pro Asp
```

```
                    1580                1585                1590

Gln  Thr  Glu  Met  Thr  Ile  Glu  Gly  Leu  Gln  Pro  Thr  Val  Glu  Tyr
     1595                1600                1605

Val  Val  Ser  Val  Tyr  Ala  Gln  Asn  Pro  Ser  Gly  Glu  Ser  Gln  Pro
     1610                1615                1620

Leu  Val  Gln  Thr  Ala  Val  Thr  Asn  Ile  Asp  Arg  Pro  Lys  Gly  Leu
     1625                1630                1635

Ala  Phe  Thr  Asp  Val  Asp  Val  Asp  Ser  Ile  Lys  Ile  Ala  Trp  Glu
     1640                1645                1650

Ser  Pro  Gln  Gly  Gln  Val  Ser  Arg  Tyr  Arg  Val  Thr  Tyr  Ser  Ser
     1655                1660                1665

Pro  Glu  Asp  Gly  Ile  His  Glu  Leu  Phe  Pro  Ala  Pro  Asp  Gly  Glu
     1670                1675                1680

Glu  Asp  Thr  Ala  Glu  Leu  Gln  Gly  Leu  Arg  Pro  Gly  Ser  Glu  Tyr
     1685                1690                1695

Thr  Val  Ser  Val  Val  Ala  Leu  His  Asp  Asp  Met  Glu  Ser  Gln  Pro
     1700                1705                1710

Leu  Ile  Gly  Thr  Gln  Ser  Thr  Ala  Ile  Pro  Ala  Pro  Thr  Asp  Leu
     1715                1720                1725

Lys  Phe  Thr  Gln  Val  Thr  Pro  Thr  Ser  Leu  Ser  Ala  Gln  Trp  Thr
     1730                1735                1740

Pro  Pro  Asn  Val  Gln  Leu  Thr  Gly  Tyr  Arg  Val  Arg  Val  Thr  Pro
     1745                1750                1755

Lys  Glu  Lys  Thr  Gly  Pro  Met  Lys  Glu  Ile  Asn  Leu  Ala  Pro  Asp
     1760                1765                1770

Ser  Ser  Ser  Val  Val  Ser  Gly  Leu  Met  Val  Ala  Thr  Lys  Tyr
     1775                1780                1785

Glu  Val  Ser  Val  Tyr  Ala  Leu  Lys  Asp  Thr  Leu  Thr  Ser  Arg  Pro
     1790                1795                1800

Ala  Gln  Gly  Val  Val  Thr  Thr  Leu  Glu  Asn  Val  Ser  Pro  Pro  Arg
     1805                1810                1815

Arg  Ala  Arg  Val  Thr  Asp  Ala  Thr  Glu  Thr  Thr  Ile  Thr  Ile  Ser
     1820                1825                1830

Trp  Arg  Thr  Lys  Thr  Glu  Thr  Ile  Thr  Gly  Phe  Gln  Val  Asp  Ala
     1835                1840                1845

Val  Pro  Ala  Asn  Gly  Gln  Thr  Pro  Ile  Gln  Arg  Thr  Ile  Lys  Pro
     1850                1855                1860

Asp  Val  Arg  Ser  Tyr  Thr  Ile  Thr  Gly  Leu  Gln  Pro  Gly  Thr  Asp
     1865                1870                1875

Tyr  Lys  Ile  Tyr  Leu  Tyr  Thr  Leu  Asn  Asp  Asn  Ala  Arg  Ser  Ser
     1880                1885                1890

Pro  Val  Val  Ile  Asp  Ala  Ser  Thr  Ala  Ile  Asp  Ala  Pro  Ser  Asn
     1895                1900                1905

Leu  Arg  Phe  Leu  Ala  Thr  Thr  Pro  Asn  Ser  Leu  Leu  Val  Ser  Trp
     1910                1915                1920

Gln  Pro  Pro  Arg  Ala  Arg  Ile  Thr  Gly  Tyr  Ile  Ile  Lys  Tyr  Glu
     1925                1930                1935

Lys  Pro  Gly  Ser  Pro  Pro  Arg  Glu  Val  Val  Pro  Arg  Pro  Arg  Pro
     1940                1945                1950

Gly  Val  Thr  Glu  Ala  Thr  Ile  Thr  Gly  Leu  Glu  Pro  Gly  Thr  Glu
     1955                1960                1965

Tyr  Thr  Ile  Tyr  Val  Ile  Ala  Leu  Lys  Asn  Asn  Gln  Lys  Ser  Glu
     1970                1975                1980
```

```
Pro Leu Ile Gly Arg Lys Lys Thr Asp Glu Leu Pro Gln Leu Val
    1985            1990                1995

Thr Leu Pro His Pro Asn Leu His Gly Pro Glu Ile Leu Asp Val
    2000            2005                2010

Pro Ser Thr Val Gln Lys Thr Pro Phe Val Thr His Pro Gly Tyr
    2015            2020                2025

Asp Thr Gly Asn Gly Ile Gln Leu Pro Gly Thr Ser Gly Gln Gln
    2030            2035                2040

Pro Ser Val Gly Gln Gln Met Ile Phe Glu Glu His Gly Phe Arg
    2045            2050                2055

Arg Thr Thr Pro Pro Thr Thr Ala Thr Pro Ile Arg His Arg Pro
    2060            2065                2070

Arg Pro Tyr Pro Pro Asn Val Gly Glu Glu Ile Gln Ile Gly His
    2075            2080                2085

Ile Pro Arg Glu Asp Val Asp Tyr His Leu Tyr Pro His Gly Pro
    2090            2095                2100

Gly Leu Asn Pro Asn Ala Ser Thr Gly Gln Glu Ala Leu Ser Gln
    2105            2110                2115

Thr Thr Ile Ser Trp Ala Pro Phe Gln Asp Thr Ser Glu Tyr Ile
    2120            2125                2130

Ile Ser Cys His Pro Val Gly Thr Asp Glu Glu Pro Leu Gln Phe
    2135            2140                2145

Arg Val Pro Gly Thr Ser Thr Ser Ala Thr Leu Thr Gly Leu Thr
    2150            2155                2160

Arg Gly Ala Thr Tyr Asn Ile Ile Val Glu Ala Leu Lys Asp Gln
    2165            2170                2175

Gln Arg His Lys Val Arg Glu Glu Val Val Thr Val Gly Asn Ser
    2180            2185                2190

Val Asn Glu Gly Leu Asn Gln Pro Thr Asp Asp Ser Cys Phe Asp
    2195            2200                2205

Pro Tyr Thr Val Ser His Tyr Ala Val Gly Asp Glu Trp Glu Arg
    2210            2215                2220

Met Ser Glu Ser Gly Phe Lys Leu Leu Cys Gln Cys Leu Gly Phe
    2225            2230                2235

Gly Ser Gly His Phe Arg Cys Asp Ser Ser Arg Trp Cys His Asp
    2240            2245                2250

Asn Gly Val Asn Tyr Lys Ile Gly Glu Lys Trp Asp Arg Gln Gly
    2255            2260                2265

Glu Asn Gly Gln Met Met Ser Cys Thr Cys Leu Gly Asn Gly Lys
    2270            2275                2280

Gly Glu Phe Lys Cys Asp Pro His Glu Ala Thr Cys Tyr Asp Asp
    2285            2290                2295

Gly Lys Thr Tyr His Val Gly Glu Gln Trp Gln Lys Glu Tyr Leu
    2300            2305                2310

Gly Ala Ile Cys Ser Cys Thr Cys Phe Gly Gly Gln Arg Gly Trp
    2315            2320                2325

Arg Cys Asp Asn Cys Arg Arg Pro Gly Gly Glu Pro Ser Pro Glu
    2330            2335                2340

Gly Thr Thr Gly Gln Ser Tyr Asn Gln Tyr Ser Gln Arg Tyr His
    2345            2350                2355

Gln Arg Thr Asn Thr Asn Val Asn Cys Pro Ile Glu Cys Phe Met
    2360            2365                2370
```

```
Pro Leu Asp Val Gln Ala Asp Arg Glu Asp Ser Arg Glu
    2375                2380                2385
```

<210> SEQ ID NO 2
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Gln Trp Asn Ala Pro Gln Ser His Ile Ser Lys Tyr Ile Leu Arg
1               5                   10                  15

Trp Arg Pro Lys Asn Ser Val Gly Arg Trp Lys Glu Ala Thr Ile Pro
                20                  25                  30

Gly His Leu Asn Ser Tyr Thr Ile Lys Gly Leu Lys Pro Gly Val Val
            35                  40                  45

Tyr Glu Gly Gln Leu Ile Ser Ile Gln Gln Tyr Gly His Gln Glu Val
        50                  55                  60

Thr Arg Phe Asp Phe Thr Thr Thr Ser Thr Ser Thr
65                  70                  75
```

<210> SEQ ID NO 3
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

```
Gln Pro Ser His Ile Ser Lys Tyr Ile Leu Arg Trp Arg Pro Lys Asn
1               5                   10                  15

Ser Val Gly Arg Trp Lys Glu Ala Thr
                20                  25
```

<210> SEQ ID NO 4
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

```
Gln Leu Ile Ser Ile Gln Gln Tyr Gly His Gln Glu Val Thr Arg Phe
1               5                   10                  15

Asp Phe Thr Thr Thr Ser Thr Ser Thr
                20                  25
```

<210> SEQ ID NO 5
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

```
Asn Gly Gln Thr Pro Ile Gln Arg Thr Ile Lys Pro Asp Val Arg Ser
1               5                   10                  15

Tyr Thr Ile Thr Gly Leu Gln Pro Gly Thr
                20                  25
```

```
<210> SEQ ID NO 6
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Pro Ser Val Gly Gln Gln Met Ile Phe Glu Glu His Gly Phe Arg
1               5                   10                  15

Arg Thr Thr Pro Pro Thr Thr Ala Thr
            20                  25

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Pro Ser His Ile Ser Lys Tyr Ile Leu Arg Trp Arg Pro Lys
1               5                   10                  15

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ile Leu Arg Trp Arg Pro Lys Asn Ser Val Gly Arg Trp Lys
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Pro Ser His Ile Ser Lys Tyr Ile Leu Arg Trp Arg Pro Lys
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Pro Ser Leu Ala Lys Lys Gln Arg Phe Arg His Arg Asn Arg
1               5                   10

<210> SEQ ID NO 11
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 11

Cys Cys Val Arg Gln Leu Tyr Ile Asp Phe Arg Lys Asp Leu Gly
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Lys Thr Arg Thr Glu Val Phe Glu Ile Ser Arg Arg Leu Ile
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Cys Glu Cys Arg Pro Lys Lys Asp Arg Ala Arg Lys Glu Asn Pro
1               5                   10                  15

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Ser His His His His His His Cys
1               5

<210> SEQ ID NO 15
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Lys Lys Gln Leu Ile Ser Ile Gln Gln Tyr Gly His Gln Glu Val
1               5                   10                  15

Thr Arg Phe Asp Phe Thr Thr Thr Ser Thr Ser Thr
                20                  25

<210> SEQ ID NO 16
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16
```

Gln Leu Ile Ser Ile Gln Gln Tyr Gly His Gln Glu Val Thr Arg Phe
1               5                   10                  15

Asp Phe Thr Thr Thr Ser Thr Ser Thr Lys Lys Lys
            20                  25

<210> SEQ ID NO 17
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Pro Ser His Ile Ser Lys Tyr Ile Leu Arg Trp Arg Pro Lys Asn
1               5                   10                  15

Ser Val Gly Arg Trp Lys Glu Ala Thr
            20                  25

<210> SEQ ID NO 18
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Leu Ile Ser Ile Gln Gln Tyr Gly His Gln Glu Val Thr Arg Phe
1               5                   10                  15

Asp Phe Thr Thr Thr Ser Thr Ser Thr
            20                  25

<210> SEQ ID NO 19
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asn Gly Gln Thr Pro Ile Gln Arg Thr Ile Lys Pro Asp Val Arg Ser
1               5                   10                  15

Tyr Thr Ile Thr Gly Leu Gln Pro Gly Thr
            20                  25

<210> SEQ ID NO 20
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Pro Ser Val Gly Gln Gln Met Ile Phe Glu Glu His Gly Phe Arg
1               5                   10                  15

Arg Thr Thr Pro Pro Thr Thr Ala Thr
            20                  25

<210> SEQ ID NO 21
<211> LENGTH: 15
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 21

Gln Pro Ser His Ile Ser Lys Tyr Ile Leu Arg Trp Arg Pro Lys
1               5                   10                  15

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ile Leu Arg Trp Arg Pro Lys Asn Ser Val Gly Arg Trp Lys
1               5                   10

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Pro Ser His Ile Ser Lys Tyr
1               5

<210> SEQ ID NO 24
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Trp Asn Ala Pro Gln Pro Ser His Ile Ser Lys Tyr Ile Leu Arg Trp
1               5                   10                  15

Arg Pro Lys

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Pro Ser His Ile Ser Lys Tyr Ile Leu Arg Trp Arg Pro Lys
1               5                   10                  15

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Pro Ser His Ile Ser Lys Tyr
```

```
<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Tyr Ile Leu Arg Trp Arg Pro Lys Asn Ser Val Gly Arg Trp
1               5                   10

<210> SEQ ID NO 28
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys Asn Ser Val Gly Arg Trp Lys Glu Ala Thr Ile Pro Gly His Leu
1               5                   10                  15

Asn Ser Tyr Thr
            20

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Cys Cys Val Arg Gln Leu Tyr Ile Asp Phe Arg Lys Asp Leu Gly
1               5                   10                  15

<210> SEQ ID NO 30
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln or Asn
<220> FEATURE:
<221> NAME/KEY: MOD_RES
<222> LOCATION: (2)..(3)
<223> OTHER INFORMATION: Any amino acid and this region may encompass
      1 to 2 residues
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (5)..(5)
<223> OTHER INFORMATION: Any amino acid or absent
<220> FEATURE:
<221> NAME/KEY: MOD_RES
<222> LOCATION: (6)..(6)
<223> OTHER INFORMATION: Ile or Gly
<220> FEATURE:
<221> NAME/KEY: MOD_RES
<222> LOCATION: (7)..(7)
```

```
<223> OTHER INFORMATION: Gln or Ser
<220> FEATURE:
<221> NAME/KEY: MOD_RES
<222> LOCATION: (8)..(8)
<223> OTHER INFORMATION: Lys, Arg or Gln
<220> FEATURE:
<221> NAME/KEY: MOD_RES
<222> LOCATION: (9)..(9)
<223> OTHER INFORMATION: Tyr, Thr or Met
<220> FEATURE:
<221> NAME/KEY: MOD_RES
<222> LOCATION: (10)..(10)
<223> OTHER INFORMATION: Ile or Gly
<220> FEATURE:
<221> NAME/KEY: MOD_RES
<222> LOCATION: (11)..(15)
<223> OTHER INFORMATION: Any amino acid and this region may encompass
     4 to 5 residues
<220> FEATURE:
<221> NAME/KEY: MOD_RES
<222> LOCATION: (16)..(16)
<223> OTHER INFORMATION: Any amino acid or absent
<220> FEATURE:
<221> NAME/KEY: MOD_RES
<222> LOCATION: (17)..(17)
<223> OTHER INFORMATION: Lys or Arg
<220> FEATURE:
<221> NAME/KEY: MOD_RES
<222> LOCATION: (18)..(19)
<223> OTHER INFORMATION: Any amino acid and this region may encompass
     1 to 2 residues
<220> FEATURE:
<221> NAME/KEY: MOD_RES
<222> LOCATION: (20)..(21)
<223> OTHER INFORMATION: Any amino acid and this region may encompass
     1 to 2 residues
<220> FEATURE:
<221> NAME/KEY: MOD_RES
<222> LOCATION: (22)..(22)
<223> OTHER INFORMATION: Arg or Thr
<220> FEATURE:
<221> NAME/KEY: MOD_RES
<222> LOCATION: (23)..(24)
<223> OTHER INFORMATION: Any amino acid and this region may encompass
     1 to 2 residues
<220> FEATURE:
<221> NAME/KEY: MOD_RES
<222> LOCATION: (25)..(25)
<223> OTHER INFORMATION: Lys, Gln, Thr or Ser
<220> FEATURE:
<221> NAME/KEY: MOD_RES
<222> LOCATION: (26)..(27)
<223> OTHER INFORMATION: Any amino acid

<400> SEQUENCE: 30

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Thr
            20                  25

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 31

Cys Ala Asn Arg Tyr Leu Ala Met Lys Glu Asp Gly Arg Leu Leu
1               5                   10                  15

<210> SEQ ID NO 32
```

```
<400> SEQUENCE: 32

000

<210> SEQ ID NO 33
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Pro Ser His Ile Ser Lys Tyr Ile Leu Arg Trp Arg Pro Lys Asn
1               5                   10                  15

Ser Val Gly Arg Trp Lys Glu Ala Thr
            20                  25

<210> SEQ ID NO 34
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Leu Ile Ser Ile Gln Gln Tyr Gly His Gln Glu Val Thr Arg Phe
1               5                   10                  15

Asp Phe Thr Thr Thr Ser Thr Ser Thr
            20                  25

<210> SEQ ID NO 35
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asn Gly Gln Thr Pro Ile Gln Arg Thr Ile Lys Pro Asp Val Arg Ser
1               5                   10                  15

Tyr Thr Ile Thr Gly Leu Gln Pro Gly Thr
            20                  25

<210> SEQ ID NO 36
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Pro Ser Val Gly Gln Gln Met Ile Phe Glu Glu His Gly Phe Arg
1               5                   10                  15

Arg Thr Thr Pro Pro Thr Thr Ala Thr
            20                  25

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 37

Gln Pro Ser His Ile Ser Lys Tyr Ile Leu Arg Trp Arg Pro Lys
1               5                   10                  15

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Pro Ser His Ile Ser Lys Tyr Ile Leu Arg Trp Arg Pro Lys
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ser His Ile Ser Lys Tyr Ile Leu Arg Trp Arg Pro Lys
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

His Ile Ser Lys Tyr Ile Leu Arg Trp Arg Pro Lys
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ile Ser Lys Tyr Ile Leu Arg Trp Arg Pro Lys
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser Lys Tyr Ile Leu Arg Trp Arg Pro Lys
1               5                   10

<210> SEQ ID NO 43

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Lys Tyr Ile Leu Arg Trp Arg Pro Lys
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Tyr Ile Leu Arg Trp Arg Pro Lys
1               5

<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Pro Ser His Ile Ser Lys Tyr Ile Leu Arg Trp Arg Pro
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Pro Ser His Ile Ser Lys Tyr Ile Leu Arg Trp Arg
1               5                   10

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Pro Ser His Ile Ser Lys Tyr Ile Leu Arg Trp
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48
```

Pro Ser His Ile Ser Lys Tyr Ile Leu Arg
1               5                   10

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Pro Ser His Ile Ser Lys Tyr Ile Leu
1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Pro Ser His Ile Ser Lys Tyr Ile
1               5

<210> SEQ ID NO 51
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Pro Ser Leu Ala Lys Lys Gln Arg Phe Arg His Arg Asn Arg
1               5                   10

<210> SEQ ID NO 52
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Pro Ser Leu Ala Lys Lys Gln Arg Phe Arg His Arg Asn Arg
1               5                   10

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Pro Ser His Ile Ser Lys Tyr Ile Leu Arg Trp Arg Pro Lys
1               5                   10

<210> SEQ ID NO 54
<211> LENGTH: 14
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 54

Pro Ser His Ile Ser Lys Tyr Ile Leu Arg Trp Arg Pro Lys
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Pro Ser His Ile Ser Lys Tyr Ile Leu Arg Trp Arg Pro Lys
1               5                   10

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pro or any non polar amino acid
<220> FEATURE:
<221> NAME/KEY: MOD_RES
<222> LOCATION: (2)..(9)
<223> OTHER INFORMATION: Any amino acid and this region may encompass
      0 to 8 residues
<220> FEATURE:
<221> NAME/KEY: MOD_RES
<222> LOCATION: (10)..(10)
<223> OTHER INFORMATION: Lys or Arg
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (12)..(12)
<223> OTHER INFORMATION: Lys or Arg
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (14)..(14)
<223> OTHER INFORMATION: Lys or Arg

<400> SEQUENCE: 56

Xaa Xaa Xaa Xaa Xaa Xaa Xaa Xaa Xaa Xaa Xaa Xaa Xaa Xaa
1               5                   10

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ser His Ile Ser Lys Tyr Ile Leu
1               5
```

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ser Leu Ala Lys Lys Gln Arg Phe
1               5

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Trp Arg Pro Lys
1               5

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Arg His Arg Asn Arg
1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Pro Ser His Ile Ser Lys Tyr Leu
1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Pro Ser Leu Ala Lys Lys Gln Arg Phe
1               5

<210> SEQ ID NO 63
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 63

Pro Ser His Ile Ser Lys Tyr Ile Leu Arg Trp Arg Pro Lys
1               5                   10

<210> SEQ ID NO 64
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Pro Ser Leu Ala Lys Lys Gln Arg Phe Arg His Arg Asn Arg
1               5                   10

<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Pro Ser His Ile Ser Lys Tyr Ile Leu Arg Trp Arg Pro Lys
1               5                   10                  15

<210> SEQ ID NO 66
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Pro Ser His Ile Ser Lys Tyr Ile Leu Arg Trp Arg Pro Lys Asn
1               5                   10                  15

Ser Val Gly Arg Trp Lys Glu Ala Thr
            20                  25

<210> SEQ ID NO 67
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Leu Ile Ser Ile Gln Gln Tyr Gly His Gln Glu Val Thr Arg Phe
1               5                   10                  15

Asp Phe Thr Thr Thr Ser Thr Ser Thr
            20                  25

<210> SEQ ID NO 68
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asn Gly Gln Thr Pro Ile Gln Arg Thr Ile Lys Pro Asp Val Arg Ser
```

```
                1               5                      10                     15
Tyr Thr Ile Thr Gly Leu Gln Pro Gly Thr
                         20                     25

<210> SEQ ID NO 69
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln Pro Ser Val Gly Gln Gln Met Ile Phe Glu Glu His Gly Phe Arg
1               5                   10                  15

Arg Thr Thr Pro Pro Thr Thr Ala Thr
                20                  25

<210> SEQ ID NO 70
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Cys, Asn, Thr or Val
<220> FEATURE:
<221> NAME/KEY: MOD_RES
<222> LOCATION: (5)..(8)
<223> OTHER INFORMATION: Any amino acid
<220> FEATURE:
<221> NAME/KEY: MOD_RES
<222> LOCATION: (9)..(9)
<223> OTHER INFORMATION: Asp, Glu, Lys or Arg
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(11)
<223> OTHER INFORMATION: Asp, Arg or Ser
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (13)..(13)
<223> OTHER INFORMATION: Asp, Glu or Arg
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (15)..(15)
<223> OTHER INFORMATION: Gly, Ile, Leu or Pro

<400> SEQUENCE: 70

Cys Xaa Xaa Arg Xaa Xaa Xaa Xaa Xaa Xaa Xaa Xaa Xaa Xaa Xaa
1               5                   10                  15

<210> SEQ ID NO 71
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Thr Ser His His His His His His Cys
1               5

<210> SEQ ID NO 72
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln or Asn
<220> FEATURE:
<221> NAME/KEY: MOD_RES
<222> LOCATION: (2)..(3)
<223> OTHER INFORMATION: Any amino acid and this region may encompass
      1 to 2 residues
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (5)..(5)
<223> OTHER INFORMATION: Any amino acid or absent
<220> FEATURE:
<221> NAME/KEY: MOD_RES
<222> LOCATION: (6)..(6)
<223> OTHER INFORMATION: Ile or Gly
<220> FEATURE:
<221> NAME/KEY: MOD_RES
<222> LOCATION: (7)..(7)
<223> OTHER INFORMATION: Ser or Gln
<220> FEATURE:
<221> NAME/KEY: MOD_RES
<222> LOCATION: (8)..(8)
<223> OTHER INFORMATION: Lys, Arg or Gln
<220> FEATURE:
<221> NAME/KEY: MOD_RES
<222> LOCATION: (9)..(9)
<223> OTHER INFORMATION: Tyr, Thr or Met
<220> FEATURE:
<221> NAME/KEY: MOD_RES
<222> LOCATION: (10)..(10)
<223> OTHER INFORMATION: Ile or Gly
<220> FEATURE:
<221> NAME/KEY: MOD_RES
<222> LOCATION: (11)..(15)
<223> OTHER INFORMATION: Any amino acid and this region may encompass
      4 to 5 residues
<220> FEATURE:
<221> NAME/KEY: MOD_RES
<222> LOCATION: (16)..(16)
<223> OTHER INFORMATION: Any amino acid or absent
<220> FEATURE:
<221> NAME/KEY: MOD_RES
<222> LOCATION: (17)..(17)
<223> OTHER INFORMATION: Lys or Arg
<220> FEATURE:
<221> NAME/KEY: MOD_RES
<222> LOCATION: (18)..(19)
<223> OTHER INFORMATION: Any amino acid and this region may encompass
      1 to 2 residues
<220> FEATURE:
<221> NAME/KEY: MOD_RES
<222> LOCATION: (20)..(21)
<223> OTHER INFORMATION: Any amino acid and this region may encompass
      1 to 2 residues
```

```
<220> FEATURE:
<221> NAME/KEY: MOD_RES
<222> LOCATION: (22)..(22)
<223> OTHER INFORMATION: Arg or Thr
<220> FEATURE:
<221> NAME/KEY: MOD_RES
<222> LOCATION: (23)..(24)
<223> OTHER INFORMATION: Any amino acid and this region may encompass
      1 to 2 residues
<220> FEATURE:
<221> NAME/KEY: MOD_RES
<222> LOCATION: (25)..(25)
<223> OTHER INFORMATION: Lys, Gln, Thr or Ser
<220> FEATURE:
<221> NAME/KEY: MOD_RES
<222> LOCATION: (26)..(27)
<223> OTHER INFORMATION: Any amino acid
<220> FEATURE:
<223> OTHER INFORMATION: See specification as filed for detailed
      description of substitutions and preferred embodiments

<400> SEQUENCE: 72

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Thr
            20                  25

<210> SEQ ID NO 73
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln or Asn
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Ile or Gly
<220> FEATURE:
<221> NAME/KEY: MOD_RES
<222> LOCATION: (6)..(6)
<223> OTHER INFORMATION: Ser or Gln
<220> FEATURE:
<221> NAME/KEY: MOD_RES
<222> LOCATION: (7)..(7)
<223> OTHER INFORMATION: Lys, Arg or Gln
<220> FEATURE:
<221> NAME/KEY: MOD_RES
<222> LOCATION: (8)..(8)
<223> OTHER INFORMATION: Tyr, Thr or Met
<220> FEATURE:
<221> NAME/KEY: MOD_RES
<222> LOCATION: (9)..(9)
<223> OTHER INFORMATION: Ile or Gly
<220> FEATURE:
<221> NAME/KEY: MOD_RES
<222> LOCATION: (10)..(14)
<223> OTHER INFORMATION: Any amino acid
<220> FEATURE:
<221> NAME/KEY: MOD_RES
```

```
<222> LOCATION: (15)..(15)
<223> OTHER INFORMATION: Lys or Arg
<220> FEATURE:
<223> OTHER INFORMATION: See specification as filed for detailed
      description of substitutions and preferred embodiments

<400> SEQUENCE: 73

Xaa Xaa Xaa Xaa Xaa Xaa Xaa Xaa Xaa Xaa Xaa Xaa Xaa Xaa Xaa
1               5                   10                  15

<210> SEQ ID NO 74
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ile or Gly
<220> FEATURE:
<221> NAME/KEY: MOD_RES
<222> LOCATION: (2)..(6)
<223> OTHER INFORMATION: Any amino acid and this region may encompass
      4 to 5 residues
<220> FEATURE:
<221> NAME/KEY: MOD_RES
<222> LOCATION: (7)..(7)
<223> OTHER INFORMATION: Any amino acid or absent
<220> FEATURE:
<221> NAME/KEY: MOD_RES
<222> LOCATION: (8)..(8)
<223> OTHER INFORMATION: Lys or Arg
<220> FEATURE:
<221> NAME/KEY: MOD_RES
<222> LOCATION: (9)..(10)
<223> OTHER INFORMATION: Any amino acid and this region may encompass
      1 to 2 residues
<220> FEATURE:
<221> NAME/KEY: MOD_RES
<222> LOCATION: (11)..(12)
<223> OTHER INFORMATION: Any amino acid and this region may encompass
      1 to 2 residues
<220> FEATURE:
<221> NAME/KEY: MOD_RES
<222> LOCATION: (13)..(13)
<223> OTHER INFORMATION: Arg or Thr
<220> FEATURE:
<221> NAME/KEY: MOD_RES
<222> LOCATION: (14)..(15)
<223> OTHER INFORMATION: Any amino acid and this region may encompass
      1 to 2 residues
<220> FEATURE:
<221> NAME/KEY: MOD_RES
<222> LOCATION: (16)..(16)
<223> OTHER INFORMATION: Lys, Gln, Thr or Ser
<220> FEATURE:
<223> OTHER INFORMATION: See specification as filed for detailed
      description of substitutions and preferred embodiments

<400> SEQUENCE: 74

Xaa Xaa Xaa Xaa Xaa Xaa Xaa Xaa Xaa Xaa Xaa Xaa Xaa Xaa Xaa Xaa
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
```

```
<223> OTHER INFORMATION: Any amino acid
<220> FEATURE:
<221> NAME/KEY: MOD_RES
<222> LOCATION: (3)..(3)
<223> OTHER INFORMATION: Any uncharged amino acid residue
<220> FEATURE:
<221> NAME/KEY: MOD_RES
<222> LOCATION: (5)..(8)
<223> OTHER INFORMATION: Any amino acid
<220> FEATURE:
<221> NAME/KEY: MOD_RES
<222> LOCATION: (9)..(9)
<223> OTHER INFORMATION: Any charged amino acid residue
<220> FEATURE:
<221> NAME/KEY: MOD_RES
<222> LOCATION: (10)..(12)
<223> OTHER INFORMATION: Any amino acid
<220> FEATURE:
<221> NAME/KEY: MOD_RES
<222> LOCATION: (13)..(13)
<223> OTHER INFORMATION: Any charged amino acid residue
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (15)..(15)
<223> OTHER INFORMATION: Any non polar amino acid residue
<220> FEATURE:
<223> OTHER INFORMATION: See specification as filed for detailed
      description of substitutions and preferred embodiments

<400> SEQUENCE: 75

Cys Xaa Xaa Arg Xaa Xaa Xaa Xaa Xaa Xaa Xaa Xaa Xaa Xaa Xaa
1               5                   10                  15

<210> SEQ ID NO 76
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Leu Arg Trp Arg
1

<210> SEQ ID NO 77
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Leu Arg Trp Arg Pro
1               5

<210> SEQ ID NO 78
<211> LENGTH: 389
<212> TYPE: PRT
<213> ORGANISM: Homo sapiens

<400> SEQUENCE: 78

Met Pro Pro Ser Gly Leu Arg Leu Leu Pro Leu Leu Leu Pro Leu Leu
1               5                   10                  15

Trp Leu Leu Val Leu Thr Pro Gly Arg Pro Ala Ala Gly Leu Ser Thr
            20                  25                  30
```

Cys Lys Thr Ile Asp Met Glu Leu Val Lys Arg Lys Arg Ile Glu Ala
                35                  40                  45

Ile Arg Gly Gln Ile Leu Ser Lys Leu Arg Leu Ala Pro Pro Ser Gln
    50                  55                  60

Gly Glu Val Pro Pro Gly Pro Leu Pro Glu Ala Val Leu Ala Leu Tyr
65                  70                  75                  80

Asn Ser Thr Arg Asp Arg Val Ala Gly Glu Ser Ala Glu Pro Glu Pro
                85                  90                  95

Glu Pro Glu Ala Asp Tyr Tyr Ala Lys Glu Val Thr Arg Val Leu Met
                100                 105                 110

Val Glu Thr His Asn Glu Ile Tyr Asp Lys Phe Lys Gln Ser Thr His
                115                 120                 125

Ser Ile Tyr Met Phe Phe Asn Thr Ser Glu Leu Arg Glu Ala Val Pro
            130                 135                 140

Glu Pro Val Leu Leu Ser Arg Ala Glu Leu Arg Leu Leu Arg Leu Lys
145                 150                 155                 160

Leu Lys Val Glu Gln His Val Glu Leu Tyr Gln Lys Tyr Ser Asn Asn
                165                 170                 175

Ser Trp Arg Tyr Leu Ser Asn Arg Leu Leu Ala Pro Ser Asp Ser Pro
            180                 185                 190

Glu Trp Leu Ser Phe Asp Val Thr Gly Val Val Arg Gln Trp Leu Ser
            195                 200                 205

Arg Gly Gly Glu Ile Glu Gly Phe Arg Leu Ser Ala His Cys Ser Cys
    210                 215                 220

Asp Ser Arg Asp Asn Thr Leu Gln Val Asp Ile Asn Gly Phe Thr Thr
225                 230                 235                 240

Gly Arg Arg Gly Asp Leu Ala Thr Ile His Gly Met Asn Arg Pro Phe
                245                 250                 255

Leu Leu Leu Met Ala Thr Pro Leu Glu Arg Ala Gln His Leu Gln Ser
            260                 265                 270

Ser Arg His Arg Arg Ala Leu Asp Thr Asn Tyr Cys Phe Ser Ser Thr
        275                 280                 285

Glu Lys Asn Cys Cys Val Arg Gln Leu Tyr Ile Asp Phe Arg Lys Asp
    290                 295                 300

Leu Gly Trp Lys Trp Ile His Glu Pro Lys Gly Tyr His Ala Asn Phe
305                 310                 315                 320

Cys Leu Gly Pro Cys Pro Tyr Ile Trp Ser Leu Asp Thr Gln Tyr Ser
                325                 330                 335

Lys Val Leu Ala Leu Tyr Asn Gln His Asn Pro Gly Ala Ser Ala Ala
                340                 345                 350

Pro Cys Cys Val Pro Gln Ala Leu Glu Pro Leu Pro Ile Val Tyr Tyr
            355                 360                 365

Val Gly Arg Lys Pro Lys Val Glu Gln Leu Ser Asn Met Ile Val Arg
370                 375                 380

Ser Cys Lys Cys Ser
385

<210> SEQ ID NO 79
<211> LENGTH: 240
<212> TYPE: PRT
<213> ORGANISM: Homo sapiens

<400> SEQUENCE: 79

Met Asn Arg Cys Trp Ala Leu Phe Leu Ser Leu Cys Cys Tyr Leu Arg

```
1               5                   10                  15
Leu Val Ser Ala Glu Gly Asp Pro Ile Pro Glu Glu Leu Tyr Glu Met
                20                  25                  30

Leu Ser Asp His Ser Ile Arg Ser Phe Asp Asp Leu Gln Arg Leu Leu
                35                  40                  45

His Gly Asp Pro Gly Glu Glu Asp Gly Ala Leu Asp Leu Asn Met Thr
                50                  55                  60

Arg Ser His Ser Gly Gly Glu Leu Glu Ser Leu Ala Arg Gly Arg Arg
65                  70                  75                  80

Ser Leu Gly Ser Leu Thr Ile Ala Glu Pro Ala Met Ile Ala Glu Cys
                85                  90                  95

Lys Thr Arg Thr Glu Val Phe Glu Ile Ser Arg Arg Leu Ile Asp Arg
                100                 105                 110

Thr Asn Ala Asn Phe Leu Val Trp Pro Pro Cys Val Glu Val Gln Arg
                115                 120                 125

Cys Ser Gly Cys Cys Asn Asn Arg Asn Val Gln Cys Arg Pro Thr Gln
                130                 135                 140

Val Gln Leu Arg Pro Val Gln Val Arg Lys Ile Glu Ile Val Arg Lys
145                 150                 155                 160

Lys Pro Ile Phe Lys Lys Ala Thr Val Thr Leu Glu Asp His Leu Ala
                165                 170                 175

Cys Lys Cys Glu Thr Val Ala Ala Ala Arg Pro Val Thr Arg Ser Pro
                180                 185                 190

Gly Gly Ser Gln Glu Gln Arg Ala Lys Thr Pro Gln Thr Arg Val Thr
                195                 200                 205

Ile Arg Thr Val Arg Val Arg Arg Pro Pro Lys Gly Lys His Arg Lys
                210                 215                 220

Phe Lys His Thr His Asp Lys Thr Ala Leu Lys Glu Thr Leu Gly Ala
225                 230                 235                 240

<210> SEQ ID NO 80
<211> LENGTH: 288
<212> TYPE: PRT
<213> ORGANISM: Homo sapiens

<400> SEQUENCE: 80

Met Val Gly Val Gly Gly Gly Asp Val Glu Asp Val Thr Pro Arg Pro
1               5                   10                  15

Gly Gly Cys Gln Ile Ser Gly Arg Gly Ala Arg Gly Cys Asn Gly Ile
                20                  25                  30

Pro Gly Ala Ala Ala Trp Glu Ala Ala Leu Pro Arg Arg Arg Pro Arg
                35                  40                  45

Arg His Pro Ser Val Asn Pro Arg Ser Arg Ala Ala Gly Ser Pro Arg
                50                  55                  60

Thr Arg Gly Arg Arg Thr Glu Glu Arg Pro Ser Gly Ser Arg Leu Gly
65                  70                  75                  80

Asp Arg Gly Arg Gly Arg Ala Leu Pro Gly Gly Arg Leu Gly Gly Arg
                85                  90                  95

Gly Arg Gly Arg Ala Pro Glu Arg Val Gly Gly Arg Gly Arg Gly Arg
                100                 105                 110

Gly Thr Ala Ala Pro Arg Ala Ala Pro Ala Ala Arg Gly Ser Arg Pro
                115                 120                 125

Gly Pro Ala Gly Thr Met Ala Ala Gly Ser Ile Thr Thr Leu Pro Ala
                130                 135                 140
```

-continued

```
Leu Pro Glu Asp Gly Gly Ser Gly Ala Phe Pro Gly His Phe Lys
145                 150                 155                 160

Asp Pro Lys Arg Leu Tyr Cys Lys Asn Gly Phe Phe Leu Arg Ile
                165                 170                 175

His Pro Asp Gly Arg Val Asp Gly Val Arg Glu Lys Ser Asp Pro His
            180                 185                 190

Ile Lys Leu Gln Leu Gln Ala Glu Glu Arg Gly Val Val Ser Ile Lys
        195                 200                 205

Gly Val Cys Ala Asn Arg Tyr Leu Ala Met Lys Glu Asp Gly Arg Leu
    210                 215                 220

Leu Ala Ser Lys Cys Val Thr Asp Glu Cys Phe Phe Phe Glu Arg Leu
225                 230                 235                 240

Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
            260                 265                 270

Gly Pro Gly Gln Lys Ala Ile Leu Phe Leu Pro Met Ser Ala Lys Ser
        275                 280                 285
```

<210> SEQ ID NO 81
<211> LENGTH: 370
<212> TYPE: PRT
<213> ORGANISM: Homo sapiens

<400> SEQUENCE: 81

```
Met Thr Asp Arg Gln Thr Asp Thr Ala Pro Ser Pro Ser Tyr His Leu
1               5                   10                  15

Leu Pro Gly Arg Arg Arg Thr Val Asp Ala Ala Ala Ser Arg Gly Gln
                20                  25                  30

Gly Pro Glu Pro Ala Pro Gly Gly Val Glu Gly Val Gly Ala Arg
            35                  40                  45

Gly Val Ala Leu Lys Leu Phe Val Gln Leu Gly Cys Ser Arg Phe Gly
    50                  55                  60

Gly Ala Val Val Arg Ala Gly Glu Ala Glu Pro Ser Gly Ala Ala Arg
65                  70                  75                  80

Ser Ala Ser Ser Gly Arg Glu Glu Pro Gln Pro Glu Glu Gly Glu Glu
                85                  90                  95

Glu Glu Glu Lys Glu Glu Glu Arg Gly Pro Gln Trp Arg Leu Gly Ala
            100                 105                 110

Arg Lys Pro Gly Ser Trp Thr Gly Glu Ala Ala Val Cys Ala Asp Ser
        115                 120                 125

Ala Pro Ala Ala Arg Ala Pro Gln Ala Leu Ala Arg Ala Ser Gly Arg
    130                 135                 140

Gly Gly Arg Val Ala Arg Gly Ala Glu Glu Ser Gly Pro Pro His
145                 150                 155                 160

Ser Pro Ser Arg Arg Gly Ser Ala Ser Arg Ala Gly Pro Gly Arg Ala
                165                 170                 175

Ser Glu Thr Met Asn Phe Leu Leu Ser Trp Val His Trp Ser Leu Ala
            180                 185                 190

Leu Leu Leu Tyr Leu His His Ala Lys Trp Ser Gln Ala Ala Pro Met
        195                 200                 205

Ala Glu Gly Gly Gly Gln Asn His His Glu Val Val Lys Phe Met Asp
    210                 215                 220

Val Tyr Gln Arg Ser Tyr Cys His Pro Ile Glu Thr Leu Val Asp Ile
225                 230                 235                 240
```

```
Phe Gln Glu Tyr Pro Asp Glu Ile Glu Tyr Ile Phe Lys Pro Ser Cys
                245                 250                 255

Val Pro Leu Met Arg Cys Gly Gly Cys Cys Asn Asp Glu Gly Leu Glu
            260                 265                 270

Cys Val Pro Thr Glu Glu Ser Asn Ile Thr Met Gln Ile Met Arg Ile
        275                 280                 285

Lys Pro His Gln Gly Gln His Ile Gly Glu Met Ser Phe Leu Gln His
    290                 295                 300

Asn Lys Cys Glu Cys Arg Pro Lys Lys Asp Arg Ala Arg Gln Glu Asn
305                 310                 315                 320

Pro Cys Gly Pro Cys Ser Glu Arg Arg Lys His Leu Phe Val Gln Asp
                325                 330                 335

Pro Gln Thr Cys Lys Cys Ser Cys Lys Asn Thr Asp Ser Arg Cys Lys
            340                 345                 350

Ala Arg Gln Leu Glu Leu Asn Glu Arg Thr Cys Arg Cys Asp Lys Pro
        355                 360                 365

Arg Arg
    370

<210> SEQ ID NO 82
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Cys Pro Ser His Ile Ser Lys Tyr Ile Leu Arg Trp Arg Pro Lys Cys
1               5                   10                  15

<210> SEQ ID NO 83
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Cys Pro Ser Leu Ala Lys Lys Gln Arg Phe Arg His Arg Asn Arg Cys
1               5                   10                  15

<210> SEQ ID NO 84
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Cys Ile Ser Lys Tyr Ile Leu Arg Trp Arg Pro Lys Cys
1               5                   10
```

POLYPEPTIDES AND METHODS OF USE

CROSS-REFERENCE TO RELATED APPLICATIONS

This application is a U.S. national phase application filed under 35 U.S.C. §371 of International Application No. PCT/US2008/067105, which claims the benefit of the priority date of U.S. Provisional Application No. 60/944,068, filed Jun. 14, 2007, and of U.S. Provisional Application No. 60/986,976, filed Nov. 9, 2007. These prior applications are hereby incorporated by reference herein in their entirety.

GOVERNMENT SUPPORT

This invention was made with government support awarded by the National Institutes of Health under grant number AR10143. The government has certain rights in the invention.

SEQUENCE LISTING

The present application contains a Sequence Listing that was submitted in ASCII format vis EFS-Web on Jan. 23, 2014, and is hereby incorporated by reference into the present specification in its entirety.

TECHNICAL FIELD

This invention is based on the discovery that polypeptides derived from fibronectin and polypeptides derived from vitronectin can bind to growth factors and/or enhance growth factor activity. This invention relates to polypeptides derived from fibronectin and vitronectin that possess growth factor binding and/or enhancing activity and features methods for identifying compounds that promote or inhibit fibronectin and vitronectin binding to and/or enhancement of growth factors. This invention also relates to the uses of such compounds in cosmetic treatments and the treatment of wounds and cancer.

BACKGROUND

There is evidence that fibronectin is involved in many biological processes including tissue repair, embryogenesis, blood clotting, cell migration, wound repair, and cell adhesion. There are two primary forms of fibronectin. The first is an insoluble glycoprotein dimer that serves as a linker in the extracellular matrix (ECM), and the second is a soluble disulfide-linked dimer found in plasma. The ECM form of fibronectin is expressed by fibroblasts, chondrocytes, endothelial cells, macrophages and certain epithelial cells. The plasma form of fibronectin is expressed by hepatocytes. Fibronectin can serve as a general cell adhesion molecule by anchoring cells to collagen or to proteoglycan substrates. Fibronectin can also play a role in organizing cellular interactions by binding to components of the ECM and to membrane-bound fibronectin receptors on cell surfaces. Forms of fibronectin are found in vertebrates, including mammals, birds, amphibians, fish, and reptiles.

SUMMARY

We have discovered, inter alia, that fragments of fibronectin (FN), including fragments within domains $FNIII_{1-2}$, H and HV, bind growth factors and that those growth factors retain functional activity when bound. Furthermore, we discovered fibronectin fragments that are required for fibronectin null (FN-null) cell viability in the presence of a growth factor. Specifically, for viability in the presence of a growth factor, FN-null cells require a cell binding domain (e.g., $FNIII_{8-11}$) and a FN growth factor enhancing peptide. Based on these observations, we developed an assay (the "FN-null cell viability assay") for identifying polypeptide fragments, including smaller fibronectin fragments sufficient for FN-null cell viability in the presence of $FNIII_{8-11}$. Using this assay, we identified FN fragments and vitronectin (VN) fragments capable of supporting FN null cell survival and proliferation in the presence or absence of other growth factors. This assay is also useful for identifying compounds that inhibit the protein-protein or protein-cell interactions required for FN-null cell viability. Some fibronectin fragments were described previously in PCT/US2006/038778 which is incorporated by reference herein.

Accordingly, the invention features methods for identifying compounds that promote or inhibit FN-null cell viability in the assay described herein. These methods, and any of the present methods by which peptide sequences that inhibit binding and/or enhancement of GFs with FN or VN or VN GF-binding peptides or domains are identified, can be facilitated by phage display. One can use, for example, FN or VN GF peptides to find binding partners on phage display or use GF peptides to find binding partners on phage display. In either case, it is expected that the peptides found would interfere with FN or VN GF-binding/enhancing peptides. The invention also features compositions (e.g., physiologically acceptable compositions) that include a fragment of a fibronectin (e.g., a human fibronectin such as a human plasma fibronectin or ECM fibronectin) or a vitronectin (e.g., a human vitronectin) that binds a polypeptide growth factor (GF; e.g., a cytokine) or enhances growth factor activity. Furthermore, the invention features compositions that include a fragment of a growth factor (e.g., TGF-β1 or PDGF-BB) that inhibits fibronectin binding to a full-length growth factor. The physiologically acceptable compositions may be pharmaceutical compositions that promote a therapeutic response. As noted above, cosmetic compositions are also featured and can include the polypeptides described herein. The present compositions may also be non-pharmaceutical in the sense that they may include concentrated polypeptides and/or other ingredients that should be diluted or otherwise modified (e.g., mixed with other active or inactive ingredients) prior to use (e.g., in cell culture or as a cosmetic or therapeutic formulation).

In the binding of FN or VN fragments to growth factors, one or more of the biological activities of the bound GFs can be either retained (essentially fully retained or partially retained) or enhanced. The activity retained may be comparable to that of an unbound growth factor, but it may also be less; any degree of activity that confers a benefit on a cell or patient to whom the growth factor-containing complex is administered is useful. For example, where a GF exerts a positive effect on a biological process, such as wound healing, its biological activity would be retained or enhanced when bound to a FN fragment as described herein when the bound GF continues to exert a positive effect on the same biological process. While the fragment of fibronectin, vitronectin or the growth factor can be naturally occurring (i.e., either can have a sequence found in any species in any isoform), either or both of these components can also be biologically active variants of a naturally occurring fibronectin, vitronectin, or growth factor, respectively (e.g., their sequence can differ from that of a naturally occurring FN, VN, or GF sequence). Similarly, the glycosylation pattern may be that of a naturally occurring fibronectin, vitronectin or GF or may be altered due, for example, to expression in a heterologous cell (e.g., a bacterial cell). A biologically active variant of a FN or VN fragment described herein is one that, for example, functions as a GF-binding polypeptide and functions to a useful extent and in substantially the same manner as the corresponding FN fragment. For example, where a FN fragment having a naturally occurring sequence binds a GF with a particular affinity and, upon administration to a patient, effectively carries or delivers that GF to a site where the GF is needed, a biologically active variant of that FN fragment will be one that, although not identical to the FN fragment, will bind the same GF(s) with sufficiently useful affinity and similarly deliver the GF(s) to a site of need. For ease of reading, we do not repeat the term "or a biologically active variant thereof" after every reference to a FN fragment, VN fragment, GF or GF fragment, or other protein or peptide. It is to be understood that where FN, VN, or GF fragments having a naturally occurring sequence are useful, so are biologically active variants of those fragments. The same is true with reference to other proteins or polypeptides.

In various embodiments, the polypeptide growth factor can be an insulin like growth factor (e.g., IGF-1), a transforming growth factor (a TGF such as transforming growth factor-β1 (TGF-β1) or a transforming growth factor β2 (TGF-β2)), a fibroblast growth factor (e.g., basic fibroblast growth factor (bFGF), a fibroblast growth factor 7 (FGF-7)), a platelet-derived growth factor (e.g., PDGF-BB), a vascular endothelial growth factor A (VEGF-A), a nerve growth factor (NGF), or any combination or sub-combination thereof. The polypeptide growth factor or a variant thereof can have or retain biological activity (e.g., one or more of its known or discovered activities) when bound by the fragment of fibronectin (e.g., plasma fibronectin) or vitronectin.

The fragment of fibronectin, vitronectin, or growth factor can be derived from any species or type of fibronectin, vitronectin, or growth factor. For example, the fibronectin can be a human fibronectin, such as a human plasma fibronectin. Reference may be made to various fibronectin, vitronectin, or growth factor sequences, including precursor sequences that include signal sequences (e.g., precursor plasma fibronectins). One of ordinary skill in the art will recognize that the absolute position of a FN, VN, or GF polypeptide within a FN, VN, or GF protein can vary depending on, for example, the species of the protein or the form (e.g., whether a leader or pre-pro sequence is present or whether the protein sequence is fused to another sequence (e.g., a sequence that extends the circulating half-life of the FN polypeptide, such as an albumin or a portion of an immunoglobulin (e.g., the Fc region of an IgG))). Polypeptides derived from various forms of FN and various modified forms thereof (e.g., biologically active mutants and FN polypeptide-containing complexes, as described further below) can be used in the present compositions and methods.

The fragments described herein can vary in length and sequence. With respect to sequence, a fragment of fibronectin can have a sequence normally found within the region designated $FNIII_1$, $FNIII_2$, $FNIII_{12-14}$, $FNIII_{12-V15}$ (HV) or IIICS. A fragment of fibronectin can have or can include a sequence normally found within the region designated or a portion thereof; $FNIII_1$ or a portion thereof; $FNIII_2$ or a portion thereof; $FNIII_{12-V15}$ or a portion thereof; $FNIII_{12-15}$ or a portion thereof; $FNIII_{12-14}$ or a portion thereof; $FNIII_{12-13}$ or a portion thereof; $FNIII_{13-14}$ or a portion thereof; IIICS or a portion thereof. The portions may be as short as 3-10 amino acid residues (e.g., 4, 5, 6, 7, or 8 contiguous residues). With respect to function, a fragment can bind a polypeptide growth factor with an affinity of at least or about $1 \times 10^{-7}$M (e.g., at least $1 \times 10^{-8}$M; $1 \times 10^{-9}$ M; or more). Alternatively, or in addition, a fragment may support FN null cell survival and/or proliferation.

Where a biologically active fragment of fibronectin, vitronectin, or growth factor is used, the fragment can be at least or about 80% identical (e.g., at least or about 85%, 90%, 95%, 98%, or 99% identical) to a corresponding wild type fragment of fibronectin, vitronectin, or growth factor.

Alternatively, or in addition, the fragment can further include a substituent at the amino-terminus or carboxy-terminus. The substituent can be an acyl group or a substituted or unsubstituted amine group (e.g., the substituent at the N-terminus can be an acyl group and the C-terminus can be amidated with a substituted or unsubstituted amine group (e.g., an amino group having one, two, or three substituents, which may be the same or different)). The amine group can be a lower alkyl (e.g., an alkyl having 1-4 carbons). The acyl group can be a lower acyl group (e.g., an acyl group having up to four carbon atoms), especially an acetyl group.

The isolated polypeptides may include a sequence that conforms strictly to a sequence described herein (e.g., a sequence conforming to a generic formula or that or a particularly disclosed polypeptide (e.g., a polypeptide can consist of an amino acid sequence conforming to Formula I). Alternatively, an isolated polypeptide may further include additional sequence constituting the sequence that naturally flanks the subject sequence (e.g., a polypeptide can include an amino acid sequence conforming to Formula I and additional sequence that is found naturally in FN). A "fragment" cannot, however, encompass a full length and naturally occurring FN or VN protein. Thus, the fragments can include, at their N-terminus or C-terminus (or both), amino acid residues that are or are not naturally found in fibronectin, vitronectin, or a growth factor.

Where biologically active variants of a fragment are used, the variant can vary by substitution of one or more amino acid residues within these groups. The variants can include a conservative amino acid substitution.

The fragments of fibronectin, vitronectin, or growth factor, including the modified fragments described above, can be protease resistant and can include one or more types of protecting groups such as an acyl group, an amide group, a benzyl or benzoyl group, or a polyethylene glycol. More specifically, a fragment of fibronectin, including the modified fragments described above, can be N-terminally acetylated and/or C-terminally amidated.

The fragments of fibronectin can also be modified in order to improve absorption, including for example, an addition of sugar residues to enhance transport across the blood-brain barrier.

Any of the fragments can include at least one amino acid residue in the D-form.

Any of the fragments can include at least one non-naturally occurring or modified amino acid residue (e.g., 4-hydroxyproline, gamma-carboxyglutamic acid, o-phosphoserine, o-phosphotyrosine, or delta-hydroxylysine). Non-naturally occurring amino acid residues are amino acid residues other than the 20 naturally occurring, genetically encoded amino acids. Other examples include naphthylalanine, which can be substituted for trytophan to facilitate synthesis, L-hydroxypropyl, L-3,4-dihydroxyphenylalanyl, alpha-amino acids such as L-alpha-hydroxylysyl and D-alpha-methylalanyl, L-alpha-methylalanyl, beta-amino acids, and isoquinolyl. Fragments having non-naturally occurring amino acid residues may be referred to as synthetic fragments and constitute one type of variant as described herein. Other variants include fragments of fibronectin in which a naturally occurring side chain of an amino acid residue is replaced with a non-naturally occurring side chain (in either the L- or D-form). In another aspect, the invention features polypeptides that include a sequence that is reversed with respect to the N- and C-termini of a sequence naturally found in a fibronectin, vitronectin, or growth factor polypeptide or a biologically active variant thereof.

Any of the fragments in the present compositions can be one of a plurality of fragments present. These fragments may be linked together by methods described herein. As noted, fragment of fibronectin, vitronectin, or a growth factor, including the variant forms described herein, can further include a heterologous polypeptide (i.e., a polypeptide having a sequence that does not appear in a fibronectin, vitronectin, or a growth factor). The heterologous polypeptide can be a polypeptide that increases the circulating half-life, cell penetration or transdermal penetration of the fragment, to which it is attached.

The fragments can be contained within physiologically acceptable compositions or they may be contained within compositions that are not suitable for administration to a living being (e.g., concentrated stocks or frozen or lyophilized compositions).

The physiologically acceptable compositions can be pharmaceutical compositions, and methods of treating patients are described further below. The physiologically acceptable compositions can also be non-pharmaceutical compositions or pharmaceutical compositions that can be dispensed without a physician's prescription. For example, they can be sold "over the counter" for cosmetic purposes (e.g., to reduce the risk of damage from the skin or to minimize or repair damage to the skin). For example, the fragments of fibronectin, vitronectin, or a growth factor and compositions that include them or combinations of them (e.g., a FN-growth factor complex) can be incorporated in topical formulations sold as cosmetics, moisturizers and the like, sunscreens, shampoos or conditioners, soaps or other foaming cleansers, or lip balm.

The invention also encompasses nucleic acid molecules that encode the polypeptides described herein or the GFs that may be present in complexes with the FN or VN fragments. Specific nucleic acid molecules, vectors (e.g., plasmid vectors), and host cells containing them are described further below, as are physiologically acceptable compositions containing them.

Other compositions of the present invention are tissue engineered products that include a fragment of a fibronectin or vitronectin or a biologically active variant thereof. As in other compositions, the fragment or the variant thereof can bind a polypeptide growth factor or enhance growth factor activity (as described above and further below), which factor may subsequently retain biological activity and may be administered to a patient.

Other compositions of the present invention comprise a solid support that is associated with (e.g., bound to or impregnated with) one or more of the fragments of fibronectin or vitronectin, or the biologically active variants thereof, described herein. The support can be, for example, a tissue culture vessel (e.g., a plate or flask) or device (e.g., a medical device such as one used in wound dressing (e.g., a bandage or gauze), wound repair (e.g., a suture or "steri-strip"), surgical repair (e.g., a surgical mesh), or a tissue implant (e.g. a stent). The fragment of fibronectin or vitronectin, or the biologically active variant thereof, can be bound to an active growth factor, including any of those described above.

The methods of the invention include methods for treating a patient who has cancer. These methods can be carried out by, for example, administering to the patient a therapeutically effective amount of a pharmaceutical composition comprising a fragment of fibronectin or vitronectin, or a biologically active variant thereof, as described herein. These methods can be carried out by, for example, administering to the patient a therapeutically effective amount of a pharmaceutical composition comprising a fragment of a growth factor that binds to fibronectin and/or vitronectin or to a fibronectin or vitronectin fragment. The methods can optionally include a step of identifying a patient in need of treatment, and that patient can have a cancer associated with overexpression of a growth factor (e.g., overexpression of IGF-1, TGFβ1, TGFβ2, PDGF-BB, bFGF, FGF-7, VEGF-A or NGF. In addition to administration of a compositions described herein, the patient can receive a second type of treatment for cancer. That is, the present compositions can be used in conjunction with existing chemotherapies, radiation therapy, surgery, or any other cancer treatment.

Other methods of the invention are methods for promoting wound healing. These methods include a step of administering to a patient a therapeutically effective amount of a pharmaceutical composition comprising a fragment of fibronectin or vitronectin, or a biologically active variant thereof, as described herein. The fragment of fibronectin or vitronectin, or the biologically active variant thereof, can be present in a complex with one or more growth factors. The methods can optionally include a step of identifying a patient in need of treatment. Such patients include patients who are suffering from a surgical extirpation or incision of the skin, mucosa, underlying connective tissue, fascia, ligament, tendon, cartilage, bone, nerve or muscle; patients who are suffering from a traumatic laceration or tissue loss of the skin, mucosa, underlying connective tissue, fascia, nerve or muscle; and patients who are suffering from a burn or ulceration of the skin, mucosa, underlying connective tissue, fascia, nerve or muscle.

Suitable formulations are described further below and, generally, take the form of a solution, lotion, ointment, gel, cream or salve. The fragments of fibronectin or vitronectin, whether or not complexed with a growth factor, can also be administered by way of their inclusion in an extracellular matrix (ECM; e.g., a natural or engineered ECM), a bandage, dressing, compress, or the like.

By other methods of the invention, one can localize an endogenous growth factor to a tissue of a patient. These methods can be carried out by administering, to the patient, a therapeutically effective amount of a composition that includes a fragment of fibronectin, or a biologically active variant thereof, as described herein. As in the more specific treatment methods described above, these compositions can be administered by way of topical application of a pharmaceutical composition, an engineered ECM, or a solid support. These methods can be described as methods of delivering one or more growth factors to a patient. The methods can optionally include a step of identifying a patient in need of treatment. Such patients include patients who are suffering from an injury to a tissue, a loss of a tissue or a disorder resulting in tissue disfigurement or dysfunction. More specifically, the patient can be suffering from an injury or loss to the brain, spinal cord or nerves or a disorder resulting in brain, spinal cord or nerve dysfunction; an injury or loss to the heart or blood vessels or a disorder resulting in heart or blood vessel dysfunction; an injury or loss to the lung, nasopharyngeal tract, sinuses, trachea or airways or a disorder resulting in lung, nasopharyngeal tract, sinus, trachea or airway dysfunction; an injury or loss to the gastrointestinal tract, liver or pancreas or a disorder resulting in gastrointestinal tract, liver or pancreas dysfunction; an injury or loss to a kidney, ureters, bladder or urethra or a disorder resulting in kidney, ureters, bladder or urethra dysfunction; an injury or loss to bone, cartilage, synovium, menicus, ligament, tendon or nucleus pulposus or a disorder resulting in bone, cartilage, synovium, menicus, ligament, tendon or nucleus pulposus dysfunction; an injury or loss to lips, tongue or gums or a disorder resulting in lip, tongue and gum dysfunction; an injury or loss to the subcutaneous tissue or a disorder resulting in subcutaneous tissue dysfunction.

In another aspect, the invention features methods for promoting the isolation, proliferation, and/or differentiation of stem cells. The methods can be carried out with various compositions, including fragments of fibronectin or vitronectin per se as well as complexes containing such fragments bound to growth factors and the tissue-engineered solid-support products described herein. Similarly, one can promote the delivery of stem cells by administering to a patient a therapeutically effective amount of a composition that includes stem cells and a fragment of fibronectin or vitronectin as described herein (in its various forms, including forms in which the fragment of fibronectin or vitronectin is associated with a solid support or contained within a tissue engineered product). More generally, the methods of the invention include methods for promoting the isolation, proliferation, and delivery of cells. As noted, these cells can be stem cells or can be differentiating into, or differentiated into, osteoblasts, epithelial cells, fibroblasts, adipocytes, myocytes, neural cells, endothelial cells, chondrocytes, hematopoietic cells or lymphocytes. The cells can be genetically engineered or simply isolated from a patient or a cell or tissue culture.

In another aspect, the invention features methods of screening for candidate inhibitors of growth factor-growth factor binding peptide complexes. The screening methods can be carried out by, for example: (a) providing (i) inducible cells, (ii) a tissue-engineered product or solid support comprising one or more fragments of fibronectin or biologically active variants thereof, (the fragments being; as described herein, capable of binding growth factors), (iii) one or more candidate inhibitors, and (iv) one or more growth factors; (b) contacting the cells in vitro with the tissue-engineered product or solid support; and (c) measuring the extent of cell function of the substrate.

The invention can also be described in terms of "use," in which case it encompasses "use" of the compositions described herein, including FN fragments, VN fragments, GF fragments, complexes containing one or more of FN and VN fragments, including those with a bound GF, nucleic acids encoding the present FN, VN, or GF fragments, expression vectors, host cells, and tissue engineered products for the treatment of cancer or for the preparation of a medicament for the treatment of cancer.

The invention further encompasses "use" of the compositions described herein, including FN VN, or GF fragments; complexes containing one or more of FN and VN fragments, including those with a bound GF; nucleic acids encoding the present FN, VN, or GF fragments; expression vectors; host cells; and tissue engineered products, including those that contain biomaterials, for promoting tissue regeneration and/or tissue repair. For example, the present compositions can be used in promoting wound healing, and for the treatment of cancer, or for the preparation of a medicament for the promotion of tissue regeneration or wound healing, and for the treatment of cancer. The tissue regeneration or repair may result in healing with little or no scarring, in contradistinction with usual adult wound healing.

The details of one or more embodiments of the invention are set forth in the accompanying drawings and the description below. Other features, objects, and advantages of the invention will be apparent from the description and drawings, and from the claims.

As used herein, "growth factor binding peptide" (or "GFBP") and "growth factor enhancing peptide" (or "GFEP") are used synonymously.

As used herein, "intrinsic growth factor activity" refers to the ability of a polypeptide to promote cell survival or proliferation (e.g., in the absence of a growth factor).

As used herein, "cell attachment moiety" refers to a cell-binding moiety, (e.g., a cell binding fragment of fibronectin).

As used herein, "cosmetic treatment" refers to the use of a physiologically acceptable composition to improve or maintain the appearance of an individual.

BRIEF DESCRIPTION OF THE DRAWINGS

FIG. 4 is a representation of a plasma fibronectin polypeptide sequence (SEQ ID NO:1).

FIG. 10A is an exemplary amino acid sequence of human TGF-β1 (SEQ ID NO:78).

FIG. 10B is an exemplary amino acid sequence of human PDGF-BB (SEQ ID NO:79).

FIG. 10C is an exemplary amino acid sequence of human FGF-2 (SEQ ID NO:80).

FIG. 10D is an exemplary amino acid sequence of human VEGF-A (SEQ ID NO:81).

DETAILED DESCRIPTION

Figure 1:
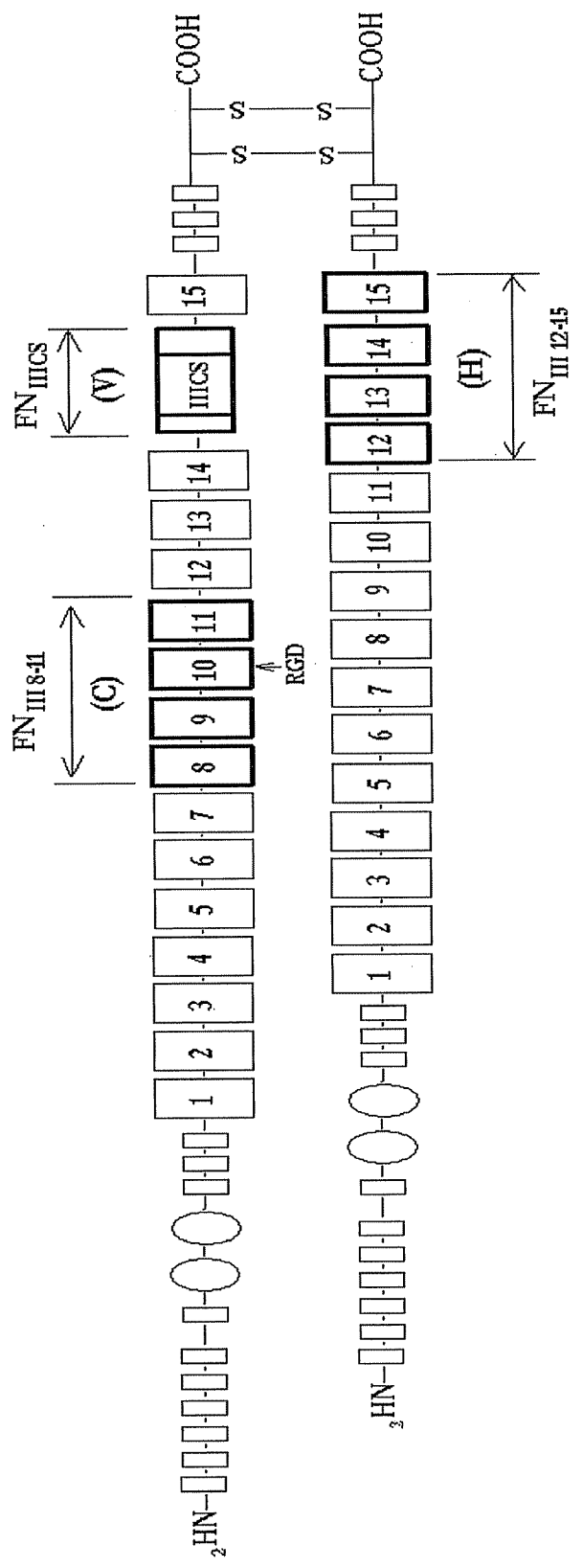
FIG. 1 is a diagram of human plasma fibronectin.

Fibronectin is a multi-domain and multifunctional cell adhesion protein found in blood and various extracellular matrices. Fibronectin molecules consist of several functional domains, including: two heparin binding domains, Hep I and Hep II; two fibrin binding domains, Fib I and Fib II; a collagen or gelatin binding domain; an RGD cell-binding domain; and a variably spliced domain. Each functional domain is composed of highly homologous FN molecular domains: the type 1 repeats (FNI), type 2 repeats (FNII), and type 3 repeats (FNIII).

Vitronectin is a multi-domain and multifunctional glycoprotein found in blood and extracellular matrix. Vitronectin plays roles in fibrinolysis and cell migration and has been implicated in hemostasis and tumor malignancy.

As detailed below, we have found, inter alia, that specific fragments of fibronectin and vitronectin can bind various growth factors (e.g., IGF-1, TGF-β1, TGF-β2, bFGF, FGF-7, PDGF-BB, VEGF-A, or NGF), and the bound growth factors can retain a biological activity. We have also found that specific fragments of fibronectin and vitronectin have intrinsic growth factor activity, i.e., promote cell survival or proliferation. The present invention features compositions that include such fragments, with or without bound growth factors in the represented families (i.e., in the IGF, TGF, FGF, PDGF, VEGF, and NGF families), in various formulations and configurations. The peptides may promote synergy with GFs to which the FN fragments do not bind. In one configuration, the FN fragments, or FN fragment/GF-containing complexes can be incorporated into engineered two- or three-dimensional extracellular matrices (which we may abbreviate herein as engECM or refer to as synthetic matrices), and these can include any of, or any combination of, the fibronectin or vitronectin fragments described herein (e.g., a FN polypeptide conforming to any of Formulas I, II, or III) or biologically active variants thereof. The growth factor(s) incorporated can be, for example, IGF-1, TGF-β1, TGF-β2, bFGF, FGF-7, PDGF-BB, VEGF-A, or NGF; any combination or sub-combination thereof; or another specific growth factor in the same family as those listed. The growth factors can be exogenously added to the FN fragment-containing formulation (e.g., a FN fragment-containing matrix), or the formulation (e.g., the matrix) can be generated without growth factors. In the latter case, when placed in the vicinity of an endogenous supply of growth factors, the growth factors can be recruited by the matrix. The matrix can also recruit cells and induce them to differentiate, produce tissue or proliferate (presumably by virtue of the inclusion or recruitment of growth factors, although the invention is not limited to compositions that function by any particular mechanism).

The matrix can include any type of biomaterial (e.g., a biopolymer). For example, the matrix can be or can include a hydrogel (e.g., an intramolecularly crosslinked hydrogel). The present peptides and GFs can be incorporated in or associated with many different types of materials (e.g., hyaluronan). The matrix can have, for example, a polycarbonate backbone, or include biodegradeable polyurethanes. Further examples of suitable biopolymers are: proteins (e.g., collagen), protein-containing macromolecules (e.g., proteoglycans), silk (e.g., a derivatized silk), alginate, chitan and chitosan.

In one embodiment, the engineered extracellular matrix is composed of three fibronectin functional domains (FNfds) or biologically active variants or portions thereof: $FNIII_{8-11}$ (C), $FNIII_{12-15}$ (H) and $FNIII_{12-v15}$ (HV), which can be constructed recombinantly as arrayed on a natural FN heterodimer and incorporated into a hydrogel (e.g., tethered to an intramolecularly crosslinked hyaluronan (HA) hydrogel). The isolated domains useful within the present engineered matrices (e.g., $FNIII_{8-11}$ (C), $FNIII_{12-15}$ (H) and $FNIII_{12-v15}$ (HV)) are within the scope of the invention, and these domains can be formulated and modified as described herein for FN fragments, such as those conforming to any of formulas I, II, or III.

The invention also features fragments of growth factors that bind to fibronectin and/or vitronectin. Peptide sequences have been identified within growth factors which inhibit the growth factors ability to bind to provisional matrix molecules, e.g., fibronectin and vitronectin, which abound in tumor stroma. The present invention features compositions that include such fragments in various formulations and configurations. For example, fragments of growth factors could be used to flush growth factors from solid tumors.

For preparation of pharmaceutical compositions containing one or more of the present fibronectin fragments, vitronectin fragments, growth factors, or active fragments thereof, for prophylactic and/or therapeutic treatments, the active ingredients (e.g., the FN fragment alone or the FN fragment bound to G(s)) can be incorporated alone or in combination with other active agents into compositions suitable for administration to a patient. The formulations can be made using methods routine in the art and particular guidance may be provided by prior formulations of protein-based therapeutics. The compositions will be physiologically acceptable (i.e., substantially non-toxic) and may be formulated as prescription medications or over-the-counter products. Pharmaceuticals or pharmaceutically acceptable compositions contain compounds (e.g., polypeptides), other materials (e.g., diluents), and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

Nucleic acid molecules that encode the fibronectin (FN), vitronectin (VN), or growth factor (GF) fragments described herein can also be formulated for use in cell culture or administration to a patient or subject. Such compositions commonly include a pharmaceutically acceptable carrier, and carriers are contemplated in the present formulations. Any conventional media or agent compatible with the active ingredients can be used in the present compositions. While formulations and methods of use are described further below, we note here that application to human patients is intended, as is application to animals (e.g., domesticated, farm, or show animals). The invention extends to non-physiologically acceptable compositions in that it extends to preparatory compositions and compositions suitable for storage (e.g., concentrated stocks and frozen or lyophilized preparations).

While specific FN, VN, and GF fragments are described herein, the present compositions encompass those that include FN fragments of any length less than a full-length, naturally occurring fibronectin, VN fragments of any length less than a full-length, naturally occurring vitronectin, and GF fragments of any length less than a full-length, naturally occurring growth factor. For example, a FN fragment can lack one or more domains of fibronectin, provided that the sequence of the first fibronectin type III repeat domain, the thirteenth fibronectin type III repeat domain, or the III CS domain are present. For example, a VN fragment can lack one or more domains of vitronectin, provided that the fragment of interest promotes fibronectin-null (FN-null) cell survival or proliferation in the screening assay described herein. For example, a GF fragment can lack one or more domains of the growth factor, provided that the fragment of interest binds to a provisional matrix molecule in a binding assay as described herein.

Fibronectin fragments: Fibronectin fragments featured herein can be described in a variety of ways and with respect to various features. With respect to length, the featured fragments can have about, or less than about, 500 (e.g., 510, 505, 501, or no more than 498, 488, 478, 468, 458, 448, 438, or 428), 400 (e.g., 410, 405, 401, or no more than 398, 388, 378, 368, 358, 348, 338, or 328), 300 (e.g., 310, 305, 301, or no more than 298, 288, 278, 268, 258, 248, 238, or 228), 200 (e.g., 210, 205, 201, or about or no more than 198, 188, 178, 168, 158, 148, 138, or 128), 100, 75, 50, 45, 40, 35, 30, 28, 27, 26, or 25 amino acid residues. For example, the fragment can include no more than 25 or 26 amino acid residues (e.g., no more than 26 amino acid residues that are identical to 26 contiguous amino acid residues found in a naturally occurring fibronectin protein).

With respect to length, the featured fragments can constitute about or no more than about 1-2%, 2-5%, 5-10%, or 10-25% of the amino acid sequence of a naturally occurring FN (e.g., as shown in FIG. 4). However, larger fragments may have GF-binding abilities and may therefore be useful as well.

With respect to sequence, the featured fragments of fibronectin can have a sequence that corresponds to or that is normally found within the region designated $FNIII_1$, $FNIII_2$, $FNIII_{12-14}$, $FNIII_{12-V15}$ (HV) or IIICS. The portions may be as short as 3-10 amino acid residues (e.g., 4, 5, 6, 7, or 8 contiguous residues).

More specifically, and in accordance with a consensus sequence based on some of the useful fragments of FN we discovered, the compositions of the present invention can include a fragment of fibronectin or a biologically active variant thereof that has an amino acid sequence conforming to Formula I:

(SEQ ID NO: 72)
$Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-

$Xaa_{11}$-$Xaa_{12}$-$Xaa_{13}$-$Xaa_{14}$-$Xaa_{15}$-$Xaa_{16}$-$Xaa_{17}$-$Xaa_{18}$-$Xaa_{19}$ (Formula I)

In Formula I, $Xaa_1$ can be Gln or Asn (e.g., Gln); $Xaa_2$ can be any one or two amino acid residues (e.g., Pro, Leu-Ile, or Gly); $Xaa_3$ can be Ser or Thr (e.g., Ser); $Xaa_4$ can be absent or any single amino acid residue (e.g., $Xaa_4$ can be absent, His, or Val); $Xaa_5$ can be Ile or Gly (e.g., Ile); $Xaa_6$ can be Ser or Gln (e.g., Ser); $Xaa_7$ can be Lys, Arg or Gln (e.g., Lys); $Xaa_8$ can be Tyr, Thr, or Met (e.g., Tyr); $Xaa_9$ can be Ile or Gly (e.g., Ile); $Xaa_{10}$ can be any four or five amino acid residues (e.g., Leu-Arg-Trp-Arg (SEQ ID NO: 76)); $Xaa_{11}$ can be absent or any single amino acid residue (e.g., $Xaa_{11}$ can be absent or Pro); $Xaa_{12}$ can be Lys or Arg (e.g., Lys); $Xaa_{13}$ can be any one or two amino acid residues (e.g., Asn-Ser); $Xaa_{14}$ can be any one or two amino acid residues (e.g., Val-Gly); $Xaa_{15}$ can be Arg or Thr (e.g., Arg); $Xaa_{16}$ can be any one or two amino acid residues (e.g., Trp); $Xaa_{17}$ can be Lys, Gln, Thr, or Ser (e.g., Lys); $Xaa_{18}$ can be any two amino acid residues (e.g., Glu-Ala); and $Xaa_{19}$ can be Thr. In certain embodiments, certain provisos may apply. For example, the fragment of fibronectin, where identical to a portion of a naturally occurring fibronectin, may not be QWNAPQPSHISKYILRWRP-KNSVGRWKEATIPGHLNSYTIKGLKPGV-VYEGQLISIQQYGHQEVTRFDFTTTSTST (SEQ ID NO:2) or may not be more than at least or about 40%, 50%, or 60% of this sequence (i.e., of SEQ ID NO:2).

Specific fragments are described elsewhere herein and include those designated as peptides 1-4, 1A, and 1B. For example, specific fragments are QPSHISKYILRWRPKNS-VGRWKEAT (peptide 1; SEQ ID NO:3); QLI-SIQQYGHQEVTRFDFTTTSTST (peptide 2; SEQ ID NO:4); NGQTPIQRTIKPDVRSYTITGLQPGT (peptide 3; SEQ ID NO:5); and QPSVGQQMIFEEHGFRRTTPPTTAT (peptide 4; SEQ ID NO:6). The specific sequences described herein are derived from a human plasma fibronectin. In addition, one can use corresponding sequences (e.g., fragments having a corresponding sequence from any fibronectin isoform of any species).

In other embodiments, the fragment of fibronectin used in one or more of the various compositions described herein, or biologically active variants thereof, can have, or can include, an amino acid sequence conforming to Formula II:

(SEQ ID NO: 73)
$Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$ (Formula II).

In Formula II, $Xaa_1$ can be Gln or Asn (e.g., Gln); $Xaa_2$ can be any amino acid residue (e.g., Pro); $Xaa_3$ can be Ser or Thr (e.g., Ser); $Xaa_4$ can be any amino acid residue (e.g., His); $Xaa_5$ can be Ile or Gly (e.g., Ile); $Xaa_6$ can be Ser or Gln (e.g., Ser); $Xaa_7$ can be Lys, Arg or Gln (e.g., Lys); $Xaa_8$ can be Tyr, Thr, or Met (e.g., Tyr); $Xaa_9$ can be Ile or Gly (e.g., Ile); $Xaa_{10}$ can be any four amino acid residues (e.g., Leu-Arg-Trp-Arg (SEQ ID NO: 76)); $Xaa_{11}$ can be any amino acid residue (e.g., Pro); and $Xaa_{12}$ can be Lys or Arg (e.g., Lys). For example, the compositions of the invention can include a fragment of fibronectin that has, or that includes, the sequence QPSHISKYILRWRPK (SEQ ID NO:7).

In Formula III, $Xaa_1$ can be Ile or Gly (e.g., Ile); $Xaa_2$ can be any four or five amino acid residues and $Xaa_3$ can be absent or any single amino acid residue (e.g., $Xaa_2$ can be Leu-Arg-Trp-Arg-Pro (SEQ ID NO: 77) and $Xaa_3$ can be absent or $Xaa_2$ can be Leu-Arg-Trp-Arg (SEQ ID NO: 76) and $Xaa_3$ can be Pro); $Xaa_4$ can be Lys or Arg (e.g., Lys); $Xaa_5$ can be any one or two amino acid residues (e.g., Asn-Ser); $Xaa_6$ can be any one or two amino acid residue (e.g., Val-Gly); $Xaa_7$ can be Arg or Thr (e.g., Arg); $Xaa_8$ can be any one or two amino acid residues (e.g., Tip); and $Xaa_9$ can be Lys, Gln, Thr, or Ser (e.g., Lys). For example, the compositions of the invention can include a fragment of fibronectin that has, or that includes, the sequence ILRWRPKNSVGRWK (SEQ ID NO:8).

In other embodiments, the isolated polypeptide (e.g., the fragment of fibronectin) used in one or more of the various compositions described herein, or biologically active variants thereof, can have, or can include, an amino acid sequence conforming for Formula IV:

(SEQ ID NO: 56)
$Xaa_1$-$(Xaa_2)_m$-$Xaa_3$-$Xaa_4$-$Xaa_5$-$Xaa_6$-$Xaa_7$ (Formula IV)

With respect to Formula IV, $Xaa_1$ can be Pro or any non polar amino acid and $Xaa_2$ can be any amino acid residue. As m can be an integer between 0 and 8, Xaa2 can be absent or can be a series of amino acid residues from 1 to 8 residues long. $Xaa_3$ can be Lys or Arg; $Xaa_1$ can be any amino acid residue; $Xaa_5$ can be Lys or Arg; $Xaa_6$ can be any amino acid residue; and $Xaa_7$ can be Lys or Arg. For example, $Xaa_1$ can be Pro; m can be 0, 2, 4, 6, or 8; $Xaa_3$ can be Lys; $Xaa_3$ can be Arg; $Xaa_4$ can be Trp; $Xaa_5$ can be Lys; and $Xaa_6$ can be Pro or any non-polar amino acid residue.

For example, the compositions of the invention can include a fragment of fibronectin that has, or that includes, the sequence PSHISKYILRWRPK (SEQ ID NO:9).

With respect to function, the featured FN fragments can bind a polypeptide growth factor with an affinity of about or at least about $1\times10^{-6}$-$1\times10^{-7}$ (e.g., about or at least about $5\times10^{-7}$; $1\times10^{-8}$; $5\times10^{-8}$; $1\times10^{-9}$; or $5\times10^{-9}$). Alternatively or in addition, the featured FN fragments support FN null cell survival and/or proliferation secondary to intrinsic growth factor activity and/or growth factor enhancing activity.

In addition to GF-binding and/or enhancement, the featured FN fragments can exhibit a certain degree of identity or homology to a corresponding wild type fragment of fibronectin. The extent of identity may be described not only in reference to the current polypeptides, but also in reference to the nucleic acid molecules that encode them. Biologically active variants of a fragment of fibronectin may differ from the wild type fragment by virtue of having one or more substitutions, additions or deletions of one or more amino acid residues. The substitutions can be conservative or non-conservative substitutions, and the amino acid side chains may also be modified.

Where a conservative amino acid substitution is made, the substitution can be of one amino acid residue for another in any of the following groups: arginine, histidine, and lysine; aspartic acid and glutamic acid; alanine, leucine, isoleucine and valine; and phenylalanine, tryptophan and tyrosine. The amino acid residues listed here are naturally occurring. Non-naturally occurring amino acid residues of like kind may also be substituted. For example, a negatively charged non-naturally occurring amino acid residue may be substituted for a negatively charged naturally occurring amino acid residue; a hydrophobic aromatic non-naturally occurring amino acid residue may be substituted for a hydrophobic aromatic naturally occurring amino acid residue; and so forth. The teaching just provided regarding conservative amino acid substitutions is applicable to any of the peptides described herein.

The degree of identity can vary and can be determined by methods well established in the art. "Homology" and "identity" each refer to sequence similarity between two polypeptide sequences, with identity being a more strict comparison. Homology and identity can each be determined by comparing a position in each sequence which may be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be referred to as homologous at that position. A percentage of homology or identity between sequences is a function of the number of matching or homologous positions shared by the sequences. A biologically active variant of a polypeptide described herein can have at least or about 25%, 50%, 65%, 75%, 80%, 85%, 90%, 95%, 96%, 97%, 98%, or 99% identity or homology to a corresponding naturally occurring polypeptide (e.g., a FN fragment). The nucleic acids encoding the biologically active variant polypeptides can be similarly described as having at least or about 25%, 50%, 65%, 75%, 80%, 85%, 90%, 95%, 96%, 97%, 98%, or 99% identity to a corresponding naturally occurring nucleic acid sequence. Those of ordinary skill in the art will readily recognize degenerate variants of nucleic acid sequences, and such variants can be used for the purposes described herein. The teaching just provided regarding homology and identity is applicable to any of the peptides described herein.

Vitronectin Fragments:

Vitronectin fragments featured herein can be described in a variety of ways and with respect to various features. With respect to length, the featured fragments can have about, or less than about, 500 (e.g., 510, 505, 501, or no more than 498, 488, 478, 468, 458, 448, 438, or 428), 400 (e.g., 410, 405, 401, or no more than 398, 388, 378, 368, 358, 348, 338, or 328), 300 (e.g., 310, 305, 301, or no more than 298, 288, 278, 268, 258, 248, 238, or 228), 200 (e.g., 210, 205, 201, or about or no more than 198, 188, 178, 168, 158, 148, 138, or 128), 100, 75, 50, 45, 40, 35, 30, 28, 27, 26, or 25 amino acid residues. For example, the fragment can include no more than 25 or 26 amino acid residues (e.g., no more than 26 amino acid residues that are identical to 26 contiguous amino acid residues found in a naturally occurring vitronectin protein).

The fragment of VN can conform to Formula IV.

For example, in Formula IV, $Xaa_1$ can be Pro or any non polar amino acid (e.g., Pro); $Xaa_2$ can be any or no amino acid residues (e.g., Ser); $Xaa_3$ can be any or no amino acid residues (e.g., Leu); $Xaa_4$ can be any or no amino acid residues (e.g., Ala); $Xaa_5$ can be any or no amino acid residues (e.g., Lys); $Xaa_6$ can be any or no amino acid residues (e.g., Lys); $Xaa_7$ can be any or no amino acid residues (e.g., Gln); $Xaa_8$ can be any or no amino acid residues (e.g., Arg); $Xaa_9$ can be any or no amino acid residues (e.g., Phe); $Xaa_{10}$ can be Lys or Arg (e.g., Arg), $Xaa_{11}$ can be any amino acid residue (e.g., His); $Xaa_{12}$ can be Lys or Arg (e.g., Arg); $Xaa_{13}$ can be any amino acid residue (e.g., Asn); and $Xaa_{14}$ is Lys or Arg (e.g., Arg). For example, the compositions of the invention can include a fragment of vitronectin that has, or that includes, the sequence PSLAKKQRFRHRNR (SEQ ID NO:10).

With respect to function, the featured VN fragments can bind a polypeptide growth factor with an affinity of about or at least about $1\times10^{-6}$-$1\times10^{-7}$ (e.g., about or at least about $5\times10^{-7}$; $1\times10^{-8}$; $5\times10^{-8}$; $1\times10^{-9}$; or $5\times10^{-9}$). Alternatively or in addition, the featured VN fragments support FN null cell survival and/or proliferation secondary to intrinsic growth factor activity and/or growth factor enhancing activity.

In addition to GF-binding and/or enhancement, the featured VN fragments can exhibit a certain degree of identity or homology to a corresponding wild type fragment of vitronectin. The extent of identity may be described not only in reference to the current polypeptides, but also in reference to the nucleic acid molecules that encode them. Biologically active variants of a fragment of vitronectin may differ from the wild type fragment by virtue of having one or more substitutions, additions or deletions of one or more amino acid residues. The substitutions can be conservative or non-conservative substitutions, and the amino acid side chains may also be modified.

Growth Factor Fragments:

Exemplary growth factor fragments featured in this invention include, but are not limited to, fragments of IGF-1, TGF-β1, TGF-β2, bFGF, FGF-7, PDGF-BB, VEGF-A, or NGF.

Growth factor fragments featured herein can be described in a variety of ways and with respect to various features. With respect to length, the featured fragments can have about, or less than about, 500 (e.g., 510, 505, 501, or no more than 498, 488, 478, 468, 458, 448, 438, or 428), 400 (e.g., 410, 405, 401, or no more than 398, 388, 378, 368, 358, 348, 338, or 328), 300 (e.g., 310, 305, 301, or no more than 298, 288, 278, 268, 258, 248, 238, or 228), 200 (e.g., 210, 205, 201, or about or no more than 198, 188, 178, 168, 158, 148, 138, or 128), 100, 75, 50, 45, 40, 35, 30, 28, 27, 26, or 25 amino acid residues. For example, the fragment can include no more than 25 or 26 amino acid residues (e.g., no more than 26 amino acid residues that are identical to 26 contiguous amino acid residues found in a naturally occurring growth factor protein).

In other embodiments, the fragment of a growth factor used in one or more of the various compositions described herein, or biologically active variants thereof, can have, or can include, an amino acid sequence conforming for Formula V:

(SEQ ID NO: 75)
$Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-

$Xaa_{11}$-$Xaa_{12}$-$Xaa_{13}$-$Xaa_{14}$-$Xaa_{15}$ (Formula V).

In Formula V, $Xaa_1$ can be Cys; $Xaa_2$ can be any amino acid residue; $Xaa_3$ can be any uncharged amino acid residue (e.g., Cys, Asn, Thr, or Val); $Xaa_4$ can be Arg; $Xaa_5$ can be any amino acid residue; $Xaa_6$ can be any amino acid residue; $Xaa_7$ can be any amino acid residue; $Xaa_8$ can be any amino acid residue; $Xaa_9$ can be any charged amino acid residue (e.g., Asp, Glu, Lys, or Arg); $Xaa_{10}$ can be any amino acid residue, $Xaa_{11}$ can be any amino acid residue (e.g., Asp, Arg, or Ser); $Xaa_{12}$ can be any amino acid residue; $Xaa_{13}$ can be any charged amino acid residue (e.g., Asp, Glu, or Arg); $Xaa_{14}$ can be any amino acid residue; $Xaa_{15}$ can be any non polar amino acid residue (e.g., Gly, Ile, Leu, or Pro). For example, the compositions of the invention can include a fragment of TGF-β1 that has, or that includes, the sequence CCVRQLYID-FRKDLG (SEQ ID NO:11). For example, the compositions of the invention can include a fragment of PDGF-BB that has, or that includes, the sequence CKTRTEVFEISRRLI (SEQ ID NO:12). For example, the compositions of the invention can include a fragment of FGF-2 that has, or that includes, the sequence CANRYLAMKEDGRLL (SEQ ID NO:31). For example, the compositions of the invention can include a fragment of VEGF-A that has, or that includes, the sequence CECRPKKDRARKENP (SEQ ID NO:13).

With respect to function, the featured GF fragments can bind a polypeptide provisional matrix molecule, e.g., fibronectin or vitronectin, with an affinity of about or at least about $1\times10^{-6}$-$1\times10^{-7}$ (e.g., about or at least about $5\times10^{-7}$; $1\times10^{-8}$; $5\times10^{-8}$; $1\times10^{-9}$; or $5\times10^{-9}$).

With respect to function, the featured GF fragments can be tested to determine inhibition of full-length growth factor binding to intact human plasma FN. The featured GF fragments can exhibit a certain degree of identity or homology to corresponding wild type fragments of growth factors. The extent of identity may be described not only in reference to the current polypeptides, but also in reference to the nucleic acid molecules that encode them. Biologically active variants of a fragment of a growth factor may differ from the wild type fragment by virtue of having one or more substitutions, additions or deletions of one or more amino acid residues. The substitutions can be conservative or non-conservative substitutions, and the amino acid side chains may also be modified.

Although applicants do not wish to be bound by theory, the fibronectin, vitronectin, or growth factor fragments described herein are useful in the treatment of skin-aging or photo-aging (e.g., for the treatment of wrinkles) and in other cosmetic treatments in that certain fragments derived from fibronectin and vitronectin have been shown to promote fibroblast survival and proliferation. Furthermore, fibronectin fragments may be used to deliver growth factors that promote fibroblast survival and proliferation to sites needing cosmetic treatment. For example, fibronectin fragments may be incorporated into transdermal patches or any other device to facilitate their delivery with or without growth factors. Growth factor fragments that inhibit fibronectin stimulation of specific growth factors (e.g., VEGF) may be useful, for example, in inhibiting UVB-induced angiogenesis, which has been linked to cutaneous photodamage (Yano et al., *Br. I. Dermatol.* 152(1):115-121, 2005).

Although applicants do not wish to be bound by theory, the fragments described herein (e.g., fibronectin fragments or vitronectin fragments) are useful in the treatment of wounds insofar as they stimulate fibroblast survival, proliferation and/or migration. Additionally, the fragments described herein (e.g., fibronectin fragments or vitronectin fragments) are useful, for example, as components of growth factor delivery devices such as engineered three-dimensional extracellular matrices.

The fragments described herein (e.g., growth factor fragments) are useful in the treatment of hyperproliferative disorders, e.g., cancer, in that they competitively inhibit binding of fibronectin to growth factors. Fibronectin both stimulates growth factor activity and localizes growth factors to tumors.

Consequently, the fragments described herein (e.g., growth factor fragments), may be used to inhibit excessive growth factor activity in a hyperproliferative disorder such as cancer.

Modifications of Fragments:

The featured fragments and biologically active variants thereof can be modified in numerous ways. For example, agents, including additional amino acid residues, other substituents, and protecting groups can be added to either the amino terminus, the carboxy terminus, or both. The modification can be made for the purpose of altering the fragments' form or altering the way the fragments bind to or interact with one another, with non-identical fragments, or with other polypeptides. For example, the fragments can be modified to include cysteine residues or other sulphur-containing residues or agents that can participate in disulphide bond formation. For example, one can add at least two cysteine residues, one or both of which are, optionally, at the C-terminal or N-terminal of the fragment.

The fragments can be cyclized by formation of a disulfide bond between cysteine residues (or, more generally, between two of the at least two cysteine residues present in the polypeptide (e.g., at the terminal regions)). While the peptides of the present invention may be linear or cyclic, cyclic peptides generally have an advantage over linear peptides in that their cyclic structure is more rigid and hence their biological activity may be higher than that of the corresponding linear peptide (see, generally, Camarero and Muir, *J. Am. Chem. Soc.* 121:5597-5598, 1999).

Strategies for the preparation of circular polypeptides from linear precursors have been described and can be employed with the present fragments. For example, a chemical cross-linking approach can be used to prepare a backbone cyclized version of the peptide (Goldenburg and Creighton, *J. Mol. Biol.*, 165:407-413, 1983). Other approaches include chemical intramolecular ligation methods (see, e.g., Camarero et al., *Angew. Chem. Int. Ed.*, 37:347-349, 1998; Tam and Lu, *Prot. Sci.*, 7:1583-1592, 1998; Camarero and Muir, *Chem. Commun.*, 1997:1369-1370, 1997; and Zhang and Tam, *J. Am. Chem. Soc.* 119:2363-2370, 1997) and enzymatic intramolecular ligation methods (Jackson et al., *J. Am. Chem. Soc.*, 117:819-820, 1995), which allow linear synthetic peptides to be efficiently cyclized under aqueous conditions. See also U.S. Pat. No. 7,105,341.

Alternatively, or in addition, any of the present fragments can further include one or more substituents. For example, the fragment can include a substituent at the amino-terminus, carboxy-terminus, and/or on a reactive amino acid residue side-chain. The substituent can be an acyl group or a substituted or unsubstituted amine group (e.g., the substituent at the N-terminus can be an acyl group and the C-terminus can be amidated with a substituted or unsubstituted amine group (e.g., an amino group having one, two, or three substituents, which may be the same or different)). The amine group can be a lower alkyl (e.g., an alkyl having 1-4 carbons), alkenyl, alkynyl, or haloalkyl group. The acyl group can be a lower acyl group (e.g., an acyl group having up to four carbon atoms), especially an acetyl group. The substituent can be a non-protein polymer, for example, a polyether, a polyethylene glycol (PEG), a polypropylene glycol, or a polyoxyalkylene, a polyalkylene glycol (for example, polypropylene glycol (PPG), a polybuylene glycol (PBG), or a PPG-PEG block/random polymer. The peptide can be modified by a non-protein polymer by methods known in the art and in the manner set forth in U.S. Pat. No. 4,640,835; 4,496,689; 4,301,144; 4,670,417; 4,791,192 or 4,179,337. The modification (e.g., PEGylation) can stabilize the peptide, reduce its antigenicity, decrease the required dosage, and/or augment its targeting ability.

The non-protein polymer can vary in size and shape. For example, any of the non-protein polymers listed above (e.g., PEG) can be linear, branched, or comb-shaped. Regarding size, the molecular weight can vary. For example, the PEG can have a molecular weight of, for example, about 300 kDa, about 1,000 kDa, about 2,000 kDa, about 3,000 kDa, about 4,000 kDa, about 5,000 kDa, about 6,000 kDa, about 7,000 kDa, about 8,000 kDa, about 9,000 kDa, about 10,000 kDa, about 11,000 kDa, about 12,000 kDa about 13,000 kDa about 14,000 kDa about 15,000 kDa, about 20,000 kDa, about 30,000 kDa, about 40,000 kDa, or about 50,000 kDa. For example, the PEG can be of a molecular weight anywhere in between 300 kDA and 2000 kDA, 300 kDA and 3000 kDA, 1000 kDA and 2000 kDA and 1000 and 3000 kDA.

The non-protein polymer (e.g., PEG) can be linked to the fragment by any number of functional group chemistries (e.g., carboxylated-mPEGs, p-nitrophenyl-PEGs, aldehyde-PEGs, amino-PEGs, thiol-PEGs, maleimide-PEGs, aminoxy-PEGs, hydrazine-PEGs, tosyl-PEGs, iodoacetamide-PEGs, succiminidylsuccinate-PEGs, succinimidylglutarate-PEGS, succinimidylcarboxypentyl-PEGs, p-nitrophenycarbonate-PEGs, or ethanethiol-PEGs). The non-protein polymer (e.g., PEG) can be linked to the fragment through any number of chemical groups including, but not limited to, amino-terminal amino acids, carboxy-terminal amino acids, free amines, and free sulfhydryl groups.

The non-protein polymer (e.g., PEG) may be a functionalized (for example, a monofunctional activated linear PEG, a homobifunctional activated linear PEG, a heterobifunctional activated linear PEG, a multiarmed activated PEG (e.g. 2-armed, 4-armed, 8-armed, etc.), a branched activated PEG and a comb-shaped activated PEG).

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "alkenyl" refers to an alkyl group having one or more double carbon-carbon bonds. Example alkenyl groups include ethenyl, propenyl, and the like. "Alkynyl" refers to an alkyl group having one or more triple carbon-carbon bonds. Example alkynyl groups include ethynyl, propynyl, and the like. "Haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "polyether" refers to a polymer containing ether linkages. Examples include polyethylene glycol.

As noted, the fragments can vary in length and can be or can include contiguous amino acid residues that naturally occur in fibronectin, vitronectin, or growth factors or that vary to a certain degree from naturally occurring fibronectin, vitronectin, or growth factor sequences (but retain sufficient activity to be useful). Where the fragments include, at their N-terminus or C-terminus (or both), amino acid residues that are not naturally found in fibronectin, vitronectin, or a growth factor, the additional sequence(s) can be about 200 amino acid residues long, and these residues can be divided evenly or unevenly between the N- and C-termini. For example, both the N- and C-termini can include about 10, 20, 30, 40, 50, 60, 70, 80, 90, or 100 amino acid residues. Alternatively, one terminus can include about 10, 20, 30, 40, 50, 60, 70, 80, 90, 100, 110, 120, 130, 140, 150, 160, 170, 180, 190, or 200 residues, and one terminus can include none (e.g., it can terminate in an amino acid sequence identical to a naturally occurring fibronectin, vitronectin, or a growth factor sequence).

More specifically, the N- or C-termini can include 1 to about 100 (e.g., 1, 2, 3, 4, 5, 6, 7, 8, 9, 10, 15, 20, 25, 30, 40, 50, 60, 70, 80, 90, or 100) amino acid residues that are positively charged (e.g., basic amino acid residues such as arginine, histidine, and/or lysine residues); 1 to about 100 amino acid residues that are negatively charged (e.g., acidic amino acid residues such as aspartic acid or glutamic acid residues); 1 to about 100 glycine residues; 1 to about 100 hydrophobic amino acid residues (e.g., hydrophobic aliphatic residues such as alanine, leucine, isoleucine or valine or hydrophobic aromatic residues such as phenylalanine, tryptophan or tyrosine); or 1 to about 100 (e.g., 1-4) cysteine residues.

The fragments, including the modified fragments described above, can be protease resistant and can include one or more types of protecting groups such as an acyl group, an amide group, a benzyl or benzoyl group, or a polyethylene glycol. More specifically, a fragment, including the modified fragments described above, can be N-terminally acetylated and/or C-terminally amidated.

Where non-naturally occurring or modified amino acid residues are included they can be selected from the following or many others available in the art: 4-hydroxyproline, gamma-carboxyglutamic acid, o-phosphoserine, o-phosphotyrosine, or delta-hydroxylysine. Other examples include naphthylalanine, which can be substituted for trytophan to facilitate synthesis, L-hydroxypropyl, L-3,4-dihydroxyphenylalanyl, alpha-amino acids such as L-alpha-hydroxylysyl and D-alpha-methylalanyl, L-alpha-methylalanyl, beta-amino acids, and isoquinolyl. Fragments having non-naturally occurring amino acid residues may be referred to as synthetic fragments and constitute one type of variant as described herein. Other variants include fragments in which a naturally occurring side chain of an amino acid residue (in either the L- or D-form) is replaced with a non-naturally occurring side chain.

In one embodiment, the fragments can have three extra amino acids (MetGlySer) at either terminus (or both) (e.g., at the N-terminus) and seven to eight extra amino acids (ThrSer-HisHisHisHisHisHisCys (SEQ ID NO:14)) at either terminus (or both) (e.g., at the C-terminus).

For guidance on fragment modification by reduction/alkylation and/or acylation, one can consult Tarr, *Methods of Protein Microcharacterization*, J. E. Silver ed., Humana Press, Clifton N.J. 155-194, 1986; for guidance on chemical coupling to an appropriate carrier, one can consult Mishell and Shiigi, eds, *Selected Methods in Cellular Immunology*, WH Freeman, San Francisco, Calif. (1980) and U.S. Pat. No. 4,939,239; and for guidance on mild formalin treatment, one can consult Marsh, *Int. Arch. of Allergy and Appl. Immunol.*, 41:199-215, 1971.

Any of the fragments (FN, VN, or GF) in the featured compositions can be one of a plurality present in a multimeric form (e.g., a dimer). These multimers can be linear or branched. The multimeric form can also include one or more types of fragments and a backbone structure. Where two or more fragments are present, they may be identical or non-identical. A smaller structure, referred to as a linker, may also be present and may mediate attachment of the fragments to the backbone. Generally, the linker is smaller than the backbone. The nature of the backbone structure is not critical, and many different types of molecules may be used. One example of a linker structure is an oligolysine molecule having, for example, two or more lysine residues (e.g., 2, 3, 4, or more lysine residues). Two or more fragments of the invention (e.g., two three or four polypeptides) may be attached to lysine residues by, for example, peptide bonds. These fragments, having a polylysine linker, can be linked to a backbone structure. For example, the invention encompasses:

```
                                          (SEQ ID NO: 15)
Backbone-KKKQLISIQQYGHQEVTRFDFTTTSTST
and
                                          (SEQ ID NO: 16)
QLISIQQYGHQEVTRFDFTTTSTSTKKK-Backbone.
```

A backbone structure, for example, an oligolysine molecule, may be linear or branched. A multimeric peptide of the invention on a branched backbone molecule may be referred to herein as a "dendrimeric" peptide.

Any of the fragments described herein, including the variant forms described herein, can further include a heterologous polypeptide (i.e., a polypeptide having a sequence that does not appear in a fibronectin, vitronectin, or a growth factor). The heterologous polypeptide can be a polypeptide that increases the circulating half-life of the fragment to which it is attached (e.g., fused, as in a fusion protein). The heterologous polypeptide can be an albumin (e.g., a human serum albumin or a portion thereof) or a portion of an immunoglobulin (e.g., the Fc region of an IgG).

Polypeptide growth factors that can be bound by the FN or VN fragments described herein can be within the insulin-like growth factor (IGF) family (e.g., IGF-1), within the transforming growth factor (TGF) family (e.g., TGF-β1 or TGF-β2), within the fibroblast growth factor (FGF) family (e.g. bFGF or FGF-7), within the platelet-derived growth factor (PDGF) family (e.g., PDGF-BB), within the vascular endothelial growth factor (VEGF) subfamily (e.g., VEGF-A), or within the nerve growth factor (NGF) family. Fragments of these growth factors may be tested for binding to FN or VN. To determine whether fibronectin or vitronectin fragments bind growth factors that have retained a biological activity, standard biological assays can be carried out. For example, as outlined in the Examples below, migratory responses to bound growth factors that usually stimulate migration can be carried out. For example, one can compare the effect of a bound and unbound growth factor on fibroblast migration or granulation tissue formation. Specifically, if a growth factor is a PDGF (e.g., PDGF-BB), migration of AHDF cells can be analyzed.

To determine whether a growth factor fragment competes with a full-length growth factor for binding to fibronectin or vitronectin, a binding assay can be carried out. For example, as outlined in the Examples below, a labeled growth factor may be incubated with immobilized fibronectin in the presence and absence of a growth factor fragment. If the fragment reduces the amount of labeled full-length growth factor bound to the immobilized fibronectin, then the fragment competes with the full-length growth factor for binding to fibronectin.

Compounds mimicking the necessary conformation of the fragments (of fibronectin, vitronectin, and growth factors) described herein are contemplated as within the scope of this invention. A variety of designs for such mimetics are possible. U.S. Pat. No. 5,192,746; U.S. Pat. No. 5,169,862; U.S. Pat. No. 5,539,085; U.S. Pat. No. 5,576,423; U.S. Pat. No. 5,051, 448; and U.S. Pat. No. 5,559,103, all hereby incorporated by reference, describe multiple methods for creating such compounds.

Synthesis of non-peptide compounds that mimic peptide sequences is also known in the art (see, e.g., Eldred et al. (*J. Med. Chem.* 37:3882, 1994; Ku et al. (*J. Med. Chem.* 38:9, 1995). Such nonpeptide compounds that mimic fibronectin fragments that bind growth factors or enhance their activity are specifically contemplated by the present invention.

With this method, peptides can be readily synthesized by a solid phase method by adding amino acids stepwise to a growing peptide chain that is linked to an insoluble matrix, such as polystyrene beads. The carboxyl-terminal amino acid (with an amino protecting group) of the desired peptide sequence is first anchored to the polystyrene beads. The protecting group of the amino acid is then removed. The next amino acid (with the protecting group) is added with the coupling agent. This is followed by a washing cycle. The cycle is repeated as necessary.

In one embodiment, the mimetics of the present invention are peptides having sequence homology to the herein-described fibronectin fragments. In another embodiment, the mimetics of the present invention are peptides having sequence homology to the herein described vitronectin fragments. In yet another embodiment, the mimetics of the present invention are peptides having sequence homology to the herein described growth factor fragments. These mimetics include, but are not limited to, peptides in which L-amino acids are replaced by their D-isomers. One common methodology for evaluating sequence homology, and more importantly statistically significant similarities, is to use a Monte Carlo analysis using an algorithm written by Lipman and Pearson to obtain a Z value. According to this analysis, a Z value greater than 6 indicates probable significance, and a Z value greater than 10 is considered to be statistically significant (Pearson and Lipman, *Proc. Natl. Acad. Sci. (USA)*, 85:2444-2448, 1988; Lipman and Pearson, *Science*, 227: 1435-1441, 1985). More generally, the FN, VN, and GF fragments described herein and the mimetics described above can be synthesized using any known methods, including tea-bag methodology or solid phase peptide synthesis procedures described by Merrifield et al. (*Biochemistry* 21:5020-5031, 1982), Houghten Wellings (*Proc. Natl. Acad. Sci. (USA)* 82:5131-5135, 1985); Atherton, *Methods in Enzymology* 289: 44-66, 1997, or Guy and Fields, *Methods in Enzymology* 289:67-83, 1997, or using a commercially available automated synthesizer.

In certain embodiments, the mimetic is a multimer of a fragment (e.g., a fibronectin fragment, e.g., a vitronectin fragment, or, e.g., a growth factor fragment). In certain embodiments, the multimer is a polypeptide including the repeated amino acid sequence of a fragment (e.g., a fibronectin fragment). Peptides can be synthesized by linking an amino group to a carboxyl group that has been activated by reaction with a coupling agent, such as dicyclohexylcarbodiimide (DCC). The attack of a free amino group on the activated carboxyl leads to the formation of a peptide bond and the release of dicyclohexylurea. It can be necessary to protect potentially reactive groups other than the amino and carboxyl groups intended to react. For example, the (α-amino group of the component containing the activated carboxyl group can be blocked with a tertbutyloxycarbonyl group. This protecting group can be subsequently removed by exposing the peptide to dilute acid, which leaves peptide bonds intact.

Physiologically Acceptable Compositions:

A present pharmaceutical composition is formulated to be compatible with its intended route of administration, for example, oral or parenteral (e.g., intravenous, intradermal, subcutaneous, intraperitoneal, intramuscular, by inhalation, transdermal (topical), and transmucosal administration). Given the ability of the present FN fragments, and GF-containing complexes bearing these fragments, to facilitate wound healing, topical formulations are particularly envisioned. Solutions or suspensions used for parenteral administration can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The composition can be aliquoted or packaged in ampules, disposable syringes, single or multiple dose vials made of glass or plastic, bottles, and the like, and such packaged forms, along with instructions for use, are within the scope of the present invention. Preferably, the compositions are sterile at a medically acceptable level in view of the intended route of administration.

Pharmaceutical compositions adapted for topical administration may include, but are not limited to, compositions in the form of skin care, skin cleansing, or anti-wrinkle products, shampoos, make-up, conditioners, lotions, aerosols, gels, mousses, dyes, or bleaches. These compositions may contain one or more conventional cosmetic or dermatological additives or adjuvants, including, but not limited to, fillers, surfactants, thixotropic agents, antioxidants, preserving agents, dyes, pigments, fragrances, thickeners, vitamins, hormones, moisturizers, UV absorbing organic sunscreens, UV scattering inorganic sunscreens, wetting agents, cationic, anionic, nonionic or amphoteric polymers, and hair coloring active substances. These adjuvants are well known in the field of cosmetics and are described in many publications, for example see Harry's Book of Cosmetology, 8.sup.th edition, Martin Rieger, ed., Chemical Publishing, New York (2000). Exemplary compositions are described in, for example, in U.S. Pat. Application 2005008604, U.S. Pat. Application 20050025725 and U.S. Pat. Application 20040120918 which are herein incorporated by reference.

In certain embodiments, the pharmaceutical compositions of this invention can include one or more chemical penetration enhancers (as described, for example, in International Publication No. WO2005009510).

Exemplary chemical penetration enhancers include, but are not limited to, 1-dodecyl pyrrolidone, benzyl dimethyl dodecyl ammonium chloride, cocamidopropyl betaine, cocamidopropyl hydroxysultaine, oleyl betaine, cineole, cetyl trimethyl ammonium bromide, dodecyl amine, dodecyl pyridinium chloride, hexadecyl trimethyl ammoniopropane sulfonate, isopropyl myristate, lauric acid, limonene, linoleic acid, linolenic acid, menthol (terpene), methyl laurate, 1-methyl-2-pyrrolidone, N-lauryl sarcosine (CAS number 137-16-6, also called sodium lauroyl sarcosinate), nicotine sulfate, oleic acid, octyl trimethyl ammonium bromide, polyethyleneglycol dodecyl ether, 1-phenyl piperazine, sorbitan monolaurate, sodium lauryl ether sulfate, sodium dodecyl sulfate, sodium oleate, sodium octyl sulfate, tetracaine, and Tween-20™.

Chemical penetration enhancers increase skin permeability and are known in the art (see, for example, Shah et al. "Skin Penetration Enhancement: Clinical pharmacological and regulatory considerations." Pharmaceutical Skin Penetration Enhancement, ed. K. Walters. 1993, New York, Basel, Hong Kong: Marcel Dekker. 417-427).

The present peptides may be used in cosmetic compositions either as themselves peptides themselves or in the form of a premix in a suitable excipient and they may be used in the form of a solution, dispersion, emulsion, paste or powder. They may individually or with other active substances, including but not limited to those specifically described herein, be carried by cosmetic vectors such as macro-, micro- or nanocapsules, liposomes or chylomicrons, macro-, micro- or nanoparticles or microsponges. They may also be adsorbed on powdered organic polymers, talcs, bentonites and other inorganic carriers.

The peptides may be used in any form or in a form that is bound, incorporated, absorbed in or adsorbed on macro-, micro- and nanoparticles, macro-, micro- and nanocapsules for the treatment of textiles, synthetic or natural fibers, wools and all materials liable to be used in the manufacture of clothing or underwear for the day or night, intended for contact with the skin, such as pantyhose, underwear, handkerchiefs and wipes, in order to exert a cosmetic effect through the contact between the textile and skin and enable continuous topical delivery.

The peptides can be used in compositions (e.g., therapeutic or cosmetic compositions) at concentrations ranging from 0.00001% (w/w) ("w/w" is weight/weight) and 10% (w/w) (e.g., between about 0.0001% (w/w) and 1% (w/w)). Another useful range is from about 0.001% and about 5% (w/w). The peptides may also be used in the range of about 1 ppm to about 500 ppm (e.g., about 100 to about 400 ppm). Where ceramide is included, it can be present at between about 1 and about 8% (w/w).

Pharmaceutical compositions adapted for injection include, for example, sterile aqueous solutions (where water soluble) or dispersions and sterile powders for the extemporaneous preparation of sterile injectable solutions or dispersion. For intravenous administration, suitable carriers include, for example, physiological saline, bacteriostatic water, Cremophor EL™ (BASF, Parsippany, N.J.) and phosphate buffered saline (PBS). In all cases, the compositions prepared for administration should be sterile and should be fluid or convertible to a fluid at least sufficient for easy syringability. The composition and/or nucleic acid constructs should be stable under the conditions of manufacture and storage and should be preserved against the contaminating action of microorganisms such as bacteria and fungi. Preservatives against microorganisms can include various antibacterial and antifungal agents, for example, parabens, chlorobutanol, phenol, ascorbic acid, thimerosal, and the like.

The carrier can be a solvent or dispersion medium containing, for example, water, ethanol, polyol (for example, glycerol, propylene glycol, and liquid polyetheylene glycol, and the like), and suitable mixtures thereof. Fluidity can be maintained, for example, by the use of a coating such as lecithin, by the maintenance of the required particle size in the case of dispersions and by the use of surfactants.

In many cases, it will be desirable for the composition to be isotonic to blood. This can be accomplished using various isotonic agents, for example, sugars, polyalcohols such as manitol, sorbitol, sodium chloride in the composition.

Delayed or extended absorption of the injectable compositions can be desirable and can be achieved by including in the composition an agent which delays absorption, for example, aluminum monostearate and gelatin, or by coating micro- or nano-particles of active agent in the composition with materials that delayed or extended release of components.

Sterile injectable solutions can be prepared, for example, by solubilizing or suspending the active compound in the required amount in an appropriate solvent with one or a combination of additional ingredients. Typically creation of such solution or suspension is followed by sterile filtration. Generally, dispersions are prepared by incorporating the active compound into a sterile vehicle which contains a basic dispersion medium and the other desired ingredients. In the case of sterile powders for the preparation of sterile injectable solutions, the preparation is dried, e.g., by vacuum drying and/or freeze-drying.

Compositions for oral administration typically include an inert or edible diluent or edible carrier. Such compositions can be formulated in various ways, e.g., in liquid, capsule, or tablet form. Pharmaceutically compatible binding agents, and/or adjuvant materials can be included as part of the composition. The tablets, pills, capsules, troches and the like can contain any one or more of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For inhalation administration (e.g., for application to cancerous cells within the nasal passages, nasopharynx, trachea or lungs or for application to wounded tissues (e.g., mucosa) in these regions), the present compositions are delivered in the form of a wet or dry aerosol spray, e.g., from a pressured container or dispenser which contains a suitable propellant, e.g., a gas such as carbon dioxide, or a nebulizer.

Systemic administration can also be by transmucosal or transdermal routes. For transmucosal or transdermal administration, penetrants appropriate to the barrier to be permeated are typically used in the formulation. A number of such penetrants are generally known in the art, and include, for example, for transmucosal administration, detergents, bile salts, and fusidic acid derivatives. Administration may also be facilitated by iontophoresis, microneedles and other devices designed to enhance transdermal penetration.

Transmucosal administration can be accomplished through the use of nasal sprays or suppositories (e.g., using conventional suppository bases such as cocoa butter and other glycerides). For transdermal administration, the active compounds are formulated into ointments, salves, gels, or creams as generally known in the art.

Such compositions can also be formulated with carriers that will protect the compositions against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polycarbonates, and polylactic acid. The materials can also be obtained commercially, e.g., from Alza Corporation and Nova Pharmaceuticals, Inc. Liposomal suspensions (including liposomes targeted to particular cells (e.g., targeted to infected cells) with monoclonal antibodies) can also be used to prepare pharmaceutical compositions. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of active compounds and pharmaceutical compositions can be determined by standard pharmaceutical procedures in cell cultures or experimental animals. For example, such procedures are routinely applied for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are generally preferred. The data obtained from the cell culture assays and animal studies (including those described in the examples, below) can be used in formulating a range of dosage for use in humans or other intended subject. The dosage of such compounds is usually selected to produce a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. Thus, for example, a dose may be initially established in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography, or by other suitable analysis method adapted for the compound of interest.

As noted, peptides (e.g., synthetic or recombinantly produced peptides) with growth factor-binding and/or -enhancing activity can be incorporated into a tissue engineered product. FN domains that promote fibroblast migration can also be included. Preferably, the products are robust (i.e., relatively resistant to rapid degradation). They can be used, for example, in treating wounds, including acute or non-healing wounds (e.g., chronic ulcers). Patients amenable to treatment are described further below. Alternatively or in addition, growth factor-binding and/or enhancing peptides can be tethered to a biocompatible polymer for delivery of one or more growth factors to a cell, tissue or organ in need of treatment or for endogenous localization of growth factors. Alternatively or in addition, growth factor-binding and/or enhancing peptides can be incorporated in a polymer or nonpolymer biomaterial for controlled release to an acute or non-healing wound.

We have developed an engineered ECM that is conductive and inductive of new tissue formation in porcine cutaneous wounds utilizing molecular domains C, H, and HV of the blood protein fibronectin (FN) tethered to an intramolecularly crosslinked hyaluronan (HA) hydrogel. Thus, in one implementation, the invention includes an engineered ECM that includes a fragment of a fibronectin (e.g., a plasma fibronectin) or a biologically active variant thereof. Furthermore, the invention can include a fragment of vitronectin. The fragment can be tethered to (e.g., covalently or non-covalently bound to) a hydrogel (e.g., an HA hydrogel) and can be a fragment that binds and/or enhances a polypeptide growth factor. The fragment can be tethered according to attachment methods discussed in U.S. Pat. Application 20050282747, the contents of which are incorporated herein in their entirety.

The naturally-occurring ECM is comprised of diverse constituents such as glycoproteins, proteoglycans, complex carbohydrates, and other molecules. Major functions of the ECM include, but are not limited to, providing structural support, tensile strength or cushioning; providing substrates and pathways for cell adhesion and cell migration; and regulating cellular differentiation and metabolic function. ECM proteins include, for example, collagens, elastin, fibronectin, laminin, proteoglycans, vitronectin, thrombospondin, tenascin (cytoactin), entactin (nidogen), osteonectin (SPARC), anchorin CII, chondronectin, link protein, osteocalcin, bone sialoprotein, osteopontin, epinectin, hyaluronectin, amyloid P component, fibrillin, merosin, s-laminin, undulin, epilligrin, and kalinin.

The featured tissue engineered product (e.g., the engineered ECM) can include biological and/or synthetic components. It can include a biopolymer (e.g., hyaluronan (HA), a glycosaminoglycan (GAG), fibrinogen, laminin, or collagen). The biocompatible polymer can be a synthetic biodegradable polymer, many of which are known in the art. For example, the biodegradable polymer can be a poly(lactide), a poly(glycolide), a poly(lactide-coglycolide), a poly(lactic acid), a poly(glycolic acid), a poly(lactic acid-co-glycolic acid), a poly(caprolactone), a polycarbonate, a polyesteramide, a polyanhydride, a poly(amino acid), a poly(ortho ester), a polycyanoacrylate, a polyamide, a polyacetal, a poly(ether ester), a copolymer of poly(ethylene glycol) and a poly(ortho ester), a poly(dioxanone), a poly(alkylene alkylate)s, a biodegradable polyurethane, or any blend or copolymer thereof. Other useful polymers include an alginate polymer and a carboxy-vinyl polymer (e.g., a polymer including at least 90% acrylic acid monomers and about 0.1% to about 5.0% of a difunctional crosslinking agent).

A tissue engineered "smart" matrix that would be conductive and inductive of tissue cell repopulation of a wound site and the development of new tissue, respectively, can be composed of GFs, or active fragments thereof, in the context of an appropriate ECM that are required for optimal wound repair. In addition, FN and VN OF-binding domain(s) may provide a useful tool for engineering many other GF localization (from endogenous or exogenous sources) and/or delivery systems for soft or hard tissue repair, augmentation and regeneration. Furthermore, growth factor FN/VN-binding peptides or molecularly engineered derivatives of the FN and VN GF-binding domains might become strongly inhibitory of GF activity and thus useful for proliferative or fibrotic disorders such as cancer, pulmonary fibrosis, GI or GU stenosis, burn contractures and autoimmune generated sclerosis.

EngECM can be generated with or without growth factors, or active fragments thereof (e.g., growth factors and fragments described herein). In the former case, the dosage of growth factors in the engECM can vary, e.g., as described below, 100 ng/ml (15 ng total per wound) of PDGF-BB added to 2:1 engineered ECM enhanced granulation formation at 4 days after injury and application of material. In the latter case, when placed in the vicinity of an endogenous supply of growth factors, the growth factors can be recruited by the matrix.

The invention further encompasses nucleic acid molecules, including DNA and RNA molecules, that encode the polypeptides described herein. For example, a nucleic acid molecule can encode the C, H, or HV domains or portions thereof for inclusion in engineered ECMs; $FNIII_{1-2}$ or a portion thereof; $FNIII_I$ or a portion thereof; $FNIII_2$ or a portion thereof; $FNIII_{12-V15}$ or a portion thereof; $FNIII_{12-15}$ or a portion thereof; FNIII$_{12-14}$ or a portion thereof; FNIII$_{12-13}$ or a portion thereof; FNIII$_{13-14}$ or a portion thereof; IIICS or a portion thereof.

The nucleic acid molecules can be formulated in physiologically acceptable compositions for administration.

The invention also features vectors that include the present nucleic acid constructs. Of particular benefit are expression vectors, especially those for expression in eukaryotic cells. Such vectors can, for example, be viral, plasmid, cosmid, or artificial chromosome (e.g., yeast artificial chromosome) vectors.

Typically, plasmids are circular, dsDNA elements that include one or more cloning sites for insertion of selected DNA sequences, e.g., coding sequences. Such plasmids may include a functional origin of replication and thus are replication competent, or may be replication defective.

In addition to plasmids, viral vectors (e.g., replication defective retroviruses, lentiviruses, adenoviruses and adeno-associated viruses) can also be advantageously used. A large number of such viral vectors have been developed having a broad variety of different properties. For example, such viral vectors may be replication defective retroviruses, adenoviruses and adeno-associated viruses. Techniques and procedures for producing recombinant retroviruses and for infecting cells in vitro or in vivo with such viruses are provided in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include psi.Crip, psi.Cre, psi.2 and psi.Am.

The genome of adenovirus can be manipulated such that it encodes and expresses a nucleic acid construct, as described herein, but is inactivated in terms of its ability to replicate in a normal lytic viral life cycle. (see, e.g., Berkner et al., *Bio-Techniques* 6:616, 1988; Rosenfeld et al., *Science* 252:431-434, 1991; and Rosenfeld et al., *Cell* 68:143-155, 1992). Suitable adenoviral vectors derived from the adenovirus strain Ad type 5 d1324 or other strains of adenovirus (e.g., Ad2, Ad3, Ad7 etc.) are well known to those skilled in the art. Alternatively, an adeno-associated virus vector such as that described in Tratschin et al. (*Mol. Cell. Biol.* 5:3251-3260, 1985) can be used to express a transactivator fusion protein.

Other viral vector alternatives include lentiviral vectors. Such vectors and their preparation and use are described, for example, in U.S. Pat. Nos. 6,924,123; 6,863,884; 6,830,892; 6,818,209; 6,808,923; 6,799,657, all of which are incorporated herein in their entireties.

The vectors of the invention can advantageously include a polypeptide fragment described herein. Other elements included in the design of a particular expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The vectors described herein can be introduced into cells or tissues by any one of a variety of known methods within the art. Such methods are described for example in Sambrook et al., *Molecular Cloning: A Laboratory Manual*, Cold Spring Harbor Laboratory, New York (1992), which is hereby incorporated by reference. See, also, Ausubel et al., *Current Protocols in Molecular Biology*, John Wiley and Sons, Baltimore, Md. (1989); Hitt et al., "Construction and propagation of human adenovirus vectors," in *Cell Biology: A Laboratory Handbook*, Ed. J. E. Celis., Academic Press. 2$^{nd}$ Edition, Volume 1, pp: 500-512, 1998; and Hitt et al., "Techniques for human adenovirus vector construction and characterization," in *Methods in Molecular Genetics*, Ed. K. W. Adolph, Academic Press, Orlando, Fla., Volume 7B, pp: 12-30, 1995. The methods include, for example, stable or transient transfection, lipofection, electroporation and infection with recombinant viral vectors. The term "transfecting" or "transfection" is intended to encompass all conventional techniques for introducing nucleic acid into host cells, including calcium phosphate co-precipitation, DEAF-dextran-mediated transfection, lipofection, electroporation and microinjection. Suitable methods for transfecting host cells can be found in Sambrook et al. (Molecular Cloning: A Laboratory Manual, 2nd Edition, Cold Spring Harbor Laboratory press (1989)), and other laboratory textbooks.

For plant cells, a Ti plasmid or viral vector is often used. For example, such plasmids and viral vectors can be used to transfect host plant cells via *Agrobacterium tumefaciens*-mediated transfection (for plant cells susceptible to *A. tumefaciens* infection), or can be directly inserted in cells, e.g., using microinjection, particle bombardment, or electroporation. In other methods, protoplasts can be made from plant cells and then transfected.

The number of host cells transformed with a nucleic acid constructs of the invention will depend, at least in part, upon the type of recombinant expression vector and the type of transfection technique used. Nucleic acid can be introduced into a host cell transiently, or for long-term expression. For long-term expression, the nucleic acid is stably integrated into the genome of the host cell or remains as a stable episomal element.

For integration of nucleic acid into host cell DNA, typically a gene is used that encodes a selectable marker (e.g., drug resistance) is introduced into the host cells along with the nucleic acid of interest. A variety of such selectable markers are commonly used, such as the drugs hygromycin and neomycin. Selectable markers can be introduced on a separate plasmid or other vector from the nucleic acid of interest or, are introduced on the same vector. Host cells transfected with a nucleic acid construct of the invention (e.g., a recombinant expression vector) and a gene for a selectable marker can be identified by selecting for cells using the selectable marker.

The present nucleic acid constructs can be introduced into eukaryotic cells growing in culture in vitro by conventional transfection techniques (e.g., calcium phosphate precipitation, DEAE-dextran transfection, electroporation, and other methods). Cells can also be transfected in vivo, for example by application of a delivery mechanism suitable for introduction of nucleic acid into cells in vivo, such as viral vectors (see e.g., Ferry et al., *Proc. Natl. Acad. Sci. USA* 88:8377-8381, 1991, and Kay et al., *Human Gene Therapy* 3:641-647, 1992), adenoviral vectors (see e.g., Rosenfeld, *Cell* 68:143-155, 1992; and Herz and Gerard, *Proc. Natl. Acad. Sci. USA* 90:2812-2816, 1993), receptor-mediated DNA uptake (see e.g., Wu and Wu, *J. Biol. Chem.* 263:14621, 1988; Wilson et al., *J. Biol. Chem.* 267:963-967, 1992; and U.S. Pat. No. 5,166,320), direct injection of DNA (see e.g., Acsadi et al., *Nature* 332:815-818, 1991; and Wolff et al., *Science* 247: 1465-1468, 1990) or particle bombardment (see e.g., Cheng et al., *Proc. Natl. Acad. Sci. USA* 90:4455-4459, 1993; and Zelenin et al., *FEBS Letters* 315:29-32, 1993). Thus, in the present invention, cells can be transfected in vitro or ex vivo, and the expressed peptide can be isolated therefrom by methods known in the art. The cells can also be administered to a subject or, alternatively, cells can be directly modified in vivo.

In any of these situations, the nucleic acid construct used to express the peptide can include a signal sequence to facilitate export from the cell.

Another aspect of the invention pertains to host cells into which a nucleic acid construct of the invention has been introduced, i.e., a "recombinant host cell." It is understood that the term "recombinant host cell" refers not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell, although eukaryotic cells are preferred. Exemplary eukaryotic cells include mammalian cells (such as Chinese hamster ovary cells (CHO) or COS cells). Other suitable host cells are known in the art.

It is not intended that the present invention be limited by the particular nature of the therapeutic preparation, so long as the preparation comprises an appropriate fragment of fibronectin and/or vitronectin that binds a polypeptide growth factor or that has intrinsic survival or growth factor activity or an appropriate fragment of a growth factor that binds fibronectin and/or vitronectin. For example, such compositions can be provided together with physiologically tolerable liquid, gel or solid carriers, diluents, adjuvants and/or excipients.

These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts.

Such compositions are typically prepared as liquid solutions or suspensions, or in solid forms. Formulations can include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%-95% of active ingredient, preferably 2%-70%.

The compositions are also prepared as injectables, either as liquid solutions or suspensions; solid forms suitable for solution in, or suspension in, liquid prior to injection may also be prepared.

The fragments of the present invention are often mixed with diluents or excipients which are physiological tolerable and compatible. Suitable diluents and excipients are, for example, water, saline, dextrose, glycerol, or the like, and combinations thereof. In to addition, if desired the compositions may contain minor amounts of auxiliary substances such as wetting or emulsifying agents, stabilizing or pH buffering agents.

Additional formulations which are suitable for other modes of administration, such as topical administration, include salves, tinctures, creams, lotions, and, in some cases, suppositories. For salves and creams, traditional binders, carriers and excipients may include, for example, polyalkylene glycols or triglycerides.

Methods of Use:

The fibronectin, vitronectin, and growth factor fragments described herein are useful in the treatment of cancer, in promoting tissue regeneration, e.g., wound healing, and in cosmetic and therapeutic formulations for the prevention and treatment of poor skin appearance related to, for example, aging. Use in cell culture is also described. The polypeptides (or nucleic acids or expression vectors encoding them or cells expressing them) can be incorporated into, for example, therapeutic formulations for the indications described herein as well as into products and compositions for improving, for example, skin appearance and/or feel of skin exhibiting signs of skin aging.

For example, preferred compositions of the present invention are useful for regulating the appearance of skin due to wrinkles and UVB photodamage by providing visual improvement in skin appearance following application of the composition to the skin. Generally speaking, compositions of the present invention which further contain particulate materials will be most useful for providing the immediate visual improvement.

The invention features cosmetic treatments including those for prophylactically regulating a skin condition and those for therapeutically regulating a skin condition. "Signs of skin aging," "poor skin appearance," and other phrases similarly referring to, for example, symptoms of aging and the like include, but are not limited to, all outward visibly and tactilely perceptible manifestations as well as any other macro or micro effects due to skin aging. Such signs may be induced or caused by intrinsic factors and/or extrinsic factors, e.g., chronological aging and/or environmental damage (e.g., UVB photodamage, exposure to pollutants, and poor diet). These signs may result from processes which include, but are not limited to, the development of textural discontinuities such as wrinkles and coarse deep wrinkles, skin lines, crevices, bumps, large pores (e.g., associated with adnexal structures such as sweat gland ducts, sebaceous glands, or hair follicles), or unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin. Particularly preferred in accordance with the present invention, the signs of skin aging are wrinkles and the compositions of the present invention are, in certain preferred embodiments, useful in fighting, treating or preventing wrinkles.

Wrinkles can result from numerous causes. For example, wrinkles can be caused from the natural aging process of the skin, from smoking, and from exposure to ultraviolet radiation (e.g., from chronic sun exposure). Wrinkles can be classified as described in Kligman et al. (*Br. J. Derm.* 113:37-42, 1985), herein incorporated by reference. Kligman classifies wrinkles into three classes: linear wrinkles, glyphic wrinkles, and crinkles, and any of these types of wrinkles, regardless of their cause, can be treated as described herein. Aside from wrinkles per se, the present compositions can be used to improve the skin's appearance.

The methods disclosed herein are useful to prevent or treat or reduce wrinkles, including UV-induced wrinkles, and/or to improve skin quality and appearance in a subject. The methods can be carried out by administering to the subject a composition containing a fibronectin fragment, a vitronectin fragment, or a growth factor, or a biologically active variant thereof. An exemplary treatment method can include locating a wrinkle or a potential site of wrinkling and applying a composition described herein.

As used herein, prophylactically regulating a skin condition includes delaying, minimizing and/or preventing visible and/or tactile discontinuities in skin (e.g., texture irregularities in the skin which may be detected visually or by feel), including signs of skin aging.

As used herein, therapeutically regulating skin condition includes ameliorating, e.g., diminishing, minimizing and/or effacing, discontinuities in skin, including signs of skin aging. Some of the products produced using the compositions of the present invention and indeed the compositions themselves may be used for prophylactically or therapeutically regulating a skin condition.

In certain preferred aspects, the present invention is useful for improving the physiological state and/or the physical appearance of human skin, in particular to reduce the signs of skin aging that are generated by sun exposure (e.g., UVB photodamage), physical and hormonal stress, abrasion, nutritional effects and other similar causes. The compositions may often be used to prevent the signs of aging and/or to treat them in order to afford the consumer who uses them, a more youthful appearance.

All terms such as "skin aging," "signs of skin aging," "poor skin appearance," "topical application," and the like are used in the sense in which they are generally and widely used in the art of developing, testing and marketing cosmetic and personal care products. "Wrinkles" means furrows in the otherwise smooth surface of the facial skin, visible to the naked eye, in the average depth of 50 to more than 200 µm and essentially appearing with progressive age. The term "cosmetic composition" in accordance with the present invention relates to a formulation that can be used for cosmetic purposes, purposes of hygiene or as a basis for delivery of one or more pharmaceutical ingredients. This includes cosmetics, personal care products and pharmaceutical preparations. It is also possible that these formulations are used for two or more of these same purposes at one time. A medicated dandruff shampoo, for example, has pharmacological properties and is used as a personal care product to provide clean hair. These compositions may also include additional ingredients such as a dermatologically acceptable carrier.

"Cosmetics," as used herein, include without limitation, lipstick, mascara, rouge, foundation, blush, eyeliner, lipliner, lip gloss, facial or body powder, sunscreens and blocks, nail polish, mousse, sprays, styling gels, nail conditioner, whether in the form of creams, lotions, gels, ointments, emulsions, colloids, solutions, suspensions, compacts, solids, pencils, spray-on formulations, brush-on formulations and the like. "Personal care products" include, without limitation, bath and shower gels, shampoos, conditioners, cream rinses, hair dyes and coloring products, leave-on conditioners, sunscreens and sunblocks, lip balms, skin conditioners, cold creams, moisturizers, hair sprays, soaps, body scrubs, exfoliants, astringents, depilatories and permanent waving solutions, antidandruff formulations, antisweat and antiperspirant compositions, shaving, preshaving and after shaving products, moisturizers, deodorants, cold creams, cleansers, skin gels, rinses, whether in solid, powder, liquid, cream, gel, ointment, lotion, emulsions, colloids, solutions, suspensions, or other form. "Pharmaceutical preparations" in accordance with the present invention include, without limitation, carriers for dermatological purposes, including topical and transdermal application of pharmaceutically active ingredients. These can be in the form of gels, patches, creams, nose sprays, ointments, lotions, emulsions, colloids, solutions, suspensions, powders and the like. Compositions in accordance with the invention include cosmetics, personal care products and pharmaceutical preparations.

The invention also features treating cancers that include various malignant and benign tumors such as malignant melanoma, malignant lymphoma, digestive cancers, lung cancer, esophageal cancer, stomach cancer, colon cancer, rectal cancer, small bowel cancer, ureteral tumor, gallbladder cancer, bile duct cancer, biliary tract cancer, breast cancer, liver cancer, pancreas cancer, testicular tumor, maxillary cancer, lingual cancer, lip cancer, mouth cancer, pharyngeal cancer, ovarian cancer, uterine cancer, prostate cancer, thyroid gland cancer, brain tumor, Kaposi's sarcoma, hemangioma, leukemia, polycythemia vera, neuroblastoma, retinoblastoma, myeloma, bladder tumor, sarcoma, osteosarcoma, myosarcoma, skin cancer (e.g., melanoma), renal cancer, urinary cancer, childhood cancers, glioma and the like.

Individuals with cancer can be identified using methods known in the art, e.g., because they display symptoms or as a result of screening. Additional clinical tests can be performed and include, but are not limited to, blood tests, X-rays, CT scans, endoscopy, and histological examination of biopsy tissue, to confirm the diagnosis. Symptoms of cancer in an individual include, but are not limited to, unusual lumps or swelling, hemorrhage, pain and/or ulceration, enlarged lymph nodes, cough and hemoptysis, hepatomegaly (enlarged liver), bone pain, fracture of affected bones and neurological symptoms, weight loss, poor appetite and cachexia (muscle wasting), excessive sweating, and anemia.

Screens for identifying individuals with cancer are known in the art. Screening methods include, but are not limited to, self-examination, mammograms, fetal occult blood testing, cervical cytology, digital rectal exam, prostate specific antigen (PSA) blood testing, sigmoidoscopy, which looks for visual abnormality in the rectum and lower part of the colon, and colonoscopy, which allows visualization of the rectum and entire colon, and double contrast barium enema (DCBE), which allows radiographic examination of the rectum and colon.

The present methods are particularly effective for tumor-suppression of growth factor-related cancers, for example, hyperproliferative cancers, and any of the present methods (whether directed toward the treatment of cancer, wounds, or less serious skin conditions such as wrinkles) can include the step of identifying a subject in need of treatment. Signaling pathways that mediate normal function of growth factors are often dysregulated in various cancers, which can lead to, for example, malignancy. Growth factors that promote angiogenesis can also contribute to tumor growth and/or progression.

The featured methods can be carried out by, for example, administering to the patient a therapeutically effective amount of a pharmaceutical composition comprising a fragment of fibronectin, vitronectin, or a growth factor, or a biologically active variant thereof, as described herein. As noted, the methods can optionally include a step of identifying a patient in need of treatment, and that patient can have a cancer associated with overexpression of a growth factor (e.g., overexpression of IGF-1, TGFβ1, TGFβ2, PDGF-BB, bFGF, FGF-7, VEGF-A or NGF. In addition to administration of a compositions described herein, the patient can receive a second type of treatment for cancer. That is, the present compositions can be used in conjunction with existing chemotherapies, radiation therapy, surgery, or any other cancer treatment.

The invention features methods for promoting tissue regeneration, including, for example, wound healing. As used herein, tissue regeneration is used to refer to the replacement of damaged tissue by the proliferation and differentiation of cells into a tissue. Tissue damage can occur by any means, including physical injury, disease, and infection. As described herein, "wound-healing" is used as a non-limiting example of tissue regeneration.

The primary goal in the treatment of wounds is to achieve wound closure. Open cutaneous wounds represent one major category of wounds and include burn wounds, neuropathic ulcers, pressure sores, venous stasis ulcers, and diabetic ulcers. Open cutaneous wounds routinely heal by a process which comprises six major components: i) inflammation, ii) fibroblast proliferation, iii) blood vessel proliferation, iv) connective tissue synthesis v) epithelialization, and vi) wound contraction. Wound healing is impaired when these components, either individually or as a whole, do not function properly. Numerous factors can affect wound healing, including malnutrition, infection, pharmacological agents (e.g., actinomycin and steroids), diabetes, and advanced age (see Hunt and Goodson in *Current Surgical Diagnosis & Treatment* (Way; Appleton & Lange), pp. 86-98, 1988).

The term "wound" refers broadly to injuries to the skin and subcutaneous tissue initiated in different ways (e.g., pressure sores from extended bed rest and wounds induced by trauma) and with varying characteristics as well as to injuries of other tissues and bone, including tissues and bone in or around the vicinity of a primary wound site. Of course, wounds can also be made surgically or by disease (e.g. cancer). Wounds may be classified into one of four grades depending on the depth of the wound: i) Grade I: wounds limited to the epithelium; ii) Grade II: wounds extending into the dermis; iii) Grade III: wounds extending into the subcutaneous tissue; and iv) Grade IV (or full-thickness wounds): wounds wherein bones are exposed (e.g., a bony pressure point such as the greater trochanter or the sacrum). The term "partial thickness wound" refers to wounds that encompass Grades I-III; examples of partial thickness wounds include burn wounds, pressure sores, venous stasis ulcers, and diabetic ulcers. The term "deep wound" is meant to include both Grade III and Grade IV wounds. The present invention contemplates treating all wound types, including deep wounds and chronic wounds.

The phrases "promote wound healing," "enhance wound healing," and the like refer to either the induction of the formation of granulation tissue of wound contraction and/or the induction of epithelialization (i.e., the generation of new cells in the epithelium). Wound healing is conveniently measured by decreasing wound area. It is not intended that phrases such as "promote wound healing" or "enhance wound healing" require a quantitative comparison with controls. In the case of treatment of a chronic wound, it is sufficient that evidence of wound healing begin after treatment. Many traumatic wounds and cancer extirpations must be left open to heal by secondary intention, and patients having such wounds and extirpations can be treated with the compositions described herein that promote wound healing.

The incidence of chronic wounds, sometimes referred to as non-healing wounds, is rising due to events such as aging populations; an increase in age-related diseases in those populations; an increase in the incidence of AIDS; and an increase in radiation wounds secondary to cancer intervention. Patients who have chronic wounds, including those associated with the events just described, can be treated with the compositions described herein that promote wound healing.

The present compositions can be used either instead of or to supplement existing wound-care procedures such as skin grafting and tissue flaps, debridement, and the administration of anti-inflammatory, antibacterial and/or anti-pain medications. Patients amenable to treatment include those who have chronic dermal ulcerations, as can occur in association with diabetes. Diabetic ulcers, however, are just one part of the chronic wound picture. It is estimated that 5.5 million people in the United States have chronic, nonhealing wounds.

The methods of the invention include a step of administering to a patient a therapeutically effective amount of a pharmaceutical composition comprising a peptide fragment, e.g., of fibronectin and/or vitronectin, or a biologically active variant thereof, as described herein. The peptide fragment, e.g., of fibronectin and/or vitronectin, or the biologically active variant thereof, can be present in a complex with one or more growth factors. The methods can optionally include a step of identifying a patient in need of treatment. Such patients include patients who are suffering from a surgical extirpation or incision of the skin, mucosa, underlying connective tissue, fascia, nerve or muscle; patients who are suffering from a traumatic laceration or tissue loss of the skin, mucosa, underlying connective tissue, fascia, nerve, muscle or bone; and patients who are suffering from a burn or ulceration of the skin, mucosa, underlying connective tissue, fascia, nerve or muscle.

Suitable formulations are described herein and, generally, take the form of a solution, ointment or salve. The fragments of fibronectin and/or vitronectin, whether or not complexed with a growth factor, can also be administered by way of their inclusion in a biomaterial, such as a synthetic polymer, an engineered ECM, a bandage, dressing, compress, or the like.

By other methods of the invention, one can localize an endogenous growth factor to a tissue of a patient. These methods can be carried out by administering, to the patient, a therapeutically effective amount of a composition that includes a fragment, e.g., of fibronectin and/or vitronectin, or a biologically active variant thereof, as described herein. As in the more specific treatment methods described herein, these compositions can be administered by way of topical application of a pharmaceutical composition, a biomaterial, or a solid support, or by other local and systemic routes (e.g., orally, intravenously, intramuscularly, subcutaneously, intradermally, pericutaneously, or transmucosally). These methods can be described as methods of delivering one or more growth factors to a patient. The methods can optionally include a step of identifying a patient in need of treatment. Such patients include patients who are suffering from an injury to a tissue, a loss of a tissue or a disorder resulting in tissue disfigurement or dysfunction. More specifically, the patient can be suffering from an injury or loss to the brain, spinal cord or nerves or a disorder resulting in brain, spinal cord or nerve dysfunction; an injury or loss to the heart or blood vessels or a disorder resulting in heart or blood vessel dysfunction; an injury or loss to the lung, nasopharyngeal tract, sinuses, trachea or airways or a disorder resulting in lung, nasopharyngeal tract, sinus, trachea or airway dysfunction; an injury or loss to the gastrointestinal tract, liver or pancreas or a disorder resulting in gastrointestinal tract, liver or pancreas dysfunction; an injury or loss to a kidney, ureters, bladder or urethra or a disorder resulting in kidney, ureters, bladder or urethra dysfunction; an injury or loss to cartilage, synovium, menicus, ligament, tendon or nucleus pulposis or a disorder resulting in cartilage, synovium, menicus, ligament, tendon or nucleus pulposis dysfunction; an injury or loss to bone; an injury or loss to lips, tongue or gums or a disorder resulting in lip, tongue and gum dysfunction; an injury or loss to the subcutaneous tissue or a disorder resulting in subcutaneous tissue dysfunction.

The invention also features methods for promoting the isolation, proliferation, differentiation and/or activity of stem cells. The methods can be carried out with various compositions, including fragments of fibronectin per se as well as complexes containing such fragments bound to growth factors and the tissue-engineered solid-support products described herein. Similarly, one can promote the delivery of stem cells by administering to a patient a therapeutically effective amount of a composition that includes stem cells and a fragment of fibronectin or vitronectin as described herein (in its various forms, including forms in which the fragment of fibronectin or vitronectin is associated with a solid support or contained within a tissue engineered product). More generally, the methods of the invention include methods for promoting the isolation, proliferation, and delivery of cells. As noted, these cells can be stem cells or can be differentiating into, or differentiated into, osteoblasts, epithelial cells, fibroblasts, myocytes, adipocytes, neural cells, endothelial cells, chondrocytes, hematopoietic cells or lymphocytes. The cells can be genetically engineered or simply isolated from a patient or a cell or tissue culture.

Methods of Screening:

The fibronectin and vitronectin fragments described herein were identified, in part, by using the FN-null cell viability assay described herein. This method was developed based on the observation that mouse fibroblasts null for FN ("FN-null" cells) plated on $FNIII_{8-11}$ failed to survive even in the presence of PDGF-BB while cells plated on intact FN or fibronectin functional domains (FNfds) containing both $FNIII_{8-11}$ plus a GF-binding domain (e.g., $FNIII_{1-11}$ and $FNIII_{8-V15}$) survived in the absence of PDGF-BB and proliferated in its presence. This assay can be used to identify the minimal fibronectin and vitronectin fragments, in addition to $FNIII_{8-11}$ (or another functionally equivalent peptide) required for FN-null cell survival (in the absence of a growth factor, e.g., PDGF-BB) and FN-null cell proliferation (in the presence of a growth factor, e.g., PDGF-BB). Minimal fibronectin and vitronectin fragments identified by this method have been shown to bind and/or enhance growth factors and for this reason are termed growth factor binding peptides (GFBPs) or growth factor enhancing peptides (GFEPs) herein.

In some embodiments, the invention features a method of screening test compounds to identify compounds that promote the survival or proliferation of FN-null cells when plated on $FNIII_{8-11}$ in the presence or absence of a growth factor, e.g. PDGF-BB. These test compounds can be, but are not limited to, growth factor binding and/or enhancing peptides (GFBPs) derived from fibronectin or vitronectin.

In some embodiments, the invention features a method of screening test compounds to identify test compounds that increase or decrease the survival or proliferation of FN-null cells when plated on $FNIII_{8-11}$ in the presence of a compound known to allow the survival or proliferation of FN-null cells, e.g., a FN-derived peptide, or, e.g., a VN-derived peptide. This method of screening may be performed in the presence or absence of a growth factor, e.g., PDGF-BB.

Test compounds that can be screened by methods of this invention include, but are not limited to, fragments of fibronectin, fragments of vitronectin, and fragments of growth factors as described previously. Also included are homologs of fragments, modified fragments, and peptide mimetics as described previously. Peptide variants generated by methods known in the art using mutational techniques can also be used as test compounds. For example, peptide variants can be generated by methods of in vitro protein evolution known in the art and employing phage display as described in Thom et al. (*Proc. Natl. Acad. Sci. USA* 103(20):6719-7624, 2006), herein incorporated by reference. Further, libraries of test compounds, as described herein, can be screened by the methods of this invention.

Optionally, test compounds to be screened by methods of this invention can be conjugated to Cys-tagged $FNIII_{8-11}$ or to other Cys-tagged cell attachment peptides or proteins using a chemical linker. For example, a Cys-tagged GF binding peptide derived from fibronectin can be crosslinked to Cys-tagged $FNIII_{8-11}$ using poly(ethylene)glycol divinyl sulfone (PEGDVS). Since FN-null cells require growth factor presentation in context of $FNIII_{8-11}$ and a FN GFBP for their survival and growth, this assay can be used to determine the peptide sequence requirements, or other peptide parameters, required for growth factor binding and activity. Alternatively, since Formula IV peptides can substitute for both growth factors and FN GFBP, this assay can screen for growth factors that do not require the presence of FN GFBP for their activity.

Exemplary uses for the screening methods described herein include: the identification of sequence domains within a fibronectin or vitronectin fragment necessary for the survival or proliferation of FN-null cells in the presence of $FNIII_{8-11}$ or other cell attachment moiety; the identification of growth factor fragments capable of inhibiting the survival or proliferation of FN-null cells in the presence of $FNIII_{8-11}$ or other cell attachment moieties; the identification of sequence domains within growth factor fragments sufficient to inhibit the survival or proliferation of FN-null cells in the presence of $FNIII_{8-11}$ or other cell attachment moiety; the identification of other test compounds necessary for the survival or proliferation of FN-null cells in the presence of $FNIII_{8-11}$ or other cell attachment moiety; and the identification of test compounds that are capable of inhibiting the survival or proliferation of FN-null cells in the presence of $FNIII_{8-11}$ or other cell attachment moiety. These methods are of use, for example, in identifying candidate compounds for the treatment of wounds or cancer or for use in cosmetic therapies.

Libraries of Test Compounds:

As used herein, a "test compound" can be any chemical compound, for example, a macromolecule (e.g., a polypeptide, a protein complex, glycoprotein, or a nucleic acid) or a small molecule (e.g., an amino acid, a nucleotide, an organic or inorganic compound). A test compound can have a formula weight of less than about 10,000 grams per mole, less than 5,000 grams per mole, less than 1,000 grams per mole, or less than about 500 grams per mole. The test compound can be naturally occurring (e.g., an herb or a natural product), synthetic, or can include both natural and synthetic components. Examples of test compounds include peptides, peptidomimetics (e.g., peptoids), amino acids, amino acid analogs, polynucleotides, polynucleotide analogs, nucleotides, nucleotide analogs, and organic or inorganic compounds, e.g., heteroorganic or organometallic compounds.

Test compounds can be screened individually or in parallel. An example of parallel screening is a high throughput drug screen of large libraries of chemicals. Such libraries of candidate compounds can be generated or purchased, e.g., from Chembridge Corp. (San Diego, Calif.). Libraries can be designed to cover a diverse range of compounds. For example, a library can include 500, 1000, 10,000, 50,000, or 100,000 or more unique compounds.

The synthesis of combinatorial libraries has been reviewed (see, e.g., Gordon et al., *J. Med. Chem.*, 37:1385, 1994; DeWitt and Czarnik, *Acc. Chem. Res.* 29:114, 1996; Armstrong et al., *Acc. Chem. Res.*, 29:123-131, 1996; Ellman, *Acc. Chem. Res.*, 29:132, 1996; Gordon et al., *Acc. Chem. Res.*, 29:144, 1996; Lowe, *Chem. Soc. Rev.*, 309: 1995, Blondelle et al., *Trends Anal. Chem.*, 14:83, 1995; Chen et al., *J. Am. Chem. Soc.*, 116:2661, 1994; U.S. Pat. Nos. 5,359,115, 5,362,899, and 5,288,514; and PCT Publication Nos. WO92/10092, WO93/09668, WO91/07087, WO93/20242, and WO94/08051).

Libraries of compounds can be prepared according to a variety of methods, some of which are known in the art. For example, a split-pool strategy can be implemented in the following way: beads of a functionalized polymeric support are placed in a plurality of reaction vessels; a variety of polymeric supports suitable for solid-phase peptide synthesis are known, and some are commercially available (for examples, see, e.g., Bodansky, *Principles of Peptide Synthesis*, 2nd edition, Springer-Verlag, Berlin (1993)). To each aliquot of beads is added a solution of a different activated amino acid, and the reactions are allowed to proceed to yield a plurality of immobilized amino acids, one in each reaction vessel. The aliquots of derivatized beads are then washed, pooled (i.e., recombined), and the pool of beads is again divided, with each aliquot being placed in a separate reaction vessel. Another activated amino acid is then added to each aliquot of beads. The cycle of synthesis is repeated until a desired peptide length is obtained. The amino acid residues added at each synthesis cycle can be randomly selected; alternatively, amino acids can be selected to provide a biased library, e.g., a library in which certain portions of the inhibitor are selected non-randomly, e.g., to provide an inhibitor having known structural similarity or homology to a known peptide capable of interacting with an antibody, e.g., the an anti-idiotypic antibody antigen binding site. It will be appreciated that a wide variety of peptidic, peptidomimetic, or non-peptidic compounds can be readily generated in this way.

The split-pool strategy can result in a library of peptides, e.g., modulators, which can be used to prepare a library of test compounds for use in the screens described herein. In another illustrative synthesis, a diversomer library is created by the method of DeWitt et al. (*Proc. Natl. Acad. Sci. USA*, 90:6909, 1993). Other synthesis methods, including the "tea-bag" technique, described in Houghten et al. (*Nature*, 354:84, 1991), can also be used to synthesize libraries of compounds according to the subject invention.

Libraries of compounds can be screened to determine whether any members of the library show the activity of promoting or inhibiting cell survival or proliferation, and, if so, to identify the inhibitor or activator. Methods of screening combinatorial libraries have been described. See, e.g., Gordon et al., *J. Med. Chem.*, supra. Soluble compound libraries can be screened to isolate candidate compounds, followed by identification of the isolated ligands by conventional techniques (e.g., mass spectrometry, NMR, and the like). Screens are described herein.

Medicinal Chemistry:

Once a compound (or agent) of interest has been identified, standard principles of medicinal chemistry can be used to produce derivatives of the compound. Derivatives can be screened for improved pharmacological properties, for example, efficacy, pharmaco-kinetics, stability, solubility, and clearance. The moieties responsible for a compound's activity in the assays described above can be delineated by examination of structure-activity relationships (SAR) as is commonly practiced in the art. A person of ordinary skill in pharmaceutical chemistry could modify moieties on a candidate compound or agent and measure the effects of the modification on the efficacy of the compound or agent to thereby produce derivatives with increased potency. For an example, see Nagarajan et al. (*J. Antibiot.* 41:1430-8, 1988). Furthermore, if the biochemical target of the compound (or agent) is known or determined, the structure of the target and the compound can inform the design and optimization of derivatives. Molecular modeling software is commercially available (e.g., Molecular Simulations, Inc.) for this purpose.

Test compounds that exhibit one or more of activities (i) modulating FN-null cell survival using assays described herein, (ii) disrupting binding between fibronectin and a growth factor, or fragments thereof, (iii) disrupting binding between vitronectin and a growth factor, or fragments thereof are referred to herein as "candidate compounds." Screening assays can optionally include further testing candidate compounds for their ability to modulate cell migration, effect wound healing in an animal model, and effect cancer cell viability. Screening assays of the present invention may be carried out in whole cell preparations or ex vivo cell-free systems.

Binding Assays:

Binding of a test compound to cell-free sample that includes a full-length polypeptide of interest (e.g., fibronectin, e.g., vitronectin, or e.g., growth factor fragments) of a fragment thereof can be detected in vitro, for example, by reversibly or irreversibly immobilizing the full-length polypeptide on a substrate, e.g., the surface of a well of a plate (e.g., 96-well polystyrene microtitre plate). For example, microtitre plates can be coated with the full-length polypeptide of interest (e.g., fibronectin, e.g., vitronectin, or e.g., a growth factor), or a fragment thereof, washed and blocked (e.g., with BSA) to prevent non-specific binding of test compounds to the plates. Test compounds are added to the coated plate under a number of conditions (e.g., at 37° C. for 0.5-12 hours). The plate can then be rinsed and binding of the test compound to the polypeptide of interest can be detected by any of a variety of art-known methods. For example, an antibody that specifically binds to the polypeptide of interest (e.g., anti-fibronectin, anti-vitronectin, or anti-growth factor) can be used in an immunoassay. If desired, the antibody can be labeled and detected directly (see, e.g., West and McMahon, *J. Cell Biol.* 74:264, 1977). Alternatively, a second antibody (e.g., a labeled antibody that binds to anti-fibronectin, anti-vitronectin, or anti-growth factor as appropriate) can be used for detection. Test compounds that bind to the polypeptide of interest can be detected by their ability to inhibit binding of antibody to immobilized polypeptide of interest. In an alternative detection method, the test compound is labeled (e.g., with a radioisotope, fluorophore, chromophore, or the like), and the binding of a test compound to the polypeptide of interest is detected by detecting label that is immobilized on the substrate.

In still another embodiment, test compounds are immobilized on a substrate, e.g., to a microtitre plate as described above, incubated with a cell free sample that includes the full-length polypeptide of interest (or a fragment thereof), washed, and the ability of the polypeptide of interest to bind to an immobilized test compound is detected. For example, the full-length polypeptide of interest (or a fragment thereof) can be produced as a fusion protein with a protein that can be detected optically, e.g., green fluorescent protein or a variant thereof (which can be detected under UV light), and the ability of the fusion protein to bind the test compound is detected. Alternatively, the polypeptide of interest can be produced as a fusion protein with an enzyme having a detectable enzymatic activity, such as horseradish peroxidase, alkaline phosphatase, β-galactosidase, or glucose oxidase. Genes encoding all of these enzymes have been cloned and are available for use by skilled practitioners. If desired, the fusion protein can include an antigen, which can be detected and measured with a polyclonal or monoclonal antibody using conventional methods. Suitable antigens include enzymes (e.g., horse radish peroxidase, alkaline phosphatase, and β-galactosidase) and non-enzymatic polypeptides (e.g., serum proteins, such as BSA and globulins, and milk proteins, such as caseins). In these methods, the ability of the polypeptide of interest fusion protein to bind to a test compound is detected.

To identify polypeptides that bind to the full-length polypeptide, or fragment thereof (e.g., fibronectin, vitronectin, or a growth factor fragments), a two-hybrid assays of protein/protein interactions can be used (see, e.g., Chien et al., *Proc. Natl. Acad. Sci. USA*, 88:9578, 1991; Fields et al., U.S. Pat. No. 5,283,173; Fields and Song, *Nature*, 340:245, 1989; Le Douarin et al., *Nucleic Acids Research*, 23:876, 1995; Vidal et al., *Proc. Natl. Acad. Sci. USA*, 93:10315-10320, 1996); and White, *Proc. Natl. Acad. Sci. USA*, 93:10001-10003, 1996). Kits for practicing various two-hybrid methods are commercially available (e.g., from Clontech; Palo Alto, Calif.). Further, phage display methods can be used to identify polypeptides that bind to the full-length polypeptide, or fragment thereof (e.g., FN, VN, or GF fragments). Methods are known in the art and kits for practicing phage display selection and screening methods are commercially available (e.g., from New England Biolabs; Ipswich, Mass.).

In certain other embodiments, the interaction of a full-length polypeptide of interest (e.g., fibronectin, vitronectin, or a growth factor), or fragment thereof, and test compound is detected by fluorescence resonance energy transfer (FRET) between a donor fluorophore covalently linked to either the polypeptide of interest or the test compound and an acceptor fluorophore covalently linked to either the polypeptide of interest or the test compound, wherein the acceptor and donor fluorophore are not both linked to the polypeptide of interest or the test compound, and there is suitable overlap of the donor emission spectrum and the acceptor excitation spectrum to give efficient nonradiative energy transfer when the fluorophores are brought into close proximity through the polypeptide of interest-test compound interaction.

In certain other embodiments, the interaction of a full-length polypeptide of interest (e.g., fibronectin, vitronectin, or a growth factor), or fragment thereof, and test compound is detected by surface plasmon resonance.

The binding assays described herein may be used to identify candidate compounds that disrupt physical interaction between a fibronectin, or fragment thereof, and a ligand. Additionally, the binding assays described herein may be used to identify candidate compounds that disrupt physical interaction between a vitronectin, or fragment thereof, and a ligand. Examples of ligands include, but are not limited to growth factors (e.g., TGF-β1, TGF-β2, bFGF, FGF-7, PDGF-BB, VEGF-A, or NGF), or fragments thereof.

In Vitro and In Vivo Model Systems:

Test compounds may be further characterized in in vitro and in vivo model systems. For example, test compounds can be tested for effects on cell migration using Adult Human Dermal Fibroblasts (ADHF), human microvascular endothelial cells (HEDMC), or other cell types. For example, test compounds can be tested for effects on wound healing using the porcine re-injury model. In vitro and in vivo models systems for studying cancer are known in the art (e.g., tumor cell culture and xenotransplantation of tumor cells).

EXAMPLES

Fibronectin Growth Factor-Binding Domains

Data from our laboratory has demonstrated the binding of TGF-β1, PDGF-BB, VEGF-A, and FGF-2 with fibronectin (FN) and its functional domains as well as biological implications of these interactions. Briefly, radiolabeled GFs bound intact FN with the following KDs as judged by non linear regression: TGF-β1, KD=$5.3 \times 10^{-8}$ M; PDGF-BB, KD=$4.9 \times 10^{-8}$ M, FGF-2, KD=$4.4 \times 10^{-8}$ M. As determined by plasmon resonance modulation, all GFs, except EGF, bound to the composite heparinII-binding and variably-spliced IIICS domains (FNIII$_{12-V15}$) (FIG. 1) with the following order of affinities: VEGF (KD=$6.0 \times 10^{-10}$ M)>TGF-β1 (KD=$2.5 \times 10^{-9}$ M)>PDGF-BB (KD=$1.7 \times 10^{-8}$ M)>FGF-2 (KD=$3.7 \times 10^{-8}$ M). Similar rank orders of affinities were observed with GF binding to the heparinII-binding domain (FNIII$_{12-15}$ and FNIII$_{12-14}$): PDGF-BB (KD=$6.8 \times 10^{-9}$ M)≥TGF-β1 (KD=$1.6 \times 10^{-8}$ M)>FGF-2 (KD=$1.7 \times 10^{-7}$ M); TGF-β1 (KD=$7.6 \times 10^{-9}$ M)>PDGF-BB (KD=$5.5 \times 10^{-8}$ M), respectively. VEGF, TGF-β1, PDGF-BB and FGF-2 bound IIICS with similar affinities (KD~$10^{-7}$ M). EGF again failed to bind this functional domain and all others tested. None of the GFs detectably bound the amino-terminal end of FN (FN$_{70}$) nor the classic cell-binding domain containing RGD (FNIII$_{8-11}$). Although TGF-β1 and PDGF-BB bound the FNIII$_{1-11}$, VEGF and FGF-2 did not. Nevertheless, all four GFs bound FNIII$_{1-7}$, FNIII$_{1-2}$, FNIII$_1$ and FNIII$_2$, and all but VEGF bound anastellin, a 76-aa peptide within FNIII$_1$. These data strongly suggest a cryptic GF-binding site within the first and second type III repeat of FN. The tested biological activities of GFs bound to a FN functional domain were retained or enhanced. Our studied suggest that FN, or its fragments, may act as promiscuous cofactors for GFs and provide a novel mechanism by which GFs and ECM may accentuate the cooperativity of GF receptors and integrins on the cell surface. In addition, our studies provide important information regarding the delivery of GFs and the sequestering of GFs, as appropriate, for therapeutic (e.g., surgical) or aesthetic indications, including wound healing treatments (where an aim is GF delivery) and cancer treatments (where an aim is GF sequestration). Where FN fragments are used to deliver GFs, they may be described as maintaining, activating, stabilizing or enhancing GF activity.

Synthetic Peptides that Bind TGF-β1 and PDGF-BB

We have elucidated four homologous 25 amino acid sequences within FN. Two are within FNIII$_1$ (peptide 1 and peptide 2), one within FNIII$_{13}$ (peptide 3), and one within the FN variably-spliced IIICS (peptide 4). Their sequences are:

```
                         (peptide 1; SEQ ID NO: 17)
QPSHISKYILRWRPKNSVGRWKEAT;

(peptide 2; SEQ ID NO: 18)
QLISIQQYGHQEVTRFDFTTTSTST;

(peptide 3; SEQ ID NO: 19)
NGQTPIQRTIKPDVRSYTITGLQPGT;
and (peptide 4; SEQ ID NO: 20)
QPSVGQQMIFEEHGFRRTTPPTTAT.
```

These peptides represent domains that follow the sequence pattern [QN]-X(1,2)-[ST]-X(0,1)-[IG]-[QS]-[KRQ]-[YTM]-[IG]-X(4,5)-X(0,1)-[KR]-X(1,2)-X(1,2)-[RT]-X(1,2)[KQTS]-X(2)-T (SEQ ID NO:30) and that bind TGF-β1 with a certain affinity. Our equilibrium binding experiments indicate binding affinities of $1.3 \times 10^{-7}$ M, $2.7 \times 10^{-7}$ M, $1.4 \times 10^{-7}$ M and $1 \times 10^{-7}$ M, respectively. We know of no other peptides in the human genome database that follow this pattern. Peptide 1 also binds PDGF-BB (KD=$2.5 \times 10^{-7}$ M) while a scrambled control does not. Further analysis of peptide 1 demonstrated that QPSHISKYILRWRPK (peptide 1A; SEQ ID NO:21) and ILRWRPKNSVGRWK (peptide IB; SEQ ID NO:22) bound TGF-β1 with affinities of $4.4 \times 10^{-7}$ M and $4.0 \times 10^{-7}$ M, respectively, while QPSHISKY (SEQ ID NO:23) had minimal binding activity.

Among our objectives was the production of an acellular 3-dimensional (3-D) extracellular matrix that facilitates tissue repair through its intrinsic ability to recruit cells, such as parenchymal cells, to the site of an injury and to induce them to produce new cells and tissue(s). As noted above, the ECM can include one to three (or all three) fibronectin functional domains (FNfds), including $FNIII_{8-11}$ (C), $FNIII_{12-15}$ (H) and $FNIII_{12-v15}$ (HV), which can be constructed recombinantly as arrayed on a natural FN heterodimer and incorporated into a hydrogel (e.g., tethered to an intramolecularly crosslinked hyaluronan (HA) hydrogel). C, H and HV appear to be necessary and sufficient for optimal adult human fibroblast migration. $FNIII_1$, as well as H and HV, promiscuously, but selectively, bind growth factors, which retain functional activity while bound. This finding led us to believe that engineered ECM can bind GFs, whether exogenously added or endogenously generated, and thereby localize them in an active form to sites where an engineered ECM has been applied. Appropriate sites include freshly debrided ulcers (e.g., chronic ulcers), as well as surgical and traumatic wounds, including those that cannot be closed.

Fibroblast Migration is the Rate Limiting Step in Granulation Tissue Formation

Using two new paradigms of acute wounds, we have previously determined that fibroblast activation and migration, rather than provisional matrix maturation, is the rate limiting step in granulation tissue development (which normally has a 3-day lag after injury). A reinjured porcine cutaneous wound model was developed to establish whether fibrin matrix maturation was the limiting step. Full-thickness wounds were allowed to heal for 5 or 7 days and then reinjured with aggressive curretting to remove all granulation tissue. A new fibrin clot formed in the re-injured wounds, which was replaced by a fibroblast-rich granulation tissue within just 24 to 48 hours. Little (~24 h) or no delay was observed in the initiation of fibroblast migration into the 5 or 7 day re-injured wounds, respectively. It is unlikely that fibrin matrix maturation was responsible for the 3-day lag in granulation tissue formation consistently observed in fresh wounds. The second paradigm was freshly made porcine skin wounds. Using this animal model, we found that addition of culture-activated skin fibroblasts plus platelet releasate or platelet-derived growth factor-BB (PDGF-BB), suspended in a human fibrin/FN gel could induce precocious granulation tissue at 3 days (i.e., the lag phase was shortened to two days). Furthermore, when fibroblasts are in an appropriate ECM context (including routine tissue culture as the cells become enmeshed in FN as they approach confluence), increases in α5β1 expression on cell surface takes approximately 24 hours after PDGF stimulation.

FN is Important for Human Fibroblast Transmigration from 3-D Collagen to Fibrin Gel In Vitro and In Vivo Based on our prior in vitro data, FN is critical for cell invasion of the fibrin clot. To simulate fibroblast movement from periwound collagenous stroma into provisional matrix-filled wound space, a contracted collagen gel containing skin fibroblasts was pasted onto a surface of fibrin fibrils and surrounded by a fibrin clot. This forms an "inside-out" wound environment. To further simulate the in vivo situation, 30 ng/ml PDGF was added to the fibrin clot. Fibroblast appearance in the translucent fibrin gel was quantified by cell counts.

At 24 hours cell accumulation in the fibrin gel was attributable to migration rather than mitogenesis as judged by the similar accumulation of nonproliferating, irradiated cells. Transmigration from the organotypic dermal environment into fibrin required FN in both matrices. In addition, migration was dependent on α5β1 and αvβ3, integrin receptors that bind FN. Absence of FN in the provisional matrix of chronic ulcers may also hinder tissue cell accumulation in the wound. This possibility has been supported in fresh porcine wounds to which exogenous fibrin without FN was added. Relative few cells moved into these wounds compared to wounds receiving fibrin replete with FN. Thus, one of the fundamental reasons that a fresh surgical or traumatic gaping wound heals faster than a chronic ulcer may be that the former has a provisional matrix with abundant FN while the latter has little or no FN.

FN Functional Domains are Required for Improved Adult Human Dermal Fibroblast (ADHF) Migration The HA-FN provisional matrix of early granulation tissue appears to have the capacity to support robust fibroblast migration. This trait is desirable for an ECM present at a time when new tissue formation depends on robust cell movement. Since FN is required for fibroblast migration through both fibrin clots and HA gels, the fibronectin functional domains (FNfds) required for migration were sought. From the subsequent investigations we determined that functional domains containing the cell-binding site (FNIII8-11)(C) for α5β1 and αvβ3, the heparin II binding site (FNIII12-15)(H) for CD44 and Syndecan 4, and the IIICS (V) sites for α4β1 were required for optimal AHDF migration. Interestingly, neonatal human fibroblast cell strains and cell lines, such as 3T3 cells or rat fibrosarcoma cells, only required the cell-binding domain ($FNIII_{8-11}$) for optimal movement, and AHDF only required $FNIII_{8-11}$ for optimal adhesion and spreading. It is known that cell movement depends on the amount of ligand and the amount of receptor available. Using human recombinant FNfds, we have demonstrated the requirement of all three domains at surface coating concentrations of 0.33 to 100 µM for optimal PDGF-stimulated AHDF migration.

Cloning and Expression of Human FN Domains

Figure 2:
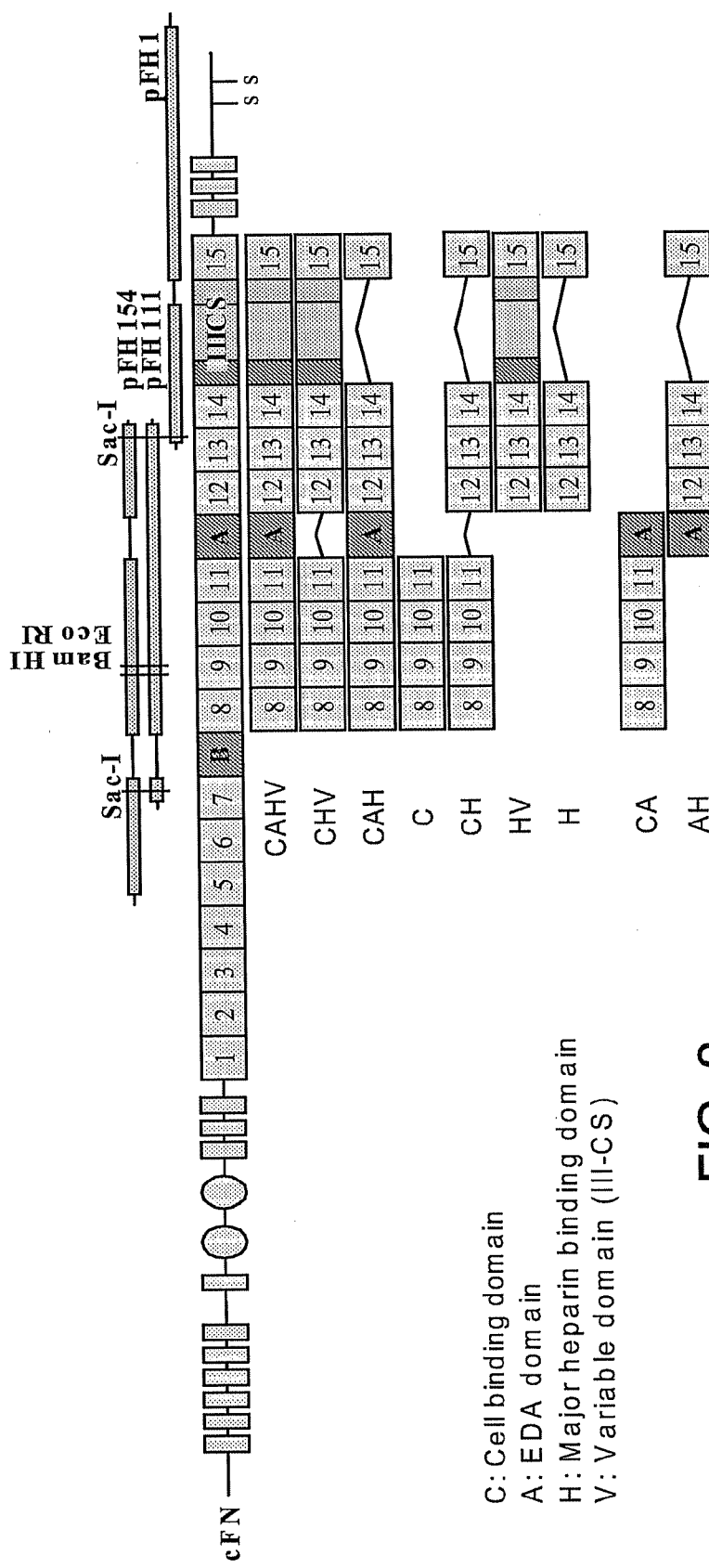
FIG. 2 is a diagram of cellular fibronectin (cFn). Various domains are illustrated.

Functional human FN domains have been cloned by PCR using the human cDNA clones pFH1, pFH111 and pFH154, as templates or by subcloning of the restriction enzyme fragments from these plasmids (FIG. 2). Clones pFH111 and pFH154 were purchased from the American Type Culture Collection (ATCC), while the pFH1 clone was obtained from the Japan Health Sciences Foundation. A bacterial expression vector, pETCH, was constructed by modifying the pET vector from Stratagene. The inserts were cloned at the BamHI and HindIII sites, and confirmed by DNA sequencing to rule out possible synthesis errors during PCR. Protein induction and purification procedures have been optimized for each of the FN fragments. Protein expression was induced in the BL21DE3LysS strain of E coli by the addition of 0.5 mM IPTG to the L-Broth and affinity-purified using the Ni-NTA agarose (Qiagen) according to the manufacturer's protocol. After elution with 250 mM imidazole, the protein solution was purified in a G25 gel filtration column equilibrated in PBS, and the aliquots stored at −70° C. The PCR products were purified and digested with restriction enzymes. The restriction fragments are separated by gel electrophoresis, purified, ligated into the vector, and transformed into competent bacteria DH5α. The clones are confirmed by DNA sequencing, and transformed into BL21DE3-LysS bacteria for protein purification. In addition, we have cloned and expressed $FNIII_{1-11}$, $FNIII_{1-2}$, $FNIII_1$, $FNIII_2$, $FNIII_{3-6}$, and $FNIII_{12-14}$. The recombinant FN functional domains have three extra amino acids (MetGlySer) at the N-terminus and seven to eight extra amino acids (ThrSerHisHisHisHisHisHisCys (SEQ ID NO:71)) at the C-terminus (Thr is naturally present at the end of type III repeat 11 and EDA). In some constructs, the coding sequence of glutathione S-transferase (GST) was inserted at the C-terminus.

Engineered ECM Platforms

Figure 3A:
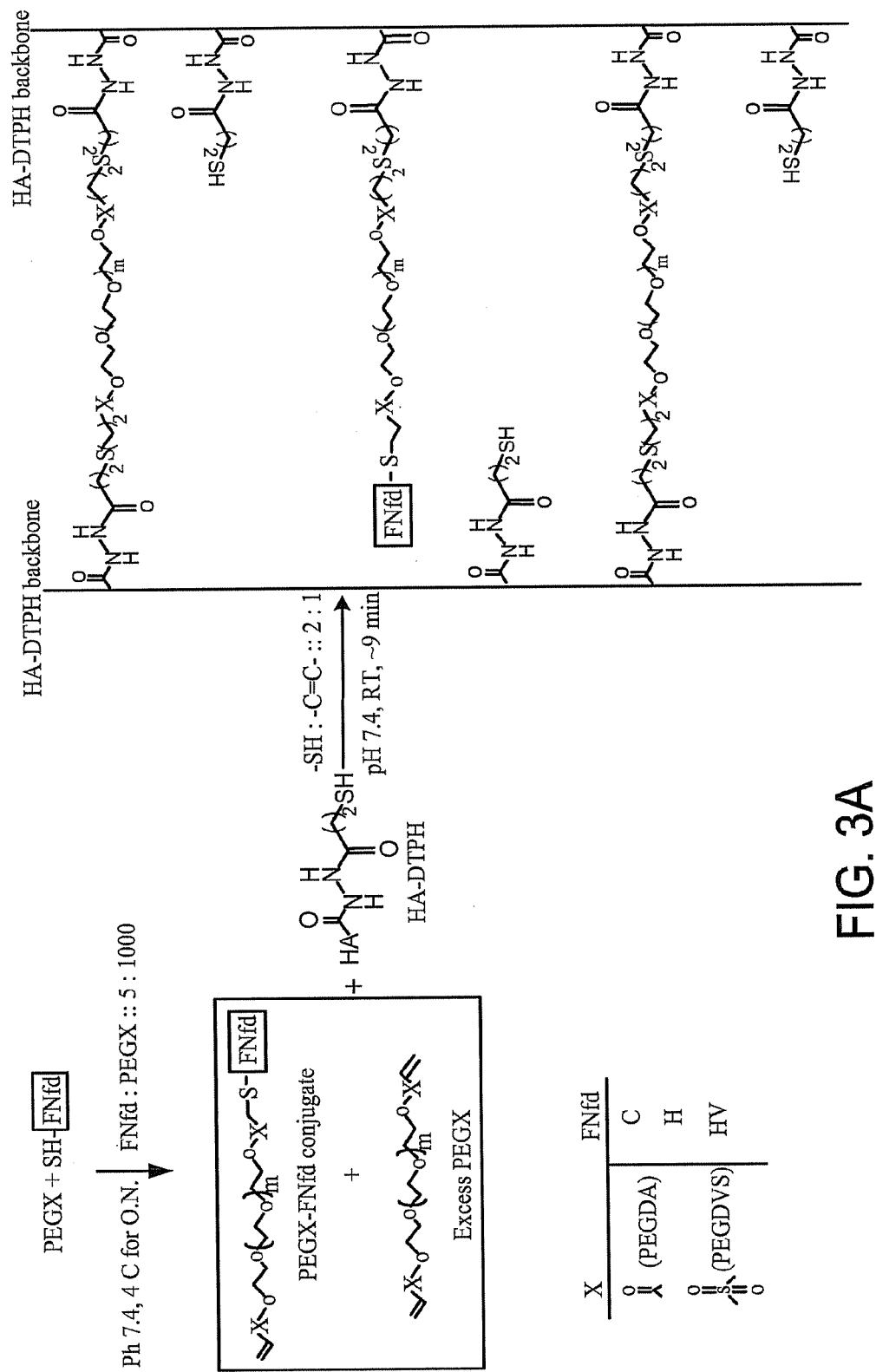
FIG. 3. engECM promotes optimal AHDF migration in vitro and in vivo. a) an illustration of a method for synthesizing an ECM. Cys-tagged FNfds were incubated with homobifunctional PEGX derivatives (X=diacrylate [DA] or divinylsulfone [DVS], Nektar Therapeutics, Huntsville, Ala.) at a 1:10,000 ratio for final bulk densities of 300 nM FNfds in eng ECM. Thiol-funtionalized HA-DTPH was synthesized as previously described. The 1:10,000 mixture of FNfd-PEGX and homobifunctional PEGX was added to HA-DTPH to tether FNfd-PEGX to HADTPH and to intramolecularly crosslink HA-DTPH, respectively. b) AHDF spreading and migration on HA-DTPH-PEGDVS-FNfd hydrogel (engECM) surfaces. For spreading cells were incubated on engECM in DMEM 37° C. for 6 h and for migration cells in agarose droplets were incubated on engECM with PDGF at 30 ng/ml in DMEM at 37° C. for 18 h. Migration is expressed as the area outside agarose covered by migrated cells and determined by Spot software. n=6. c) Image of AHDF migration from agarose droplet on engECM at 18 hrs. d) Trichrome-stained images of bisected porcine wounds at 2 days in a re-injury model (69). 8 mm punch biopsy (full-thickness) wounds created in female Yorkshire pigs were covered with Tegaderm® and allowed to heal spontaneously for 5 days. Thereafter, the granulation tissue was curetted out, creating fresh wounds. Sterile, endotoxin-free HA hydrogels coupled with C, H and HV (engECM), HA hydrogels without FNfds, and HA hydrogels coupled with RGD were added to the wounds as pre-gelling solutions that gelled in situ within 9 min. Left panel is re-injured wound filled with engECM+ 100 ng/ml PDGF-BB. Right panel is reinjured wound filled with HA-DTPH-PEGDVS-RGD+100 ng/ml PDGF-BB. e) Percent wound filled with granulation tissue at day 4 after full-thickness 8 mm punch biopsies on backs of outbred Yorkshire pigs. Wounds were filled with material as noted and covered with Tegaderm until harvested. n=6. *$P<0.001$ between engECM and control.
Figure 3B:
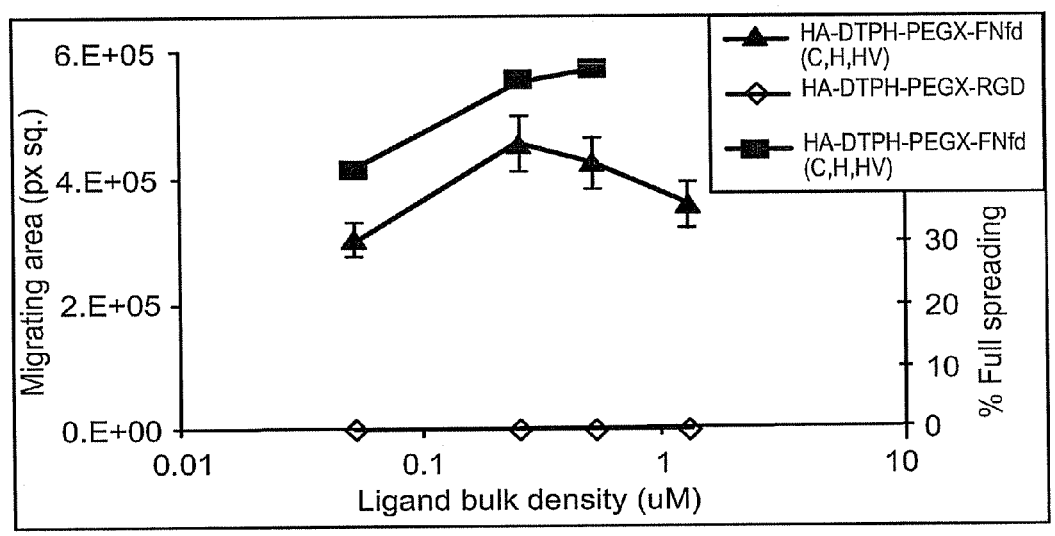
Figure 3C:
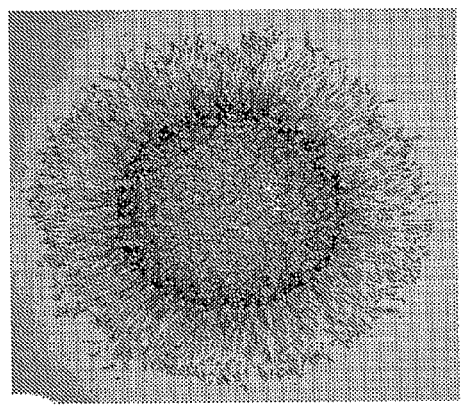

We have engineered an intramolecularly cross-linked HA hydrogel matrix that is tethered with FNfds C, H and HV for improved fibroblast migration in in vitro models and in vivo wound healing (FIG. 3A). The engineered ECM also provides a useful 3-D complex ECM for studies on cell responses to complex ECM containing different FNfds. Rapid (within just 18 hours) and robust migration of adult human dermal fibroblasts (AHDFs) occurred on engineered ECM peaking at a FNfd density of 0.26 μM in a typical bell-shaped manner (FIG. 3B). Migration appeared to occur en masse rather than as single cells (FIG. 3C). AHDF spreading and proliferation also reached 90% of maximal at 0.26 μM. Thus, 0.26 μM appeared optimal for FNfds stimulation of AHDF functional responses.

After obtaining the optimum FNfds bulk densities (268 nM) and crosslinking ratios (2:1) from in vitro functional studies, we tested our engineered ECM in vivo in a porcine re-injury model. The wounds of a porcine re-injury model contain a large population of activated periwound tissue fibroblasts that transform from the (usual) stationary phenotype into a migratory one that facilitates granulation tissue formation. Therefore, this re-injury model is suited mainly to identify any adverse effect(s) of a wound additive, which would compromise this migratory phenotype of the stimulated periwound fibroblasts. Before use in vivo, the FNfd-SH solutions were treated with deToxi gel (Pierce, Ill.) to remove endotoxins. Punch biopsy (8 mm; full-thickness) wounds created in female Yorkshire pigs were covered with Tegaderm® and allowed to heal spontaneously for 5 days. Thereafter, the granulation tissue was curetted out, creating fresh wounds. Sterile, endotoxin-free HA hydrogels coupled with C, H and HV, HA hydrogels without FNfds, and HA hydrogels coupled with RGD were added to the wounds as pre-gelling solutions that gelled in situ within 9 minutes. Five wounds received no HA hydrogels and were treated as controls.

Figure 3D:
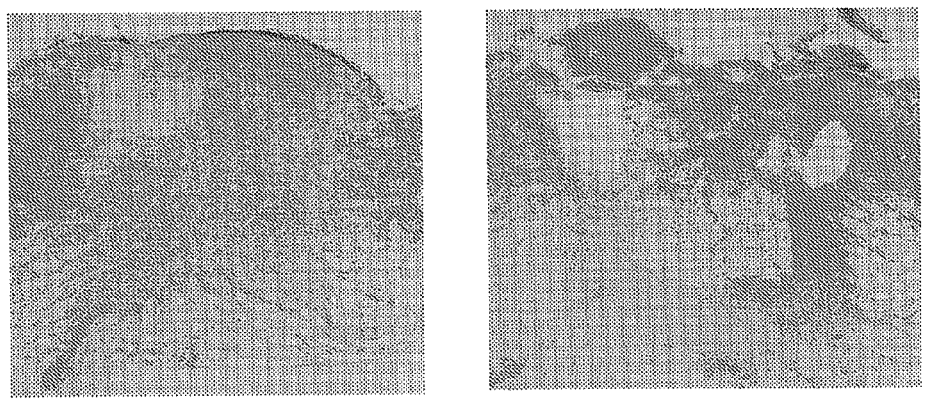

When the specimens were harvested at two days post-implantation and analyzed histologically, we observed essentially no signs of acute inflammation, suggesting the overall biocompatibility of engineered ECM. More remarkably, wounds receiving these acellular engineered ECM hydrogels showed rapid fibroblast migration and profound granulation tissue formation (90% wound space filled) within just two days (FIG. 3D, left panel). In contrast, wounds filled with HA-DTPH-PEGDVS-RGD showed marked inhibition of granulation tissue formation (FIG. 3D, right panel). These results suggest, first, that C, H and HV are instrumental in facilitating the recruitment of host tissue fibroblasts into acellular engineered ECM and, second, once migrated into the wounds, recruited fibroblasts assume normal tissue phenotype by depositing in situ collagen (as detected by trichrome blue staining) which demonstrates inductive properties of FNfds. In addition, the engineered ECM hydrogels also encouraged reepithelialization by stimulating keratinocyte migration.

Figure 3E:
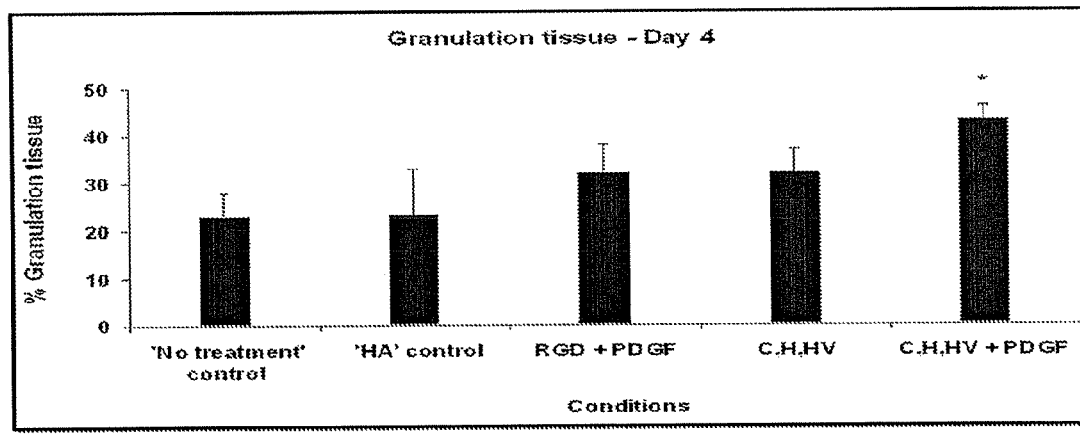

Next, engineered ECM were implanted into "regular" porcine wounds immediately after wounding. Tissue samples were harvested and analyzed at 3, 4, 5 and 7 days. From a power analysis we determined that 6 replicates for each condition were sufficient to obtain statistical differences at 95% confidence if the variance among replicates was <20%. All HA hydrogels were endotoxin-free and implanted in a manner that accounts for the regional differences in tissue ingrowth between the dorsal/ventral or anterior/posterior ends. The harvested wound specimens were stained with trichrome blue for histological analysis to delineate morphological alterations in the granulation tissue. No granulation tissue had accumulated in 3 day wounds regardless of treatment (i.e., no treatment), HA hydrogels at crosslinking ratios of 2:1 without FN functional domains, 268 μM RGD tethered to HA hydrogels, or engineered ECM decorated with C, H, and HV at final bulk densities of 268 nM each. Wounds four days after injury, however, demonstrated statistically significant differences in healing only among wounds containing engineered ECM+PDGF versus wounds receiving no treatment or blank HA hydrogels (P<0.001 by one way ANOVA and Tukey post hoc analysis) (FIG. 3E). The best results occurred in wounds receiving engineered ECM that was decorated with C, H, and HV and preloaded with 100 ng/ml of PDGF-BB. This was particularly intriguing since the final amount of PDGF-BB added to each of these wounds was only ~15 ng (~150 μL of hydrogel per wound containing 100 ng/ml PDGF-BB), which is a 30-3000 fold lower dose than what was previously reported to produce significant accentuation. By 5 and 7 days, wounds were on average filled with granulation tissue at 75% and 100% of total wound, respectively, with no differences noted among experimental conditions.

The extent of re-epithelialization was also determined from the histological sections. Since Masson trichrome stains tissue cells pink, the migrating epidermal tongue was easily detected and traced for quantitative analysis. Similar to granulation tissue, percent re-epithelialization was increased by FNfd-derivatized xHA, in contrast to non-derivatized xHA, with the greatest accentuation produced by xHA-FNfd+PDGF-BB. xHA-FNfd hydrogels alone showed an increase, albeit insignificant, in percent re-epithelialization.

Angiogenesis was also determined from histological evaluation of sections from these experiments. CD31, or PECAM-1, is a characteristic endothelial cell adhesion molecule that is expressed on its surface and plays a role in angiogenesis. Laminin is an ECM protein found in the basal laminae of mature capillaries. When we double-labeled day 4 wound sections with anti-CD31 and anti-laminin, we found that all CD31-positive structures were colocalized with laminin, indicating that the capillaries had matured. The nearly vertical alignment of the new capillaries is typical of wound angiogenesis and is due to endothelial cell migration towards the major source of vascular endothelial growth factor (VEGF), the epidermal cells. Similar to a recently reported technique, the quantitative analysis of angiogenesis was performed by measuring the percent area of wound granulation tissue that was occupied by the new capillaries. All wound additives accentuated angiogenesis above the "no treatment" control, with the xHA-FNfd±PDGF-BB hydrogels showing a 2-fold increase. Unlike the effects seen in granulation tissue accumulation and re-epithelialization, PDGF-BB failed to significantly enhance angiogenesis observed with xHA-FNfd alone. Both xHA-FNfd±PDGF hydrogels showed marked increase in percent neovascularization over xHA-RGD+PDGF hydrogels.

FN Domains Bind PDGF-BB

PDGF is a potent chemoattractant and mitogen for fibroblasts, promotes healing of soft tissue wounds and is approved by the U.S. Food and Drug Administration for treatment of chronic cutaneous ulcers. Interestingly, we observed that as little as 100 ng/ml (15 ng total per wound) PDGF-BB added to 2:1 engineered ECM enhanced granulation formation at 4 days after injury and application of material. This led us to speculate that PDGF was binding to the engineered ECM through the H or HV domain since vascular endothelial GF (VEGF), a member of the PDGF superfamily, had been reported to bind H and remain active while bound. Equilibrium binding studies and surface plasmon resonance were utilized to assay amino- to carboxy-terminal FN domains (FN70, FNIII$_{1-7}$, FNIII$_{8-11}$ (C), and FNIII$_{12-V15}$ (HV) for PDGF binding activity. FNIII$_{1-7}$ and HV were found to have strong binding affinities for PDGF-BB (KD=7.5×10$^{-8}$M, KD=2.1×10$^{-8}$ M, respectively) while the 70 kDa amino terminus of FN (FN70), which includes fibrin and gelatin binding domains and C (FNIII$_{8-11}$) did not. Plasmon surface resonance kinetic binding confirmed these results (KD=1.0×10$^{-7}$ M, KD=1.7×10$^{-8}$M, respectively). Compared to PDGF-BB binding to FNIII$_{12-V15}$ (KD=2.1×10$^{-8}$ M), similar equilibrium binding was observed to FNIII$_{12-15}$ (KD=6.8×10$^{-9}$ M), FNIII$_{12-14}$ (KD=3.5×10$^{-8}$ M) and FNIII$_{12-13}$ (KD=7.5×10$^{-8}$ M) and somewhat weaker binding to IIICS (KD=3.5×10$^{-7}$ M). Interestingly, GFs binding to FNIII$_{12-V15}$ (HV) failed to demonstrate any diminution when up to 2.5 M NaCl was added or when pH was lowered to about 2.0 strongly indicating that charge is not required for the interaction. As judged by equilibrium binding, FNIII$_1$ and FNIII$_{1-2}$ bound PDGF-BB (KD=3.2×10$^{-8}$ M, 3.7×10$^{-8}$ M, respectively), while FNIII$_{3-6}$ did not. Plasma surface resonance confirmed these findings: FNIII$_1$ (KD=3.7×10$^{-7}$ M), FNIII$_{1-2}$ (KD=9.1×10$^{-9}$ M), and no binding with FNIII$_{3-6}$.

Four Homologous Peptides within 3 FN Domains Bind PDGF-BB

To further localize PDGF-BB binding within FNIII$_1$, we acquired a peptide from the central 76 amino acids (aa) of FNIII$_1$ (FN630-704) (FIG. 4), which has anti-angiogenic properties and promotes FN polymerization. This peptide as well as its two halves, FN630-667 and FN668-704, demonstrated PDGF-BB binding. Next, we looked for sequence homologies within the two halves of the peptide and discovered the sequence pattern noted above ([QN]-X(1,2)-[ST]-X(0,1)-[IG]-[QS]-[KRQ]-[YTM]-[IG]-X(4,5)-X(0,1)-[KR]-X(1,2)-X(1,2)-[RT]-X(1,2)-[KQTS]-X(2)-T) (SEQ ID NO:30) (see peptides 1-4). The four homologous peptides demonstrated binding with PDGF-BB while scrambled variants did not. These findings may explain similar PDGF-BB binding among FN heparin-binding domains, FNIII$_{12-V15}$, FNIII$_{12-15}$, FNIII$_{12-14}$, FNIII$_{12-13}$, and IIICS. Smaller peptides from FNIII$_1$ revealed PDGF-BB binding with FN630-648: WNAPQPSHISKYILRWRPK (SEQ ID NO:24); KD=3.4×10$^{-7}$ M) and a 15 aa peptide FN634-648: QPSHISKYILRWRPK (SEQ ID NO:25; KD=4.5×10$^{-7}$ M), but not with the 8 aa peptide FN634-641: QPSHISKY (SEQ ID NO:26), nor FN641-654:YILRWRPKNSVGRW (SEQ ID NO:27), nor FN648-667: KNSVGRWKEATIPGHLNSYT SEQ ID NO:28. Next, we determined if PDGF-BB-binding peptides from FNIII$_1$ could inhibit PDGF-BB binding to FNIII$_1$, FNIII$_{12-14}$ and IIICS. For initial experiments we selected peptide 1 and peptide 2. For control, we used scrambled peptide 1. Although peptide 1 showed marked inhibition of PDGF-BB binding to all three FN domains, neither peptide 2, nor the scramble variant of peptide 1 (FN634-658s), demonstrated inhibition of PDGF-BB binding to any of the FN domains. We noted that peptide 1 bound PDGF-BB with slightly less affinity than peptide 2 (KD=2.5× 10$^{-7}$ M, KD=1.1×10$^{-7}$ M, respectively).

PDGF-BB Bound to FNIII$_{1-2}$, FNIII$_{12-15}$ (H) or FNIII$_{12-V15}$ (HV) Retains Biological Activity To determine whether PDGF-BB, bound to recombinant FN domains, remained active, we investigated the migratory response of AHDF to 100 ng/ml PDGF-BB preloaded for two hours in engineered ECM containing C, H, and HV (268 nM bulk density, each) versus PDGF-BB preloaded on engineered ECM containing only C. Preloading was followed by 10 washes with DMEM. For each wash the engineered ECM was gently agitated on an orbital shaker for 5 minutes. The last wash had little or no detectable PDGF motogenic activity. As a positive control, PDGF-BB was added to the medium of both engineered ECM constructs. Fibroblasts migrated as well to PDGF-BB preloaded on engineered ECM tethered with C, H and HV as to PDGF-BB added to the culture medium. In contrast, no fibroblast migration occurred when PDGF was preloaded on engineered ECM containing C alone although cell migration on engineered ECM tethered with C responded well when PDGF was added to the medium. In other experiments, PDGF was preloaded on engineered ECM containing C alone or C plus FNIII$_{1-2}$ Fibroblasts migrated as well to PDGF-BB preloaded on engineered ECM tethered with C plus FNIII$_{1-2}$ as to PDGF-BB added to the culture medium. Similar data was acquired when human dermal microvascular endothelial cells (HDMEC) were used in these migration assays and either PDGF-BB or bFGF were preloaded on engineered ECM tethered with C alone or C in combination with H and HV or FNIII$_{1-2}$.

FN-Null Fibroblasts Require the FN Central Cell-Binding Domain & a PDGF-Binding Domain for Survival.

To further investigate the response of cells to PDGF-BB bound to FN domains, we investigated the survival response of mouse fibroblasts null for FN (FN−/−), or "FN-null". First we determined the response of FN-null cells to PDGF-BB in the absence of serum or other sources of exogenous FN. When PDGF was added 1 day after plating, FN-null cells failed to survive in the presence of PDGF while mouse cells heterozygous for FN (FN−/+) demonstrate increasing cell numbers to increasing concentrations of PDGF. Next, FN-null cells were plated on tissue culture plastic surfaces precoated with 0.15 μM GST-tagged FNIII$_{8-11}$±other FN domains known to have PDGF-BB binding activity and then PDGF-BB added 1 day later. On FNIII$_{8-11}$+FN domains with PDGF-BB binding activity (i.e., FNIII$_1$, FNIII$_{12-14}$ or IIICS, FN-null cells demonstrated increased survival with PDGF at 3 days while cells failed to survive on FNIII$_{8-11}$ alone. The best survival response was observed when cells were plated on which contains the FNIII$_1$ PDGF-binding domain in contiguous array with the FNIII$_{8-11}$ cell-binding domain. Similar results were observed when FNnull cells were plated on intact FN. Furthermore, cells survived on FNIII$_{1-11}$ even in the absence of PDGF-BB suggesting perhaps that the cells load endogenous PDGF on FN PDGF-binding domains. Importantly, differential response of FN-null cells, plated on different FN domains, to PDGF-BB was not secondary to differences in attachment as judged by cell counts two hours after plating. The FNIII$_{8-11}$ central cell binding domain was present in all circumstances. When PDGF-BB was added to FN-null cells 2 hrs after plating, they showed enhance survival on FNIII$_{8-11}$+FNIII$_{1-2}$, FNIII$_{12-14}$, FNIII$_{12-V15}$ or IIICS, but not FNIII$_{8-11}$ alone or FNIII$_{8-11}$+FNIII$_{3-6}$, and robust proliferation on intact FN, FNIII$_{1-11}$ or FNIII$_{8-V15}$.

Intact Fn Provides Promiscuous, but Selective, GF-Binding Sites

The survival of FN-null fibroblasts in the presence to PDGF-BB required substrate coated with intact FN or FNIII$_{8-11}$+a PDGF-binding FN domain. FNIII$_{8-11}$ alone and FNIII$_{8-11}$+FNII$_{3-6}$ did not support cell survival. These data strongly suggest that PDGF-BB binds intact FN. That is, PDGF-BB binding sites on FN are not cryptic as demonstrated for FN self-association sites. To address this directly, we performed equilibrium binding assays with PDGF-BB to FN adsorbed to a surface or coupled to agarose beads. In addition, we also investigated the ability of other growth factors to bind intact FN. PDGF-BB (KD=4.9×10$^{-8}$ M), TGF-β1 (KD=5.3×10$^{-8}$ M) and bFGF (KD=4.4×10$^{-8}$ M) bound intact FN while EGF, TGF-α and FGF-1 did not.

TGF-β1 and bFGF Binds the Same FN Domains and Peptides as PDGF-BB

To determine whether FN domains bind TGF-β1 and bFGF, equilibrium and kinetic binding was performed. TGF-β1 bound FNIII1-7 (KD=1.7×10$^{-8}$ M) and FNIII12-V15 (KD=9.7×10$^{-8}$ M), but not FN70 nor FNIII$_{8-11}$, as previously observed with PDGF-BB. Kinetic binding via plasmon surface resonance confirmed these findings (KD=1.8×10$^{-8}$ M, KD=2.5×10$^{-8}$ M, respectively). Similar data was acquired with bFGF, which bound to FNIII$_{1-7}$ (KD=4.1×10$^{-9}$ M) and FNIII 12-V15 (KD=3.7×10$^{-8}$ M), but not FN70 nor FNIII$_{8-11}$. EGF, TGF-α and FGF-1 failed to bind to any these FN domains.

Furthermore, FNIII$_1$, FNIII$_{12-14}$, FNIII$_{12-15}$ and IIICS, but not FNIII$_{3-6}$, also bound TGF-β1 (KD=6.2×10$^{-9}$ M, 7.6×10$^{-9}$ M, 1.6×10$^{-8}$ M, 7.4×10$^{-8}$ M, respectively) and bFGF (KD=3.5×10$^{-8}$ M, 1.9×10$^{-9}$ M, 1.3×10$^{-7}$ M, 5.8×10$^{-8}$ M, respectively). Peptides 1-4 could bind TGF-β1 and bFGF and peptide 1 completely inhibited TGF-β1 and bFGF binding to any recombinant FN domain as shown for PDGF-BB. Once again, EGF, TGF-α and FGF-1 failed to bind to any recombinant FN domain or synthetic peptide. In no case did any GF bind the 70 kDa amino terminus of FN domain (FN70), which includes the fibrin I and gelatin binding domains, nor FNIII$_{3-6}$, nor FNIII$_{8-11}$ (the central cell binding domain, C).

Growth Factor Binding Peptides (GFBP) Competitively Bind Fibronectin

Peptide sequences within TGF-β1, PDGF-BB, FGF-2, and VEGF-A were identified based on homology (see Table 1). The peptide sequences have the general formula C-X-[CNTV]-R-X(4)-[DEKR]-X-[DRS]-X-[DER]-X-[GILP] (SEQ ID NO:70).

TABLE 1

| Growth Factor | Homologous sequence | SEQ ID NO: |
|---|---|---|
| TGF-β1 | CCVRQLYIDFRKDLG | 29 |
| fPDGF-BB | CKTRTEVFEISRRLI | 12 |
| FGF-2 | CANRYLAMKEDGRLL | 31 |
| VEGF-A | CECRPKKDRARKENP | 13 |

Figure 9:
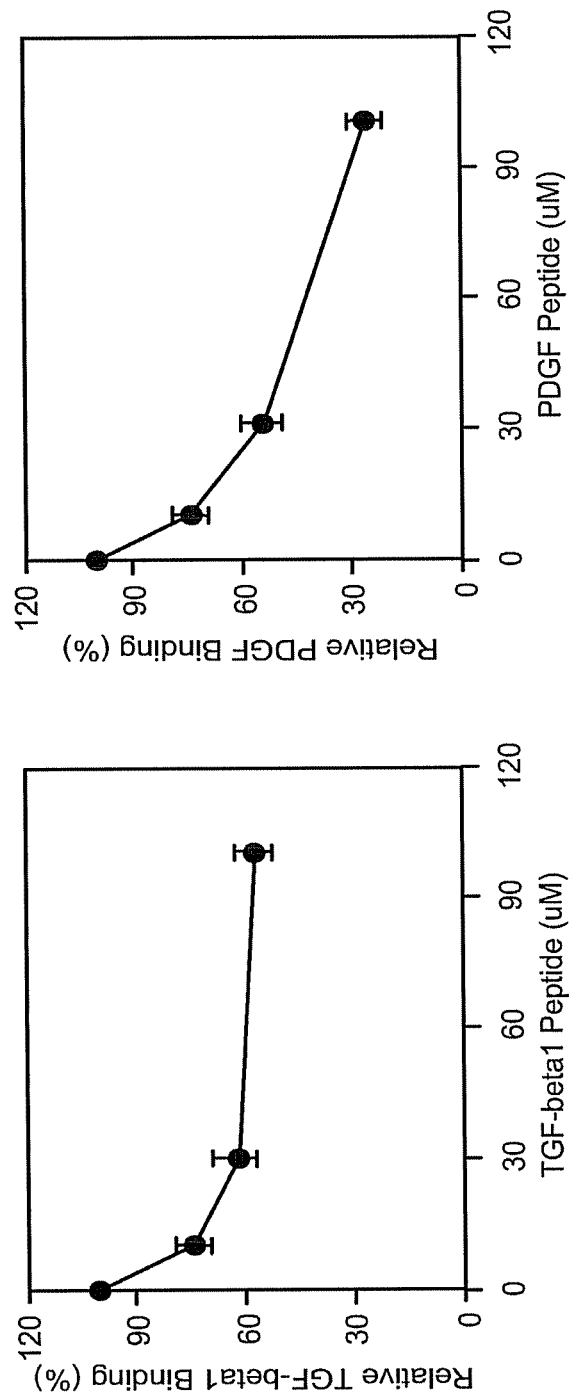
FIG. 9. Inhibition of TGF-β1 and PDGF-BB binding to intact human plasma FN with TGF-β1 and PDGF-BB FN-binding peptides, respectively. FN was adsorbed onto tissue culture plastic at a concentration of 0.125 μM and then excess protein-binding sites of the plastic blocked with 2% bovine serum albumin. Growth factor labeled with $I^{125}$ was incubated with FN-coated plates at 25° C. for 2 hours in the presence or absence of peptide. Data was calculated as [(GF binding in presence of peptide–background)/(GF binding in absence of peptide-background)]×100. n=3.

Two of these synthetic peptides (homologous to TGF-β1 and homologous to PDGF-BB) inhibit TGF-β1 and PDGF-BB binding to FN respectively (FIG. 9). Inhibition of TGF-β1 and PDGF-BB binding to intact human plasma FN was determined as follows. FN was adsorbed onto tissue culture plastic at a concentration of 0.125 μM and then excess protein-binding sites of the plastic blocked with 2% bovine serum albumin. Growth factor labeled with I$^{125}$ was incubated with FN-coated plates at 25° C. for 2 hours in the presence or absence of peptide. For example, relative binding of TGF-β1 to immobilized FN was determined for increasing concentrations of the synthetic peptide homologous to TGF-β1. The proportion of full-length TGF-β1 bound to immobilized FN decreased with increasing concentration of synthetic peptide homologous to TGF-β1. For example, relative binding of PDGF-BB to immobilized FN was determined for increasing concentrations of the synthetic peptide homologous to PDGF-BB. The proportion of full-length PDGF-BB bound to immobilized FN decreased with increasing concentration of synthetic peptide homologous to PDGF-BB. Such peptides and their derivatives can be used, for example, as immunoadjuvants and tumor suppressors for solid tumors by reducing the load of TGF-β1, PDGF-BB and possibly other growth factors from the tumor stroma thereby depriving the tumor of growth factors that immunosuppress cytotoxic T-cells, that protect the cancer cells from apoptosis, and that stimulate their growth, proliferation and migration.

Equilibrium Binding

20 μl of 50% v/v peptide-agarose beads are incubated with 125I-PDGF in 0.1 ml of binding buffer (DMEM+2% BSA) at room temperature for 2 hours with rotation. Beads are washed 6 times with DMEM. Bound PDGF-BB are released by the addition of 100 μl of 1M NaOH. The radioactivity bound to FN-beads are quantified in a γ-counter. Nonspecific binding are established from $^{125}$I-PDGF binding to nonconjugated beads, then specific binding derived by subtraction of non-specific binding from total binding. Binding constants (KD) and Bmax are determined from nonlinear regression of specific binding curves using Prism 4 from GraphPad Software, San Diego, Calif. "Scatchard plots" are derived from the KD and Bmax obtained with non linear regression analysis.

Surface Plasmon Resonance

In the Biacore2000 system, binding constants from kinetic data are determined by passing varying concentrations of FN peptides (analytes) over chip surfaces which are coupled with PDGF-BB (ligand), respectively. All kinetic experiments are carried out at 20° C. at a flow rate of 20 μl/min. For mass transport experiments, each analyte is injected at a fixed concentration and run at flow rates ranging from 5 to 75 μl/min. All analytes are injected over PDGF-BB ligand surfaces as well as over a control surface for 120 s, followed by 300 s of dissociation in running buffer. Regeneration of the sensor chip for subsequent injections is accomplished by pulse of 0.1% SDS. Mass transport experiments have detected little difference in response at different flow rates thus validating data from kinetic experiments. Sensorgrams are prepared and globally fitted using nonlinear least-squares analysis and numerical integration of the differential rate equations with the Biacore Bioevaluation software. Each sensorgram generated using a control surface is substracted from the corresponding experimental sensorgrams, and the resulting curves are transformed to concentration units using the molecular mass of the injected species, the equivalence of 1000 resonance units (RU) per 1 ng/mm$^2$, and a matrix thickness of 100 nm. Each data set, which consists of a series of sensorgrams from injections of different concentration of analyte over the same surface, are analyzed using kinetic models from Biaevaluation software.

Assay FN GF-Enhancing Peptides (GFEP) in Conjunction with PDGF for Their Ability to Promote Activation, Proliferation and Migration of Human Fibroblasts and Microvascular Endothelial Cells The following experiments will be focused on the ability of FN GFEP, identified herein, to promote the proliferation and migration of normal human cell strains, e.g., adult human dermal fibroblasts (AHDF) and human dermal microvascular endothelial cells (HDMEC).

Fibroblast culture will be used. Primary cultures of AHDF, from individuals of 30 to 40 years (NIA cell bank or ATCC) are cultured in DMEM containing 10% fetal calf serum at 37° C. and 100% humidity, 5% CO2 and 95% air (68). AHDF to be used in these experiments will be >99% pure on the basis of typical spindle cell shape in culture, positive immunostaining for vimentin and negative immunostaining for PECAM and keratin. Unless otherwise stated all experiments will be run in serum-free DMEM with cells at a PDL of 10-12.

Figure 8:
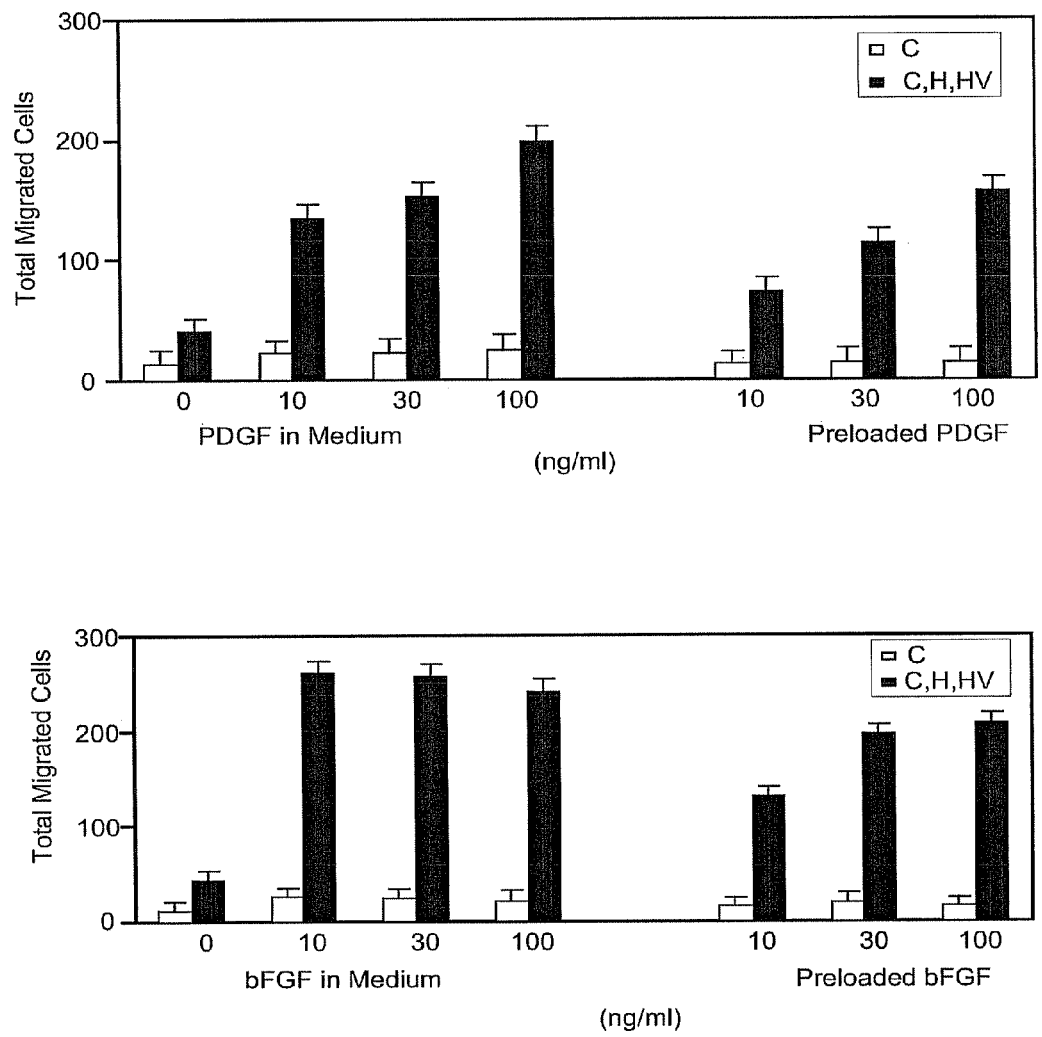
FIG. 8. PDGF-BB or bFGF binds crosslinked HA (xHA) decorated with C, H, HV, but not C alone, and stimulates human dermal microvascular endothelial cell (HDMEC) migration. Agarose droplets containing 12,000 HDMEC were placed on xHA and incubated in DMEM±PDGF at 30 ng/mL (left panel) or ±bFGF at 10 ng/mL (right panel) at 37° C. for 18 h. Migration was expressed as a cell number outside the agarose after DAPI staining and data acquisition and analysis by Metamorph 6 software. Six replicate agarose droplet assays were performed.

Endothelial cell culture will be used. Human dermal microvascular endothelial cells (HDMEC) are obtained from Cambrex (East Rutherford, N.J.) and grown on gelatin-coated plates in the presence of Endothelial Growth Medium (EGM) (Cambrex) as previously described. HDMEC to be used in these experiments will be >99% pure based on typical cobblestone monolayers in culture and positive immunostaining for PECAM (CD-31) and factor VIII-related antigen. All experiments will be done with HDMEC below passage 8. Unless otherwise stated experiments will be run in serum-free Endothelial Basal Medium (EBM). An example of this assay is shown in FIG. 8.

In order to determine the proliferation of AHDF and HDMEC in response to PDGF-BB with FN GFEP. The following experiment will be performed. To determine whether PDGF-BB in the presence of FN GFEP demonstrate enhanced activity, dose response experiments will be performed on AHDF and HDMEC. Cells will be seeded at 50% confluence in 48 well tissue culture plates in which wells have been precoated with 0.125 μM GST-tagged-$FNIII_{8-11}$ and blocked with 2% BSA. Tagging with GST is essential to assure optimal adsorption of $FNIII_{8-11}$. Blocking with 2% BSA is critical to prevent endogenous FN from being immediately deposited on the tissue culture plastic. Cells will be allowed to attach to GST-tagged-$FNIII_{8-11}$ coated wells for 2 h in serum-free DMEM and then add PDGF-BB±peptides in the presence of 1% BSA for 4-18 hrs. At the end of the stimulation period, PDGF-replete media will be removed and plates washed 3 times with PBS. Fresh serum-free DMEM will be added to all wells and incubation continued for a total of 2 to 5 days. At the end of each experimental time point, all samples will be fixed with 2% glutaraldehyde and stained with 0.1% crystal violet. Photomicrographs of the stained cells will be obtained using a Nikon SMX800 zoom stereomicroscope (Japan) with Spot RT camera attachment and the total cell number quantified using MetaMorph® software (Universal Imaging, Downington, Pa.). All conditions will be assayed in quadruplicate as the variance is usually 10% or less. Alternatively, cell number will be quantified using the Quantos Cell Proliferation Assay (Stratagene) that measures the total amount of extracted DNA. Standard curves will be generated for known quantities of purified DNA (Sigma) and for DNA extracted from known concentrations of each cell type.

Figure 7:
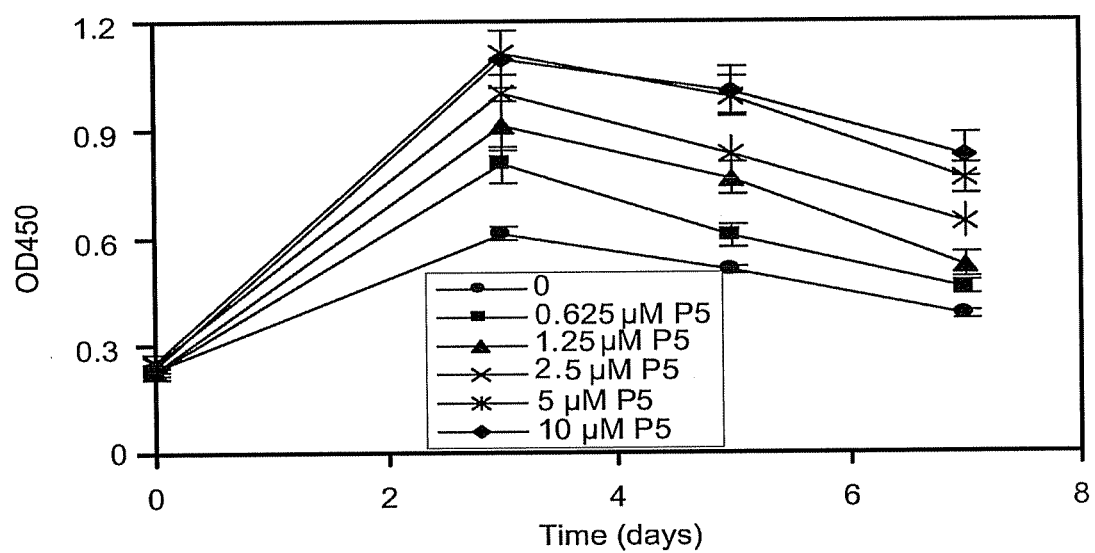
FIG. 7. P5 (SEQ ID NO:37) enhanced AHDF proliferation response to PDGF-BB. AHDF cells were cultured at 4,000 cells/well in uncoated 96-well plates. Cells were incubated in DMEM for 4 hrs, and then further incubated in DMEM, 2% BSA, 30 ng/mL PDGF-BB with and without Peptide 5 (P5) at 37° C. for 1 week. Proliferation was estimated by the XTT assay (Promega) according to the manufacturer's instructions (mean±SD, n=4).

Initial experiments will be done with 30 ng/ml PDGF-BB. Once an optimal PDGF stimulation time has been determined, PDGF doses responses±2 μM FN GFEP will be obtained. Such peptides will be selected from those described herein or from candidate compounds (e.g., peptides) identified using the screening methods described herein. Once an optimal PDGF dose has been chosen, peptides will be tested at 0.1, 0.3, 1, 3 and 10 μM for their ability to support cell proliferation in conjunction with PDGF-BB. Peptides alone and scrambled peptides will serve as controls. An example of this assay is shown in FIG. 7.

Statistical differences among conditions will be determined by ANOVA followed by Tukey post-hoc analysis.

To assay chemotaxis of AHDF and HDMEC in response to PDGF-BB with FN GFEP, the following experiment will be performed. A previously described assay (Postlethwaite et al., *J. Clin. Invest.* 87:2147-2152, 1991) will be used to determine the effects of FN GFEP on PDGF-induced chemotaxis. Prior to experiments with FN GFEP, the optimal PDGF concentration for HDMEC chemotaxis will be determined (155 ng/ml PDGF-BB is optimum for fibroblast chemotaxis). PDGF at optimal concentration for AHDF or HDMEC chemotaxis will be preincubated without or with FN GFEPs for 30 minutes and then loaded to the lower wells of 48-well microchemotaxis chambers. AHDF and HDMEC will placed into the upper wells of the chambers and incubated 4 hours at 37° C. After careful aspiration of medium from the upper chambers, filters will be removed, fixed and stained for visual quantification under a light microscope. GFEPs selected from peptides (e.g., fibronectin or vitronectin fragments) described herein or from candidate compounds (e.g., peptides) identified using the screening methods described herein will be tested at a concentration range from 0.1, 0.3, 1, 3 and 10 μM. GFEPs alone and scrambled peptides will serve as controls. All conditions will be assayed in replicates of 8 as the variance is usually 20%.

Statistical differences among conditions will be determined by ANOVA followed by Tukey post-hoc analysis.

In order to determine AHDF expression of KGF and HGF protein in response to PDGF-BB with FN GFEP, the following experiment will be performed. Although human epidermal cells (HEK) produce PDGF-AB and -BB they do not respond to them directly (Ansel et al., *J. Clin. Invest.* 92:671-678, 1993), rather PDGF stimulates dermal fibroblasts to produce keratinocytes growth factor (KGF) and hepatocyte growth factor (HOF) to which HEK respond in a paracrine fashion (Li and Tseng, *J. Cell. Physiol.* 172:361-372, 1997; Lederle et al., *Am. J. Pathol.* 169:1767-1783, 2006). If GFEP enhance the response of AHDF to PDGF, it is likely that they will stimulate HEK indirectly through this mechanism. This hypothesis will be tested by KGF and HGF ELISA (R&D Systems, Minneapolis, Minn.) on extracts of AHDF that have been stimulated with PDGF-BB in the presence or absence of FN GFEP. AHDF will be stimulated with 1, 3, 10 and 30 ng/ml PDGF-BB for 24, 48 or 72 hrs and then detergent-extracted in an enzyme inhibitor cocktail as previously described (Wang et al., *J. Biol. Chem.* 280:28803-28810, 2005). KGF and HGF in cell extracts will be quantified by ELISA according to the manufacturer's protocol. Finally, FN GFEPs will be tested for their ability to enhance PDGF-induced KGF and HGF protein expression. Peptides will be tested at 0.1, 0.3, 1, 3 and 10 μM with both an optimal and suboptimal dose of PDGF-BB for KGF and HGF expression. Peptides alone and scrambled peptides will serve as controls.

Statistical differences among conditions will be determined by ANOVA followed by Tukey post-hoc analysis.

FN-Null Cell Assay

Experiments described previously demonstrated that $FNIII_{8-11}$ tethered to GF-binding domains of fibronectin promote FN-null cell survival and proliferation in the presence of PDGF-BB. These observations were used to develop an assay to identify GF-binding peptides that when presented in combination with $FNIII_{8-11}$ allows FN-null cell survival (in the absence of PDGF-BB) and FN-null cell proliferation (in the presence of PDGF-BB). This assay was used, e.g., to identify new GF-binding peptides that promote FN-null cell survival and proliferation.

Figure 5A:
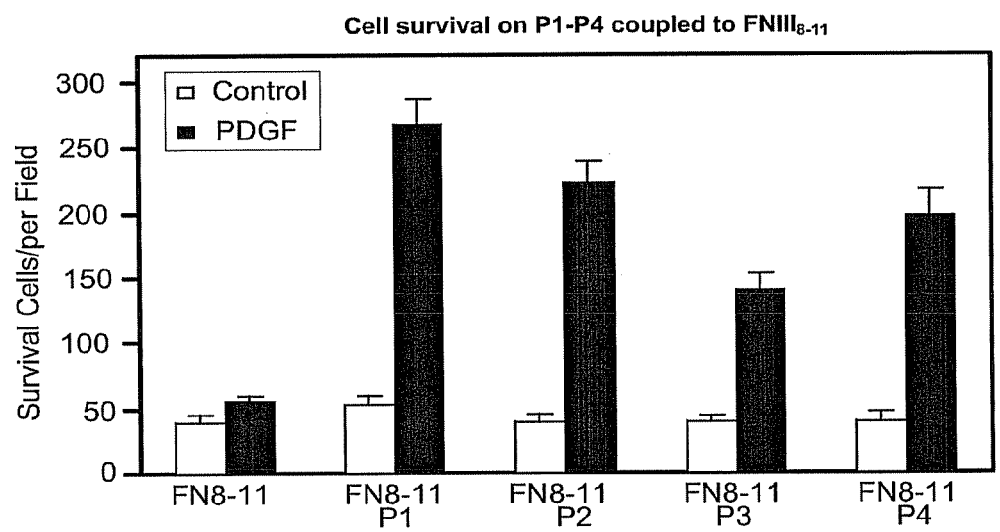
FIG. 5. FN-null fibroblast response to PDGF-BB requires FN GF-binding peptides. (A) FN-null cells were cultured in 96-well plates coated with $FNIII_{8-11}$ or $FNIII_{8-11}$ coupled to Cys-tagged peptides (P1-P4; SEQ ID NO:33 to SEQ ID NO:36, respectively) via PEGDVS. (B) Experiment as in A except that scrambled P1-P4 peptides were used. (C) FN-null cells were cultured on $FNIII_{8-11}$ with P5 (SEQ ID NO:37) and derivatives (P12-P18; SEQ ID NO:38 to SEQ ID NO:44, respectively). Derivatives were created by sequential residue trimming from the amino-terminus. (D) FN-null cells were cultured on $FNIII_{8-11}$ with P5 and derivatives created from sequential residue trimming from the carboxy terminus (P19-P24; SEQ ID NO:45 to SEQ ID NO:50, respectively).
Figure 5B:
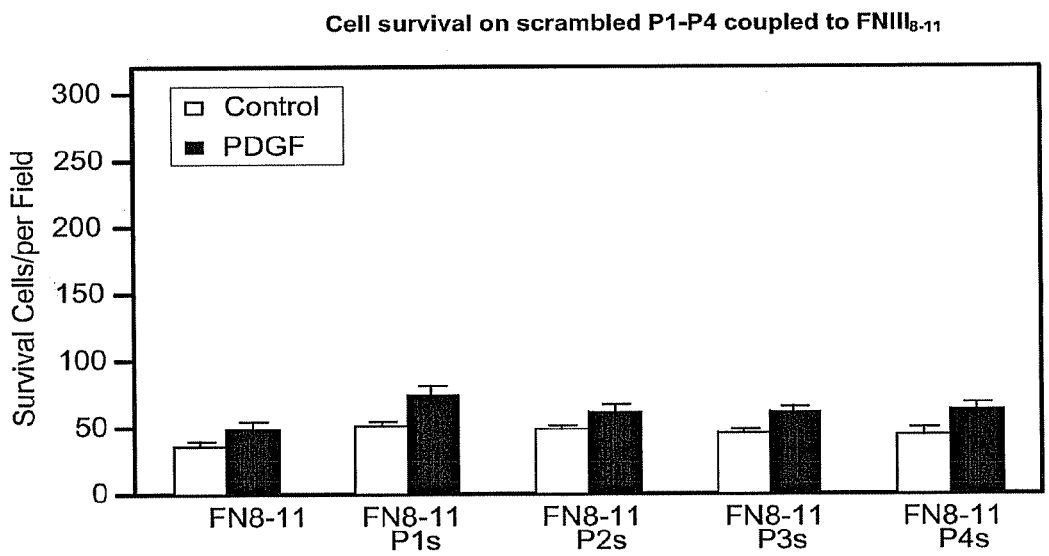

To bind test peptides, e.g., GF-binding peptides derived from fibronectin, to the culture surface, 0.125 μM Cys-tagged $FNIII_{8-11}$ was incubated with a 200 molar excess of the homobifunctional crosslinker polyethylene(glycol) divinylsulfone PEGDVS (18 h at 4° C.), then adsorbed onto tissue culture wells for 18 h at 4° C. After thorough rinsing Cys-tagged test peptides were added (18 h at 4° C.). Residual protein-binding sites on the plates were blocked with 2% BSA. FN-null cells were incubated on precoated plates in DMEM for 4 hrs, and then further incubated in DMEM+2% BSA±30 ng/ml PDGF- BB at 37° C. for 3 days. Cells in three 10× fields were counted in each of 4 wells (mean±SD, n=12). FN-null cells were cultured at 4,000 cells/well in 96-well plates. Using the assay described above, peptides 1-4, as described under Formula I and in Table 2, were identified as supporting survival of FN null cells (e.g., FIG. 5A). Scrambled peptides 1-4, used as a control, failed to support survival of FN null cells in the presence of PDGF-BB (e.g., FIG. 5B).

Figure 6:
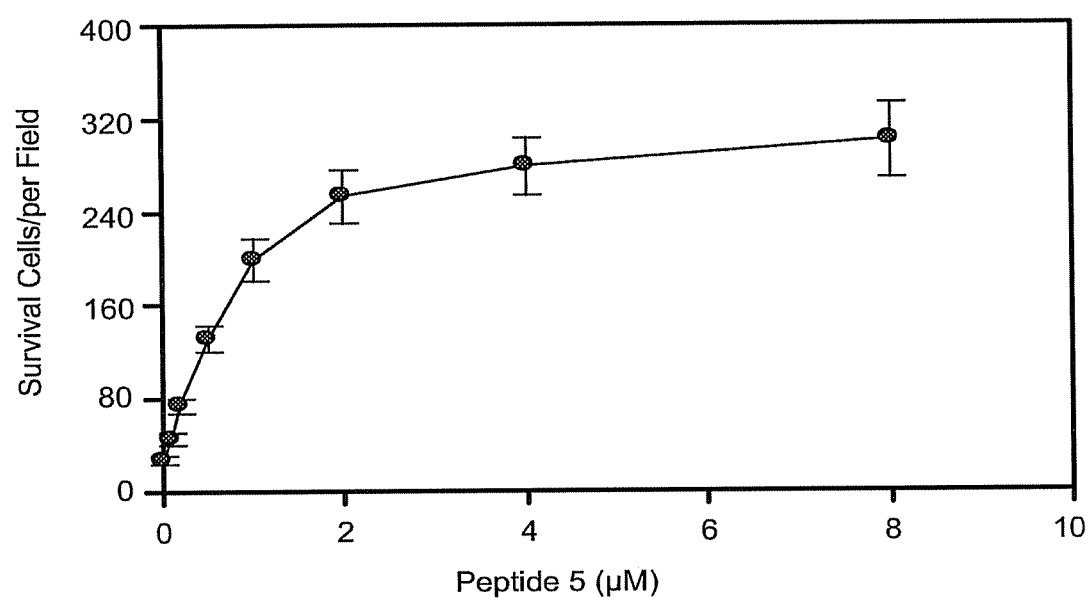
FIG. 6. FN-null fibroblast response to soluble, unconjugated P5 (SEQ ID NO:37). FN-null cells were cultured at 4,000 cells/well in 96 well plates precoated with 0.125 mM of $FNIII_{8-11}$ in DMEM for 4 hrs, and then further incubated in DMEM+2% BSA with or without the indicated concentrations of Peptide 5 at 37° C. for 3 days. Cells were counted in three 10× fields in each of 4 wells (mean±SD, n–12).

Peptide 1, but not peptides 2-4, also supported FN null cell survival and proliferation when added directly to media with or without PDGF-BB (e.g., FIG. 6). These data indicated that peptide 1 had intrinsic growth factor activity and in addition could enhance PDGF-BB activity. Peptide 5, a subfragment of peptide 1 with PDGF-BB binding activity (KD=450 nM) as described under Formula II, also supported FN null cell survival and proliferation when added directly to media with or without PDGF-BB. Scrambled variants of peptides 1 and 5 had no activity in these assays.

Variants of peptide 5 derived from fibronectin were generated by removing one amino acid at a time from the N-terminus or C-terminus of Peptide 5 (Table 2). These peptides (P12-P24) were added directly to medium with or without PDGF-BB.

thesized by standard technique, and tested in the FN null cell assays. The vitronectin peptide PSLAKKQRFRHRNR (SEQ ID NO:52), but not its scrambled control, supported FN null cell survival and proliferation in the presence of PDGF-BB. Thus, these two peptides (and by extension Formula IV peptides) were identified by their ability to support FN null cell survival or proliferation, not their ability to bind growth factors.

High-Throughput Screen for Compounds that Inhibit FN-Null Cell Survival or Proliferation The FN-null cell viability assay wherein FN-null cells are cultured in the presence of $FNIII_{8-11}$ or other cell attachment moiety, a GF-binding and/or attachment peptide, and optionally a growth factor, e.g., PDGF-BB, will be used to identify test compounds that inhibit FN-null cell survival or proliferation. Screening methods described herein will be used to identify test compounds that inhibit FN-null cell survival or proliferation. Test compounds will include synthetic peptides homologous to growth factors, organic compounds contained in chemical libraries, and peptidomimetics amongst others.

Test compounds identified by this assay will be candidate compounds for use in the treatment, for example, of cancer and for use in, for example, cosmetic therapies, e.g., for the

TABLE 2

Peptide sequences and location within plasma FN

| Peptide name | Peptide location in plasma FN | Peptide sequence | SEQ ID NO: |
|---|---|---|---|
| P1 | FN634-658 | QPSHISKYILRWRPKNSVGRWKEAT | 33 |
| P2 | FN680-704 | QLISIQQYGHQE VTRFDFIIISTST | 34 |
| P3 | FN1852-877 | NGQTPIQRTIKPDVRSYTITGLQPGT | 35 |
| P4 | FN2043-2067 | QPSVGQQMIFEEHGFRR TTPPTTAT | 36 |
| P5 | FN634-648 | QPSHISKYILRWRPK | 37 |
| P12 | FN635-648 | PSHISKYILRWRPK | 38 |
| P13 | FN636-648 | SHISKYILRWRPK | 39 |
| P14 | FN637-648 | HISKYILRWRPK | 40 |
| P15 | FN638-648 | ISKYILRWRPK | 41 |
| P16 | FN639-648 | SKYILRWRPK | 42 |
| P17 | FN640-648 | KYILRWRPK | 43 |
| P18 | FN641-648 | YILRWRPK | 44 |
| P19 | FN635-647 | PSHISKYILRWRP | 45 |
| P20 | FN635-646 | PSHISKYILRWR | 46 |
| P21 | FN635-645 | PSHISKYILRW | 47 |
| P22 | FN635-644 | PSHISKYILR | 48 |
| P23 | FN635-643 | PSHISKYIL | 49 |
| P24 | FN635-642 | PSHISKYI | 50 |

Figure 5C:
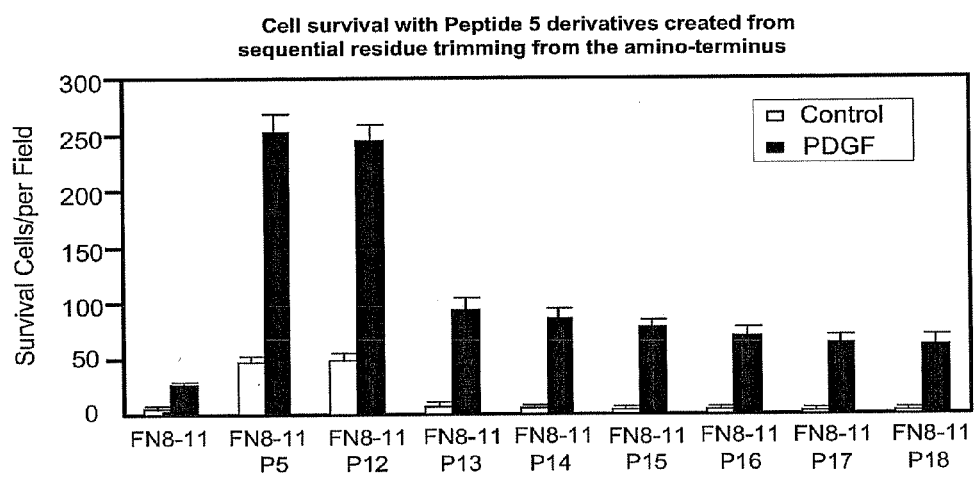
Figure 5D:
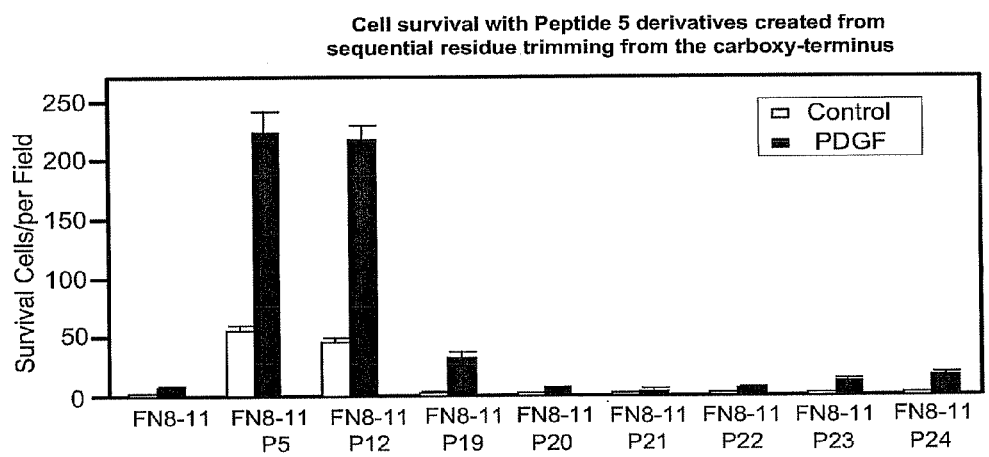

P12 was the smallest peptide capable of supporting FN-null cell survival or proliferation and it did so in the presence or absence of PDGF-BB. Removal of either the N-terminal proline or the C-terminal lysine completely eliminated this activity (e.g., FIGS. 5C and D). By homology (see Formula IV) the vitronectin peptide PSLAKKQRFRHRNR (SEQ ID NO:51) was identified from a search of known human proteins, syntreatment of aging. Although applicants do not wish to be bound by theory, growth factor peptides and their derivatives can be used, for example, as immunoadjuvants and tumor suppressors for solid tumors by reducing the load of TGF-β1, PDGF-BB and possibly other growth factors from the tumor stroma thereby depriving the tumor of growth factors that immunosuppress cytotoxic T-cells, that protect the cancer cells from apoptosis, and that stimulate their growth, proliferation and migration may be useful in inhibiting FN-null cell survival or proliferation.

Studies of Treatment of Porcine Burns with PDGF-BB and Formula IV Peptide Formulations Four female, 20-30 kg, domestic pigs will be used for cutaneous wound procedures.

Study Protocol: The animals will be sedated with Talazine (Tiletamine and Zolazepam, Fort Dodge Lab, Fort Dodge, Iowa) 5 mg/kg IM. The pigs will then be intubated endotracheally and maintained tinder a surgical plane of anesthesia with isoflurane 0.5-2.5% in room air. The flank and back hair will be clipped with electric hair clippers and the skin will be scrubbed with a povidone iodine solution as previously described.

According to previous protocol, standardized deep partial-thickness burns will be created on the animals' backs and flanks by applying a 2.5-cm by 2.5-cm, 150-gram aluminum bar preheated in hot water to 80° C. The burns will be created on either side of the vertebral column between the forelegs and hindlegs. The heated bar will be wiped dry just prior to application to prevent water droplets from creating a steam burn on the skin. The bar will then be placed at a vertical position perpendicular to the skin's surface and applied for a period of 20 seconds with all pressure supplied by gravity. This burn model results in damage to the upper 30-50% of the dermis and has been shown to be highly reproducible (Singer et al., *Acad. Emerg. Med.* 7:1-6, 2000). 24 burns will be evenly distributed on both sides of the back of four pigs. Since pigs do not form blisters after thermal injury, debridement of the necrotic epidermis will be performed immediately after injury in order to simulate burns in humans where blisters may form and subsequently rupture (Singer et al., *Acad. Emerg. Med.*, 7:114-119, 2000). Debridement will be performed by gently rubbing dry gauze against the surface of the burn until the necrotic epidermis is peeled away from the entire burn surface. Interventions: On the back skin of each pig, equal sets of 4 burns will be randomly treated with one of the 6 study treatments. Peptides selected for testing will be synthesized in a GMP faculty (American Peptide, Vista, Calif.) and diluted in sterile, endotoxin-free PBS with sterile, endotoxin-free 2% porcine serum (HyClone, Logan, Utah) to avoid peptide loss via nonspecific surface adsorption. Sterile, endotoxin-free recombinant PDGF-BB (R&D Systems) will also be diluted in PBS with 2% porcine serum. Final concentration of peptides with and without PDGF-BB will be compounded in a 30% pluronic lecithin gel using a sterile, endotoxin-free PLO kit (Transderma, Coquitlam, BC, Canada). PBS with 2% porcine serum in a 30% pluronic gel will be used as a treatment control. Wounds will receive 150 µl of treatment gels applied topically on a daily basis for the first week and twice weekly thereafter. Then burns will be covered with dry non-adherent gauze (Telfa, Kendall Company, Mansfield, Mass.) and the burned areas covered with a gauze bandage roll (Conform, Kendall Healthcare Products Company, Mansfield, Mass.) and an adhesive elastic bandage (Elastoplast, Beiersdorf-Jobst, Inc., Rutherford College, N.C.). In order to prevent dressing removal, staples will be applied to the periphery of the dressings. Dressing changes will be applied as above after each treatment application. All of the animals will be treated with a Fentanyl transdermal patch post operatively for analgesia management.

Survival surgery of pigs and wound site harvest is done under general anesthesia. Pigs will be fasted for 24 hours before the surgical procedures. Atropine is given pre-op at a dose of 0.05 mg/kg. For induction of general anesthesia 4.4 mg/kg Telazol and, 2.2 mg/kg Xylazine and 0.22 mg/kg Butorphanol are administered IM. The animal is then intubated and held at the stage of surgical anesthesia with Isoflurane (1-3%) and oxygen. Since covered cutaneous wounds cause minor pain to humans that require at most acetominophin, animals are treated likewise receiving 10-20 mg/kg acetominophen twice daily after survival surgery.

Euthanasia is accomplished with intravenous 100 mg/kg pentobarbital and 2 mg/kg xylazine.

Pharmaceutical and Cosmetic Compositions

The following examples further describe and demonstrate embodiments within the scope of the present invention. The examples are given solely for the purpose of illustration and are not to be construed as limitations of the present invention, as many variations thereof are possible without departing from the spirit and scope of the invention.

As an illustration of the invention, several cosmetic formulae will be cited. The formulae are representative of, but do not restrict, the invention:

Gel 1 g/100 g White soft paraffin 1.5 Cyclomethicone 6.0 Crodacol C90 0.5 Lubrajel.sup.R MS10 Triethanolamine 0.3 Palmitoyl-PSHISKYILRWRPK-OH 0.0005 (SEQ ID NO:53) Water, preservatives, fragrance q.s. 100 g The gel can be made by dissolving the peptide in the water at 80° C., mixing the first three components (paraffin, silicone and Crodacol) at 80° C., then blending the two phases, cool to 30° C., add the lubrajel, the preservatives and the fragrance. This gel, freshly obtained, may be used for daily application to the skin of the face, in particular around the eyes to reduce edematous infiltrations.

Cream 2 g/100 g Volpo S2 2.4 Volpo S20 2.6 Prostearyl 15 8.0 Beeswax 0.5 Stearoxydimethicone 3.0 Propylene glycol 3.0 Carbomer 0.25 Triethanolamine 0.25 Ceramide H03 (SEDERMA) 0.5 Acetyl-PSHISKYILRWRPK-OH 0.001 (SEQ ID NO:54) Water, preservatives, fragrance q.s. 100 g This emulsion can be used to moisturize, restructure and soothe the facial skin, in particular on areas of fragile skin and to treat wrinkles. To produce the emulsion, one can dissolve ceramide HO3 in volpo 52, S20 and prostearyl 15 at 85° C., add beeswax and stearoxydimethicone; mix in the other ingredients in the water phase at 75-80° C., then blend the two phases, cool, and add fragrance. Ceramide HO3 is Tirhydroxypalmitamido myristyl ether.

Moisturizing and Anti-Wrinkle Foundation

Compound % (w/w) Demineralized water 53.36 10% KOH 1.30 Polysorbate 80 0.10 Titanium dioxide 6.00 Talc 3.05 Yellow iron oxide 1.80 Red iron oxide 1.00 Black iron oxide 0.15 Propylene glycol 6.00 Magnesium aluminum silicate 1.00 Sodium carboxymethylcellulose 0.12 DiPPG3 myristyl ether adipate 12.00 Isostearyl neopentanoate 4.00 Crodafos CS 20 4.00 Steareth-10 2.00 Cetyl alcohol 0.50 Steareth-2 0.50 Ceramide 2 (N-stearoyl-0.10 sphinganine) PSHISKYILRWRPK-OH 0.0004 (SEQ ID NO:55) Preservatives q.s.

Subjects can be enrolled in a study on the use of a foundation cream as per above. The wrinkles around the eyes can be evaluated by self-evaluation/questionnaire and by the impression method. The product is applied to the target areas once daily for 56 days. The determinations are conducted on day 0 and day 56. As a control, the sites are treated with the same foundation cream devoid of peptide and are evaluated for improvement in the symptoms of cutaneous aging.

A number of embodiments of the invention have been described. Nevertheless, it will be understood that various modifications may be made without departing from the spirit and scope of the invention. Accordingly, other embodiments are within the scope of the following claims.

What is claimed is:

1. An isolated polypeptide consisting of the sequence: PSHISKYILRWRPK (SEQ ID NO:9), PSLAKKQRFRHRNR (SEQ ID NO:10), or ISKYILRWRPK (SEQ ID NO:41).

2. A physiologically acceptable composition comprising the isolated polypeptide of claim 1.

3. The physiologically acceptable composition of claim 2, wherein the composition is formulated for topical administration.

4. A method of treating a patient who has a wound, the method comprising administering to the patient a therapeutically effective amount of the physiologically acceptable composition of claim 2.

5. The method of claim 4, wherein the wound is a surgical incision or extirpation, a traumatic injury, a burn, a lesion, or an ulceration of the patient's skin, mucosa, connective tissue, fascia, ligament, tendon, cartilage, nerve or muscle or a wound to the patient's bone.

6. The method of claim 5, wherein the wound is a burn.

7. An isolated, cyclized polypeptide consisting of the sequence: CPSHISKYILRWRPKC (SEQ ID NO:82), CPSLAKKQRFRHRNRC (SEQ ID NO:83), or CISKYILRWRPKC (SEQ ID NO:84).

8. A physiologically acceptable composition comprising the isolated polypeptide of claim 7.

9. The physiologically acceptable composition of claim 8, wherein the composition is formulated for topical administration.

10. A method of treating a patient who has a wound, the method comprising administering to the patient a therapeutically effective amount of the physiologically acceptable composition of claim 9.

11. The method of claim 10, wherein the wound is a surgical incision or extirpation, a traumatic injury, a burn, a lesion, or an ulceration of the patient's skin, mucosa, connective tissue, fascia, ligament, tendon, cartilage, nerve or muscle or a wound to the patient's bone.

12. The method of claim 11, wherein the wound is a burn.

13. An isolated, cyclized polypeptide of claim 7, wherein the polypeptide consists of the sequence PSHISKYILRWRPK (SEQ ID NO:9)

14. A physiologically acceptable composition comprising the isolated polypeptide of claim 13.

15. The physiologically acceptable composition of claim 14, wherein the composition is formulated for intravenous administration.

16. A method of treating a patient who has a wound, the method comprising administering to the patient a therapeutically effective amount of the physiologically acceptable composition of claim 15.

17. The method of claim 16 wherein the wound is a surgical incision or extirpation, a traumatic injury, a burn, a lesion, or an ulceration of the patient's skin, mucosa, connective tissue, fascia, ligament, tendon, cartilage, nerve or muscle or a wound to the patient's bone.

18. The method of claim 17, wherein the wound is a burn.

* * * * *

UNITED STATES PATENT AND TRADEMARK OFFICE
CERTIFICATE OF CORRECTION

PATENT NO. : 8,759,300 B2  
APPLICATION NO. : 12/663993  
DATED : June 24, 2014  
INVENTOR(S) : Richard A. Clark Page 1 of 1

It is certified that error appears in the above-identified patent and that said Letters Patent is hereby corrected as shown below:

In the Claims:

At column 113, lines 7-10, cancel the text beginning with "7. An isolated, cyclized polypeptide" and ending with "CISKYILRWRPKC (SEQ ID No:84).", and insert the following text in place thereof:

--7. An isolated, cyclized polypeptide consisting of the sequence: PSHISKYILRWRPK (SEQ ID NO:9), PSLAKKQRFRHRNR (SEQ ID NO:10), ISKYILRWRPK (SEQ ID NO:41), CPSHISKYILRWRPKC (SEQ ID NO:82), CPSLAKKQRFRHRNRC (SEQ ID NO:83), or CISKYILRWRPKC (SEQ ID NO:84).--

At column 114, line 6, replace the term "(SEQ ID NO:9)" in claim 13 with the term --(SEQ ID NO:9).--

Signed and Sealed this  
Ninth Day of September, 2014

Michelle K. Lee  
*Deputy Director of the United States Patent and Trademark Office*